(12) United States Patent
Kim et al.

(10) Patent No.: US 12,286,635 B2
(45) Date of Patent: Apr. 29, 2025

(54) OLEIC ACID-ENRICHED PLANT BODY HAVING GENETICALLY MODIFIED FAD2 AND PRODUCTION METHOD THEREOF

(71) Applicant: TOOLGEN INCORPORATED, Seoul (KR)

(72) Inventors: Seok Joong Kim, Seoul (KR); Ok Jae Koo, Gyeonggi-do (KR); Min Hee Jung, Seoul (KR); Ye Seul Kim, Seongnam-si (KR)

(73) Assignee: TOOLGEN INCORPORATED, Seoul (KR)

( * ) Notice: Subject to any disclaimer, the term of this patent is extended or adjusted under 35 U.S.C. 154(b) by 182 days.

(21) Appl. No.: 17/706,921

(22) Filed: Mar. 29, 2022

(65) Prior Publication Data
US 2022/0228160 A1 Jul. 21, 2022

Related U.S. Application Data

(62) Division of application No. 16/471,443, filed as application No. PCT/KR2017/010576 on Sep. 26, 2017, now abandoned.
(Continued)

(51) Int. Cl.
*C12N 15/82* (2006.01)
*C12N 9/22* (2006.01)
*C12N 15/11* (2006.01)

(52) U.S. Cl.
CPC ........... *C12N 15/8247* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS 8,143,485 B2 3/2012 Despeghel et al.
2012/0102587 A1 4/2012 Anai
(Continued)

FOREIGN PATENT DOCUMENTS

KR 10-2008-0107415 A 12/2008
KR 10-2015-0043538 A 4/2015
(Continued)

OTHER PUBLICATIONS

Office Action from corresponding U.S. Appl. No. 16/471,443, dated Apr. 11, 2023.
(Continued)

*Primary Examiner* — Matthew R Keogh
*Assistant Examiner* — Rebecca Stephens
(74) *Attorney, Agent, or Firm* — Harness, Dickey & Pierce, P.L.C.

(57) ABSTRACT

The present invention relates to an artificially manipulated unsaturated fatty acid biosynthesis-associated factor and use thereof to increase the content of a specific unsaturated fatty acid of a plant body. More particularly, the present invention relates to a system capable of artificially controlling unsaturated fatty acid biosynthesis and a plant body produced thereby, which include an artificially manipulated unsaturated fatty acid biosynthesis-associated factor to control unsaturated fatty acid biosynthesis and a composition capable of artificially manipulating the factor. In a specific aspect, the present invention relates to artificially manipulated unsaturated fatty acid biosynthesis-associated factors such as FAD2, FAD3, FADE, FAD7 and FAD8 and/or an unsaturated fatty acid biosynthesis controlling system by an expression product thereof.

7 Claims, 12 Drawing Sheets
Specification includes a Sequence Listing.

Related U.S. Application Data

(60) Provisional application No. 62/438,018, filed on Dec. 22, 2016.

(56) References Cited

U.S. PATENT DOCUMENTS

| | | | |
|---|---|---|---|
| 2015/0067922 | A1 | 3/2015 | Yang et al. |
| 2015/0284727 | A1 | 10/2015 | Kim et al. |
| 2016/0130600 | A1 | 5/2016 | Fillatti et al. |
| 2016/0208271 | A1 | 7/2016 | Cigan et al. |

FOREIGN PATENT DOCUMENTS

| | | | |
|---|---|---|---|
| KR | 10-1601868 B1 | | 3/2016 |
| KR | 10-1656237 B1 | | 9/2016 |
| WO | WO-2007/095243 A2 | | 8/2007 |
| WO | WO-2008-006171 A1 | | 1/2008 |
| WO | WO 2011/005998 | * | 1/2011 |
| WO | WO-2011/005998 A1 | | 1/2011 |
| WO | WO-2012/106105 A1 | | 8/2012 |
| WO | WO-2014/039692 A2 | | 3/2014 |
| WO | WO-2014/039702 A2 | | 3/2014 |
| WO | WO-2014/065596 A1 | | 5/2014 |
| WO | WO-2014/141147 A1 | | 9/2014 |
| WO | WO 2015/026886 | * | 2/2015 |
| WO | WO-2015/026886 A1 | | 2/2015 |

OTHER PUBLICATIONS

Sequence Accession BBN97124, Nov. 6, 2014, sequence alignment attached at the end of the office action. (Year: 2014).

Office Action from corresponding U.S. Appl. No. 16/471,443 dated Jun. 30, 2022.

Pham, A.T., et al. (2011) "A novel FAD2-1 A allele in a soybean plant introduction offers an alternate means to produce soybean seed oil with 85 percent oleic acid content.", *Theoretical and Applied Genetics*, vol. 123, Issue 5, pp. 793-802, Sep. 2011.

International Search Report from corresponding PCT Application No. PCT/KR2017/010576, dated Jan. 31, 2018, with English translation.

International Written Opinion from corresponding PCT Application No. PCT/KR2017/010576, dated Jan. 31, 2018.

Office Action from corresponding Korean Patent Application No. 10-2017-0123904, mailed on Jan. 27, 2019.

Office Action (Final) from corresponding Korean Patent Application No. 10-2017-0123904, mailed on Jul. 15, 2019.

Demorest, Z. L., et al.; "Direct stacking of sequence-specific nuclease-induced mutations to produce high oleic and low linolenic soybean oil", BMC Plant Biology (2016) 16:225.

Office Action from corresponding Korean Patent Application No. 10-2017-0123904, dated Sep. 18, 2019.

Notice of Allowance from corresponding Korean Patent Application No. 10-2017-0123904, dated Mar. 17, 2020.

Notice of Allowance from corresponding U.S. Appl. No. 16/471,443, issued Jan. 12, 2022.

Office Action (Non-Final) from corresponding U.S. Appl. No. 16/741,443, issued Jul. 26, 2021.

Office Action from corresponding Chinese Patent Application No. 201780086719.3, issued on Aug. 31, 2022.

Morineau, C., et al.; "Selective gene dosage by CRISPR-Cas9 genome editing in hexaploid Camelina sativa", Plant Biotechnology Journal (2017) 15, pp. 729-739.

Walter, K. L., et al.; "Molecular and phenotypic characterization of Als1 and Als2 mutations conferring tolerance to acetolactate synthase herbicides in soybean", Pest Manag Sci 2014; 70: 1831-1839.

Examination Report No. 1 from corresponding Australian Patent Application No. 2022204029, dated Jul. 25, 2024.

Examination Report No. 2 from corresponding Australian Patent Application No. 2017379402, dated Sep. 26, 2021.

Office Action from corresponding U.S. Appl. No. 18/522,962, dated Jan. 24, 2025.

* cited by examiner (a)

(b)

| Sample | Number of repeats | | 16:0 | 18:0 | 18:1 | 18:2 | 18:3 |
|---|---|---|---|---|---|---|---|
| FAD-2-7 | 1 | 1 | 7.8 | 2.6 | 83.0 | 2.1 | 4.6 |
| FAD-2-7 | 1 | 2 | 8.3 | 2.6 | 79.8 | 3.5 | 5.8 |
| FAD-2-7 | 1 | 3 | 8.4 | 2.6 | 78.6 | 3.8 | 6.5 |
| FAD-2-30 | 1 | 1 | 8.6 | 2.2 | 78.7 | 4.1 | 6.4 |
| FAD-2-30 | 1 | 2 | 8.1 | 2.0 | 80.1 | 2.7 | 7.1 |
| FAD-2-30 | 2 | 1 | 8.2 | 2.9 | 79.4 | 7.0 | 5.5 |
| FAD-2-30 | 2 | 2 | 8.2 | 2.9 | 82.6 | 1.8 | 4.5 |
| FAD-2-30 | 2 | 3 | 8.2 | 3.1 | 78.4 | 4.3 | 5.9 |
| FAD-2-30 | 3 | 1 | 8.1 | 3.0 | 80.9 | 2.5 | 5.5 |
| FAD-2-30 | 3 | 2 | 8.7 | 3.3 | 76.9 | 4.3 | 6.8 |
| FAD-2-30 | 5 | 1 | 8.4 | 3.2 | 79.1 | 3.3 | 6.0 |
| FAD-2-30 | 5 | 2 | 10.1 | 3.0 | 73.4 | 5.9 | 7.7 |
| FAD-2-30 | 5 | 3 | 8.8 | 2.9 | 74.4 | 6.0 | 7.9 |
| FAD-2-30 | 8 | 1 | 8.2 | 3.3 | 82.3 | 1.7 | 4.5 |
| FAD-2-30 | 8 | 2 | 7.6 | 3.1 | 83.3 | 1.6 | 4.3 |
| FAD-2-30 | 8 | 3 | 7.3 | 3.1 | 83.1 | 1.5 | 5.1 |
| FAD-2-30 | 9 | 1 | 8.0 | 3.1 | 80.1 | 3.9 | 4.9 |
| FAD-2-30 | 9 | 2 | 8.3 | 3.1 | 78.7 | 3.5 | 6.4 |
| FAD-2-30 | 9 | 3 | 7.8 | 3.8 | 82.4 | 1.6 | 4.5 |
| FAD-2-30 | 19 | 1 | 8.5 | 3.4 | 75.2 | 6.3 | 6.7 |
| FAD-2-30 | 19 | 2 | 8.5 | 2.9 | 75.5 | 6.1 | 7.1 |
| FAD-2-30 | 21 | 1 | 7.8 | 2.9 | 82.4 | 2.5 | 4.3 |
| FAD-2-30 | 21 | 2 | 9.2 | 3.0 | 70.9 | 7.5 | 9.4 |
| FAD-2-30 | 21 | 3 | 8.1 | 2.9 | 79.6 | 3.3 | 6.0 |
| Pungsan | | | 10.6 | 3.6 | 23.5 | 52.3 | 10.0 |
| Kwangan | | | 12.5 | 3.4 | 38.2 | 36.2 | 9.5 |
| Hosim | | | 7.8 | 2.6 | 80.5 | 3.8 | 5.5 |

FIG. 5

| GENE | Target sequence | Indel ratio (%) |
|---|---|---|
| FAD2A | GTGTTTGGAACCCTTGAGAGAGG | 99.20% |
| FAD2B | GTGTTTGGAACCCTTGAGAGAGG | 100% |

FIG. 6

| Chr10_FAD2-7 | Type |
|---|---|
| AAGGGAAGAAGCCTCTCTCAAGGGTTCCAAACACAAAGCCACCATT | WT |
| AAGGGAAGAAGCCTCTCT----GGGTTCCAAACACAAAGCCACCATT | -3 |
| AAGGGAAGAAGCCTC---------TTCCAAACACAAAGCCACCATT | -9 |
| AAGGGAAGAAGCCTC---------TCT---ACACAAAGCCACCATT | -12 |
| AAGGGAAGAAGCCTCTCT----GGTTCCAAACACAAAGCCACCATT | -4 |
| AAGG----------------GTTCCAAACACAAAGCCACCATT | -19 |
| AAGGGAAGAAGCCTC---------TCTCAAACACAAAGCCACCATT | -9 |
| AAGGGAAGAAGCCTCT-------GGTTCCAAACACAAAGCCACCATT | -6 |
| AAGGGAAGAAGCCTCTCT--AGGGTTCCAAACACAAAGCCACCATT | -2 |
| AAGGGAAGAAGCCTCTCTTCAAGGGTTCCAAACACAAAGCCACCATT | +1 |
| Chr20_FAD2-7 | Type |
| CAGCAGAAGAAGCCTCTCTCAAGGGTTCCAAACACAAAGCCACCATTCAC | WT |
| CAGCAGAAGAAGCCTCTCT----GGTTCCAAACACAAAGCCACCATTCAC | -4 |
| CAGCAGAAGAAGCCTCTC----GGGTTCCAAACACAAAGCCACCATTCAC | -4 |
| CAGCAGAAGAAGCCTCTC-------TTCCAAACACAAAGCCACCATTCAC | -7 |
| CAGCAGAAGAAGCCTCT-----AGGGTTCCAAACACAAAGCCACCATTCAC | -4 |
| CAGCAGAAGAAGCCTCTCTTTTTCAAGGGTTCCAAACACAAAGCCACCAT | +4 |
| CAGCAGAA-----------------AACACAAAGCCACCATTCAC | -22 |
| GGGAGGTGGAGGCCGTGTGG-------CCAAACACAAAGCCACCATTCAC | -7,+1 |
| CAGCAGAAGAAGCCTCTCT---------AACACAAAGCCACCATTCAC | -11 |
| CAGCAGAAGAAGCCTCTT-CAAGGGTTCCAAACACAAAGCCACCATTCAC | -1 |

FIG. 7

| Chr10 | More than minimum frequency | Insertions | Deletions | Indel frequency |
|---|---|---|---|---|
| FAD2-7#1-1 | 11252 | 0 | 95 | 95 (0.8%) |
| FAD2-30#2-4 | 13523 | 0 | 13410 | 13410 (99.2%) |
| FAD2-30#3-1 | 18132 | 0 | 70 | 70 (0.4%) |
| FAD2-30#3-2 | 14784 | 0 | 14771 | 14771 (99.9%) |
| FAD2-30#8-1 | 29358 | 0 | 29327 | 29327 (99.9%) |
| FAD2-30#8-2 | 28970 | 0 | 27798 | 27798 (96.0%) |
| FAD2-30#9-1 | 18012 | 11 | 9438 | 9449 (52.5%) |
| FAD2-30#19-1 | 21332 | 0 | 21317 | 21317 (99.9%) |
| FAD2-30#21-2 | 22833 | 0 | 22818 | 22818 (99.9%) |
| FAD2-30#21-5 | 26980 | 0 | 26981 | 26981 (100.0%) |
| FAD2-30#22-5 | 19492 | 0 | 19483 | 19483 (100.0%) |
| FAD2-30#22-6 | 26485 | 0 | 26454 | 26454 (99.9%) |

FIG. 8A

| Chr20 | More than minimum frequency | Insertions | Deletions | Indel frequency |
|---|---|---|---|---|
| FAD2-7#1-1 | 22943 | 0 | 22931 | 22931 (99.9%) |
| FAD2-30#2-4 | 23466 | 0 | 11463 | 11463 (48.8%) |
| FAD2-30#3-1 | 25145 | 0 | 73 | 73 (0.3%) |
| FAD2-30#3-2 | 25790 | 18 | 25742 | 25760 (99.9%) |
| FAD2-30#8-1 | 19141 | 22 | 19111 | 19133 (100.0%) |
| FAD2-30#8-2 | 26126 | 54 | 26063 | 26117 (100.0%) |
| FAD2-30#9-1 | 23439 | 23294 | 129 | 23423 (99.9%) |
| FAD2-30#19-1 | 15524 | 7 | 15511 | 15518 (100.0%) |
| FAD2-30#21-2 | 18724 | 5 | 18719 | 18724 (100.0%) |
| FAD2-30#21-5 | 23165 | 2 | 23163 | 23165 (100.0%) |
| FAD2-30#22-5 | 4582 | 2 | 4580 | 4582 (100.0%) |
| FAD2-30#22-6 | 3360 | 0 | 3360 | 3360 (100.0%) |

FIG. 8B

| Chr10 | Indel | Local Sequence |
|---|---|---|
| WT | | AAAGTGGAAGTTCAAGGGAAGAAGCCTCTCAAGGGTTCAAAACACAAAGCCACCATTCACTGTTGGCCAA |
| FAD2-7#1-1 | | AAAGTGGAAGTTCAAGGGAAGAAGCCTCTCAAGGGTTCAAAACACAAAGCCACCATTCACTGTTGGCCAA |
| FAD2-30#2-4 | -8 | AAAGTGGAAGTTCAAGGGAAGAAGCCTCTC--------TCCAAAACACAAAGCCACCATTCACTGTTGGCCAA |
| FAD2-30#2-4 | -5 | AAAGTGGAAGTTCAAGGGAAGAAGCCTCTC-----GTTCCAAAACACAAAGCCACCATTCACTGTTGGCCAA |
| FAD2-30#3-1 | | AAAGTGGAAGTTCAAGGGAAGAAGCCTCTCAAGGGTTCAAAACACAAAGCCACCATTCACTGTTGGCCAA |
| FAD2-30#3-2 | -6 | AAAGTGGAAGTTCAAGGGAAGAAGCCTCT------TTCCAAAACACAAAGCCACCATTCACTGTTGGCCAA |
| FAD2-30#3-2 | -2 | AAAGTGGAAGTTCAAGGGAAGAAGCCTCTCT--AGGGTTCCAAAACACAAAGCCACCATTCACTGTTGGCCAA |
| FAD2-30#8-1 | -7 | AAAGTGGAAGTTCAAGGGAAGAAGCCTC-------TTCCAAAACACAAAGCCACCATTCACTGTTGGCCAA |
| FAD2-30#8-1 | -2 | AAAGTGGAAGTTCAAGGGAAGAAGC--CTCTCAAGGGTTCCAAAACACAAAGCCACCATTCACTGTTGGCCAA |
| FAD2-30#8-2 | -7 | AAAGTGGAAGTTCAAGGGAAGAAGCCTCTC-------TTCCAAAACACAAAGCCACCATTCACTGTTGGCCAA |
| FAD2-30#8-2 | -5 | AAAGTGGAAGTTCAAGGGAAGAAGCCTCTC-----GTTCCAAAACACAAAGCCACCATTCACTGTTGGCCAA |
| FAD2-30#9-1 | -7 | AAAGTGGAAGTTCAAGGGAAGAAGCCTCTC-------TTCCAAAACACAAAGCCACCATTCACTGTTGGCCAA |
| FAD2-30#19-1 | -8 | AAAGTGGAAGTTCAAGGGAAGAAGCCTCTC--------TCCAAAACACAAAGCCACCATTCACTGTTGGCCAA |
| FAD2-30#19-1 | -7 | AAAGTGGAAGTTCAAGGGAAGAAGCCTCTC-------TTCCAAAACACAAAGCCACCATTCACTGTTGGCCAA |
| FAD2-30#21-2 | -7 | AAAGTGGAAGTTCAAGGGAAGAAGCCTCTC-------TTCCAAAACACAAAGCCACCATTCACTGTTGGCCAA |
| FAD2-30#21-5 | -2 | AAAGTGGAAGTTCAAGGGAAGAAGC--CTCTCAAGGGTTCCAAAACACAAAGSCACCATTCACTGTTGGCCAA |
| FAD2-30#22-5 | -2 | AAAGTGGAAGTTCAAGGGAAGAAGCCTCTCT--AGGGTTCCAAAACACAAAGCCACCATTCACTGTTGGCCAA |
| FAD2-30#22-6 | -2 | AAAGTGGAAGTTCAAGGGAAGAAGCCTCTCT--AGGGTTCCAAAACACAAAGCCACCATTCACTGTTGGCCAA |

FIG. 9A

| Chr20 | Indel | Local Sequence |
|---|---|---|
| WT | | CAGAAGAAGCCCTCTTCAAGGGTTCCAAACACAAAGCCACCATTCACTGTTGGCCAA |
| FAD2-7#1-1 | -4 | CAGAAGAAGCCCTC----GGGTTCCAAACACAAAGCCACCATTCACTGTTGGCCAA |
| | -4 | CAGAAGAAGCCCTCT----GGTTCCAAACACAAAGCCACCATTCACTGTTGGCCAA |
| FAD2-30#2-4 | -8 | CAGAAGAAGCCCTCTTCAAGGTTCCAAACACAAAGCCACCATTCACTGTTGGCCAA |
| | | CAGAAGAAGCCCTC--------TCCAAACACAAAGCCACCATTCACTGTTGGCCAA |
| FAD2-30#3-1 | | CAGAAGAAGCCCTCTTCAAGGGTTCCAAACACAAAGCCACCATTCACTGTTGGCCAA |
| FAD2-30#3-2 | -2 | CAGAAGAAGCCCTCT--AGGGTTCCAAACACAAAGCCACCATTCACTGTTGGCCAA |
| FAD2-30#8-1 | -2 | CAGAAGAAGCCCTCT--AGGGTTCCAAACACAAAGCCACCATTCACTGTTGGCCAA |
| FAD2-30#8-2 | -2 | CAGAAGAAGCCCTCT--AGGGTTCCAAACACAAAGCCACCATTCACTGTTGGCCAA |
| FAD2-30#9-1 | +1 | CAGAAGAAGCCCTCTTCAAGGGTTCCAAACACAAAGCCACCATTCACTGTTGGCCAA |
| FAD2-30#19-1 | -3 | CAGAAGAAGCCCTC---GGGTTCCAAACACAAAGCCACCATTCACTGTTGGCCAA |
| FAD2-30#21-2 | -7 | CAGAAGAAGCCCTC-------TCCAAACACAAAGCCACCATTCACTGTTGGCCAA |
| | -2 | CAGAAGAAGCCCTCT--AGGGTTCCAAACACAAAGCCACCATTCACTGTTGGCCAA |
| FAD2-30#21-5 | -11 | CAGAAGAAGCCCTCT-----------AACACAAAGCCACCATTCACTGTTGGCCAA |
| FAD2-30#22-5 | -10 | CAGAAGAAGCCCTC----------TCCAAACACAAAGCCACCATTCACTGTTGGCCAA |
| FAD2-30#22-6 | -11 | CAGAAGAAGCCCTCT-----------AACACAAAGCCACCATTCACTGTTGGCCAA |

FIG. 9B

OLEIC ACID-ENRICHED PLANT BODY HAVING GENETICALLY MODIFIED FAD2 AND PRODUCTION METHOD THEREOF

CROSS-REFERENCE TO RELATED APPLICATIONS

This application is a divisional application of U.S. patent application Ser. No. 16/471,443, filed on Jun. 19, 2019, which is a national phase application of PCT Application No. PCT/KR2017/010576, filed on Sep. 26, 2017, which claims the benefit of and priority to U.S. Provisional Patent Application No. 62/438,018, filed Dec. 22, 2016. The entire disclosures of the applications identified in this paragraph are incorporated herein by references.

FIELD

The present invention relates to the manipulation or modification of a FAD2 gene using a CRISPR-Cas system to increase the content of oleic acid in a plant body, and more particularly, to a plant body increased in oleic acid content by modifying a FAD2 gene using a CRISPR-Cas system capable of targeting a corresponding gene, a manipulation composition capable of manipulating a FAD2 gene, and a method using the same.

BACKGROUND

Soybean oil is the second most consumed edible oil in the world due to being rich in essential fatty acids and the high utilization of soybean oil meal as a by-product, and 45 million tons thereof are produced annually. About 62% of the fatty acids constituting soybean oil are polyunsaturated fatty acids (PUFAs), and 54% of the fatty acids are linoleic acid, and 8% of the fatty acids are linolenic acid. Since the fatty acids have two or more double bonds, oxidation easily occurs and the oil easily becomes rancid, such that it is difficult to be stored and distributed. (It has a low storage and difficulty in distributions.) Therefore, to manufacture soybean oil with a stable quality to be used in food processing or cooking, pretreatment and purification processes are required. Most soybean oil manufacturers maintain a certain level of quality by preventing rancidity by treating partial hydrogenation for adding a hydrogen to an unsaturated double bond where oxidation easily occurs during a manufacturing process.

However, partial hydrogenation has a disadvantage of producing trans-fatty acids having a risk in a process of saturating the double bond of unsaturated fatty acids with hydrogens. While, in the natural state, the production of cis-fatty acids is dominant in oxidation, however, since trans-forms are thermodynamically stable, trans-fatty acids, which are geometric isomers that do not naturally occur, are produced in hydrogenation or processing.

Due to the controversy over the risk of trans fat, in 2015, the US FDA decided to eliminate that partially-hydrogenated oil that is widely used in the process of manufacturing processed food from the Generally Recognized as Safe (GRAS) list. Accordingly, US food manufacturers are looking for different edible oils whereby they can replace, and stop using partially-hydrogenated oils by 2018, and the related industry is expected to spend 6 billion US dollars to establish an alternative edible oil or a new manufacturing process. Partially-hydrogenated soybean oil is expected to be decreased in demand by 9 million tons annually only in the US according to the FDA action.

In addition, many countries such as Europe, Korea and Japan as well as the US are well aware of the risk of trans fatty acids, and with the trend to encourage people not to eat as much as possible, globally, regulations on partially hydrogenated oil seem to be more strengthened in the future. Therefore, there is a need of developing edible oil products that do not contain trans fatty acids that can replace soybean oil produced by partial hydrogenation.

SUMMARY

Technical Problems

To solve the above-described problems, the present invention relates to an artificially manipulated unsaturated fatty acid controlling system, which has an effect of increasing the content of a specific unsaturated fatty acid. More particularly, the present invention relates to an artificially manipulated unsaturated fatty acid biosynthesis-associated factor, and a system for controlling an unsaturated fatty acid, which artificially modifies the content of a specific unsaturated fatty acid.

The present invention is directed to providing a plant body increased in the content of a specific unsaturated fatty acid due to an artificially manipulated unsaturated fatty acid biosynthesis-associated factor.

The present invention is directed to providing a plant body decreased in the content of a specific unsaturated fatty acid by an artificially manipulated unsaturated fatty acid biosynthesis-associated factor.

As an exemplary embodiment of the present invention, the present invention provides an artificially manipulated unsaturated fatty acid biosynthesis-associated factor.

As an exemplary embodiment of the present invention, the present invention provides an artificially manipulated unsaturated fatty acid controlling system.

As an exemplary embodiment of the present invention, the present invention provides an artificially manipulated unsaturated fatty acid biosynthesis-associated factor and an expression product thereof.

As an exemplary embodiment of the present invention, the present invention provides a composition for manipulating a gene to manipulate an unsaturated fatty acid biosynthesis-associated factor and a method using the same.

As an exemplary embodiment of the present invention, the present invention provides a method of controlling the biosynthesis of an unsaturated fatty acid.

As an exemplary embodiment of the present invention, the present invention provides a method of controlling the type of an unsaturated fatty acid and the content thereof.

As an exemplary embodiment of the present invention, the present invention provides a composition for controlling an unsaturated fatty acid to control the biosynthesis of an unsaturated fatty acid and/or the content of the unsaturated fatty acid, and various uses thereof.

As an exemplary embodiment of the present invention, the present invention provides an artificially manipulated unsaturated fatty acid biosynthesis-associated factor such as FAD2, FAD3, FAD4, FADE, FAD7 or FAD8 and/or an expression product thereof.

As an exemplary embodiment of the present invention, the present invention provides a composition for manipulating a gene to artificially manipulate an unsaturated fatty acid biosynthesis-associated factor such as FAD2, FAD3, FAD4, FAD6, FAD7 or FAD8.

As an exemplary embodiment of the present invention, the present invention provides an artificially manipulated unsaturated fatty acid biosynthesis-associated factor such as FAD2, FAD3, FAD4, FAD6, FAD7 or FAD8 and/or various uses of the composition for manipulating a gene for artificial manipulation.

As an exemplary embodiment of the present invention, the present invention provides a plant body increased or decreased in the content of a specific unsaturated fatty acid and a processed product using the same.

Technical Solutions

To solve these problems, the present invention provides a system capable of artificially controlling the biosynthesis of an unsaturated fatty acid and/or the content of the fatty acids, which includes an artificially manipulated unsaturated fatty acid biosynthesis-associated factor and/or a composition capable of artificially manipulating the unsaturated fatty acid biosynthesis-associated factor, for controlling the content of a specific unsaturated fatty acid.

In one exemplary embodiment, the present invention provides a plant body increased in the content of a specific unsaturated fatty acid by an artificially manipulated unsaturated fatty acid biosynthesis-associated factor.

In another exemplary embodiment, the present invention provides a specific unsaturated fatty acid obtained from a plant body by using an artificially manipulated unsaturated fatty acid biosynthesis-associated factor.

The term "specific unsaturated fatty acid" used herein refers to one or more unsaturated fatty acids selected from various types of known unsaturated fatty acids, it may be one or more unsaturated fatty acids selected from the classification system represented by the number of carbons (C) and the number of double bonds (D), which are included in an unsaturated fatty acid among various types of unsaturated fatty acids. The term "CN:DM unsaturated fatty acid" used herein refers to an unsaturated fatty acid consisting of N number of carbons (C) and including M number of double bonds (D). Here, N may be an integer of 4 to 36, and M may be an integer of 1 to 35.

The specific unsaturated fatty acid may be a C8~24:D1 unsaturated fatty acid.

The specific unsaturated fatty acid may be a C16~22:D1 unsaturated fatty acid.

The specific unsaturated fatty acid may be a C18:D1 unsaturated fatty acid.

The specific unsaturated fatty acid may be oleic acid, elaidic acid or vaccenic acid.

In addition, the specific unsaturated fatty acid may be a C8~24:D2 unsaturated fatty acid.

The specific unsaturated fatty acid may be a C16~22:D2 unsaturated fatty acid.

The specific unsaturated fatty acid may be a C18:D2 unsaturated fatty acid.

The specific unsaturated fatty acid may be linoleic acid or linoelaidic acid.

In one exemplary embodiment of the present invention, the present invention provides an artificially manipulated unsaturated fatty acid biosynthesis-associated factor.

The term "unsaturated fatty acid biosynthesis-associated factor" used herein refers to all factors directly participating in or indirectly affecting the biosynthesis of an unsaturated fatty acid. Here, the factor may be DNA, RNA, a gene, a peptide, a polypeptide or a protein. The factor includes various materials capable of controlling the biosynthesis of an unsaturated fatty acid, which are non-natural, that is, artificially manipulated. For example, the factor may be a genetically manipulated or modified gene or protein, which is expressed in a plant.

The unsaturated fatty acid biosynthesis-associated factor may increase the content of a specific unsaturated fatty acid included in a plant.

The unsaturated fatty acid biosynthesis-associated factor may decrease the content of a specific unsaturated fatty acid included in a plant.

The unsaturated fatty acid biosynthesis-associated factor may affect a direct/indirect mechanism for controlling the content of a specific unsaturated fatty acid included in a plant.

In one exemplary embodiment of the present invention, the unsaturated fatty acid biosynthesis-associated factor may be, for example, an artificially manipulated a FAD2 gene, a FAD3 gene, a FAD4 gene, a FAD6 gene, a FAD7 gene or a FAD8 gene, preferably a FAD2 gene or a FAD3 gene.

In one exemplary embodiment of the present invention, the unsaturated fatty acid biosynthesis-associated factor may include two or more artificially manipulated genes. For example, two or more genes selected from the group consisting of a FAD2 gene, a FAD3 gene, a FAD4 gene, a FAD6 gene, a FAD7 gene and a FAD8 gene may be artificially manipulated.

Therefore, in an exemplary embodiment of the present invention, one or more artificially manipulated unsaturated fatty acid biosynthesis-associated factors selected from the group consisting of a FAD2 gene, a FAD3 gene, a FAD4 gene, a FAD6 gene, a FAD7 gene and a FAD8 gene, which have undergone modification in a nucleic acid sequence, are provided.

The modification in a nucleic acid sequence may be non-limitedly, artificially manipulated by a guide nucleic acid-editor protein complex.

The term "guide nucleic acid-editor protein complex" refers to a complex formed through the interaction between a guide nucleic acid and an editor protein, and the nucleic acid-protein complex includes the guide nucleic acid and the editor protein.

The guide nucleic acid-editor protein complex may serve to modify a subject.

The subject may be a target nucleic acid, a gene, a chromosome or a protein.

For example, the gene may be an unsaturated fatty acid biosynthesis-associated factor, artificially manipulated by a guide nucleic acid-editor protein complex,
  wherein the unsaturated fatty acid biosynthesis-associated factor artificially manipulated includes one or more modifications of nucleic acids which is
  at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the unsaturated fatty acid biosynthesis-associated factor or in a continuous 1 bp to 50 bp the base sequence region adjacent to the 5' end and/or 3' end thereof, or
  a chemical modification of one or more nucleotides in a nucleic acid sequence constituting the unsaturated fatty acid biosynthesis-associated factor.

The modification of nucleic acids may occur in a promoter region of the gene.

The modification of nucleic acids may occur in an exon region of the gene. In one exemplary embodiment, 50% of the modifications may occur in the upstream section of the coding regions of the gene.

The modification of nucleic acids may occur in an intron region of the gene.

The modification of nucleic acids may occur in an enhancer region of the gene.

The PAM sequence may be, for example, one or more of the following sequences (described in the 5' to 3' direction):
  NGG (N is A, T, C or G);
  NNNNRYAC (each of N is independently A, T, C or G, R is A or G, and Y is C or T);
  NNAGAAW (each of N is independently A, T, C or G, and W is A or T);
  NNNNGATT (each of N is independently A, T, C or G);
  NNGRR(T) (each of N is independently A, T, C or G, and R is A or G); and
  TTN (N is A, T, C or G).

The editor protein may be derived from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.*

In one exemplary embodiment, the editor protein may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein, and a Cpf1 protein. As an example, the editor protein may be a *Streptococcus pyogenes*-derived Cas9 protein or a *Campylobacter jejuni*-derived Cas9 protein.

In addition, in another embodiment, the present invention provides a guide nucleic acid, which is capable of forming a complementary bond with respect to target sequences of SEQ ID NOs: 1 to 30, for example, SEQ ID NOs:7 or 30.

The guide nucleic acid may form a complementary bond with a part of nucleic acid sequences of a FAD2 gene. It may create 0 to 5, 0 to 4, 0 to 3, or 0 to 2 mismatches. As a preferable example, the guide nucleic acid may be nucleotides forming a complementary bond with one or more of the target sequences of SEQ ID NOs: 1 to 30, for example, SEQ ID NOs: 7 or 30, respectively.

The guide nucleic acid may be non-limitedly 18 to 25 bp, 18 to 24 bp, 18 to 23 bp, 19 to 23 bp, or 20 to 23 bp nucleotides.

In addition, the present invention provides a composition for gene manipulation, which may be employed in artificial manipulation of an unsaturated fatty acid biosynthesis-associated factor for a specific purpose.

The composition for gene manipulation may include a guide nucleic acid-editor protein complex or a nucleic acid sequence encoding the same.

The composition for gene manipulation may include:
(a) a guide nucleic acid capable of forming a complementary bond with respect to each of target sequences of one or more genes selected from the group consisting of a FAD2 gene, a FAD3 gene, a FAD4 gene, a FAD6 gene, a FAD7 gene and a FAD8 gene, respectively or a nucleic acid sequence encoding the guide nucleic acid;
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein, and a Cpf1 protein or a nucleic acid sequence encoding the same.

In one exemplary embodiment, the guide nucleic acid may be a nucleic acid sequence which forms a complementary bond with respect to one or more of the target sequences of SEQ ID NOs: 1 to 30, respectively.

For example, the guide nucleic acid may be a nucleic acid sequence which forms a complementary bond with the target sequence of SEQ ID NOs: 7 or 30.

In one exemplary embodiment, the composition for gene manipulation may be a viral vector system.

The viral vector may be an *Agrobacterium* vector system using an agrobacteria.

In one exemplary embodiment, the composition for gene manipulation may be a viral vector system.

The viral vector may include one or more selected from the group consisting of a mosaic virus, a retrovirus, a lentivirus, an adenovirus, an adeno-associated virus (AAV), a vaccinia virus, a poxvirus and a herpes simplex virus.

In an exemplary embodiment, the present invention provides a method for artificially manipulating cells, which includes: introducing (a) a guide nucleic acid which is capable of forming a complementary bond with respect to the target sequences of one or more genes selected from the group consisting of a FAD2 gene, a FAD3 gene, a FAD4 gene, a FAD6 gene, a FAD7 gene and a FAD8 gene, respectively, or a nucleic acid sequence encoding the same; and
(b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein, and a Cpf1 protein, respectively, or a nucleic acid sequence encoding the same to cells.

The guide nucleic acid and the editor protein may be present in one or more vectors in the form of a nucleic acid sequence, or may be present in a complex formed by coupling the guide nucleic acid with the editor protein.

The introduction may be performed in vivo or ex vivo of a plant.

The introduction may be performed by one or more methods selected from a gene gun, an electroporation, liposomes, plasmids, *Agrobacterium* vector system, viral vectors, nanoparticles and a protein translocation domain (PTD) fusion protein method.

The viral vector may include one or more selected from the group consisting of a mosaic virus, a retrovirus, a lentivirus, an adenovirus, an adeno-associated virus (AAV), a vaccinia virus, a poxvirus and a herpes simplex virus.

In addition, the present invention provides a composition for controlling an unsaturated fatty acid to control the biosynthesis of an unsaturated fatty acid and/or the content of the unsaturated fatty acid of a plant.

The composition for controlling an unsaturated fatty acid may include a composition for gene manipulation, which may be employed in artificial manipulation of an unsaturated fatty acid biosynthesis-associated factor.

The formulation of the composition for gene manipulation is the same as described above.

In an exemplary embodiment, the present invention provides a processed product using a plant body increased or decreased in the content of a specific unsaturated fatty acid.

The plant body may include an artificially manipulated unsaturated fatty acid biosynthesis-associated factor.

The processed product may be a food which can be ingested by humans and/or animals.

In an exemplary embodiment, the present invention provides a kit for gene manipulation to control the content of a specific unsaturated fatty acid.

The kit may include a composition for gene manipulation, which may be employed in artificial manipulation of an unsaturated fatty acid biosynthesis-associated factor.

The gene of interest may be artificially manipulated using such a kit.

Advantageous Effects

A plant body increased in the content of a specific unsaturated fatty acid which is good for human health or decreased in the content of a specific unsaturated fatty acid which is harmful for human health, and/or a processed product using the same can be manufactured by using an artificially manipulated unsaturated fatty acid biosynthesis-associated factor and a system for controlling an unsaturated fatty acid, which is artificially modified thereby.

For example, one or more genes selected from a FAD2 gene, a FAD3 gene, a FAD4 gene, a FAD6 gene, a FAD7 gene and a FAD8 gene can be used.

BRIEF DESCRIPTION OF DRAWINGS

FIG. 5 shows the contents of oleic acid in $T_1$ seeds of pPZP-FAD2-7 and pPZP-FAD2-30.

FIG. 6 shows the indel frequency of an FAD2 gene targeted by CRISPR-Cas9 (the target sequence of FAD2A gene is SEQ ID NO: 7, and the target sequence of FAD2B is SEQ ID NO: 7).

FIG. 7 shows the sequencing results for an FAD2 gene of soybeans transformed using CRISPR-Cas9 (a target sequence including PAM shown with an underline). For targeting FAD2, the target site (Type WT) located in the chromosome #10 is SEQ ID NO: 71, and the target site (Type WT) located in the chromosome #20 is SEQ ID NO: 72. Herein, the target site includes the target sequence. The sequencing results for the FAD2 gene located in the chromosome #10 are shown in SEQ ID NO: 75 to 83 (Type −3 to +1 order). The sequencing results for the FAD2 gene located in the chromosome #20 are shown in SEQ ID NO: 84 to 92 (Type −4 to −1 order).

FIGS. 8A and 8B shows the results of target site screening and indel frequency of an FAD2 gene manipulated in $T_1$ transformants, shows the results of target site screening and indel frequency for of an FAD2 gene in (a) Chromosome #10 (chr10), and (b) Chromosome #20 (chr20).

FIGS. 9A and 9B shows the target site sequencing results of an FAD2 gene manipulated in $T_1$ transformants, shows the target site sequencing results of an FAD2 gene in (a) Chromosome #10 (chr10), and (b) Chromosome #20 (chr20). For targeting FAD2, the target site located in the chromosome #10 is SEQ ID NO: 73, and the target site located in the chromosome #20 is SEQ ID NO: 74. The target site sequencing results of the FAD2 located in the chromosome #10 are shown in the following SEQ ID NOs according to samples: SEQ ID NO: 73 (FAD2-7 #1-1 having no indel); SEQ ID NO:93, 94 (FAD2-30 #2-4); SEQ ID NO: 73 (FAD2-30 #3-1 having no indel); SEQ ID NO: 95, 96 (FAD2-30 #3-2); SEQ ID NO: 97 (FAD2-30 #8-1); SEQ ID NO: 98 to 100 (FAD2-30 #8-2); SEQ ID NO: 101 (FAD2-30 #9-1), SEQ ID NO: 73 (FAD2-30 #9-1 having no indel); SEQ ID NO: 102, 103 (FAD2-30 #19-1); SEQ ID NO: 104 (FAD2-30 #21-2); SEQ ID NO: 105 (FAD2-30 #21-5); SEQ ID NO: 106 (FAD2-30 #22-5); SEQ ID NO: 107 (FAD2-30 #22-6). The target site sequencing results of the FAD2 located in the chromosome #20 are shown in the following SEQ ID NOs according to samples: SEQ ID NO: 108, 109 (FAD2-7 #1-1); SEQ ID NO: 74 (FAD2-30 #2-4 having no indel), SEQ ID NO: 110 (FAD2-30 #2-4); SEQ ID NO: 74 (FAD2-30 #3-1 having no indel); SEQ ID NO: 111 (FAD2-30 #3-2); SEQ ID NO: 112 (FAD2-30 #8-1); SEQ ID NO: 113 (FAD2-30 #8-2); SEQ ID NO: 114 (FAD2-30 #9-1); SEQ ID NO: 115 (FAD2-30 #19-1); SEQ ID NO: 116, 117 (FAD2-30 #21-2); SEQ ID NO: 118 (FAD2-30 #21-5); SEQ ID NO: 119 (FAD2-30 #22-5); SEQ ID NO: 120 (FAD2-30 #22-6).

DETAILED DESCRIPTION

Figure 1:
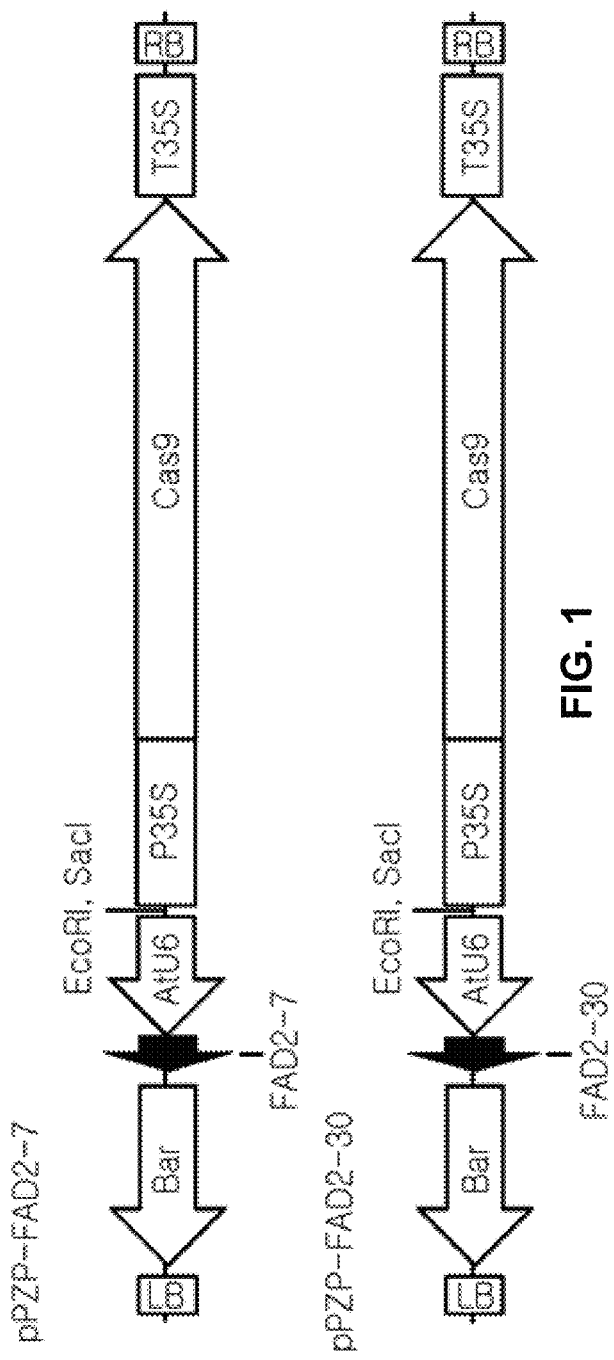
FIG. 1 is a schematic diagram of CRISPR-Cas9 vectors, pPZP-FAD2-7 and pPZP-FAD2-30, for modifying a FAD2 gene of soybeans.

Unless defined otherwise, all technical and scientific terms used herein have the same meanings as commonly understood by those of ordinary skill in the art to which the present invention belongs. Although methods and materials similar to or the same as described in the specification can be used in the implementation or experiments of the present invention, suitable methods and materials will be described below. All publications, patent applications, patents and other references mentioned herein are incorporated by reference in their entirety. In addition, the materials, methods and embodiments are merely illustrative, and not intended to be limitative.

One aspect of the present invention relates to a transgenic plant body increased in the content of a C8~24:D1 unsaturated fatty acid.

Specifically, the present invention relates to a transgenic plant body increased in the content of a specific unsaturated fatty acid by artificially manipulating an unsaturated fatty acid biosynthesis-associated factor, the present invention includes an unsaturated fatty acid biosynthesis-associated factor in which a function is artificially changed, an artificial manipulation composition therefor, a method of preparing the same, and a plant body including the same.

Another aspect of the present invention relates to a transgenic plant body decreased in the content of a C8~24:D2 unsaturated fatty acid.

Specifically, the present invention relates to a transgenic plant body decreased in the content of a specific unsaturated fatty acid by artificially manipulating an unsaturated fatty acid biosynthesis-associated factor, the present invention includes an unsaturated fatty acid biosynthesis-associated factor in which a function is artificially changed, an artificial manipulation composition therefor, a method of preparing the same, and a plant body including the same.

Unsaturated Fatty Acid

One aspect of the present invention is a system for changing the content of fatty acids.

In one example, a system for changing the content of a specific saturated fatty acid in a plant body may be provided.

In another example, a system for changing the content of a specific unsaturated fatty acid in a plant body may be provided.

The term "fatty acid" used herein refers to a carboxylic acid having an aliphatic chain, and most fatty acids produced in a natural state have an even number of carbons ranging from about 4 to 36, which forms a carbon chain. Fatty acids are largely classified into saturated fatty acids and unsaturated fatty acids according to the type of a carbon bond.

The term "saturated fatty acid" used herein refers to fatty acids formed with a single bond.

Fatty acids include propionic acid, butyric acid, valeric acid, caproic acid, enanthic acid, caprylic acid, pelargonic acid, capric acid, lauric acid, myristic acid, palmitic acid, stearic acid, arachidic acid, behenic acid, lignoceric acid, cerotic acid and the like.

The term "unsaturated fatty acids" used herein refers to fatty acids having one or more carbon-carbon double bonds. The unsaturated fatty acids include all of cis-unsaturated fatty acids and trans-unsaturated fatty acids. The cis-unsaturated fatty acids refer to unsaturated fatty acids in which two hydrogens respectively binding to two carbons participating in a double bond are structurally placed in the same direction. On the other hand, the trans-unsaturated fatty acids refer to unsaturated fatty acids in which two hydrogens respectively binding to two carbons participating in a double bond are structurally placed in different directions.

The unsaturated fatty acids may be classified into Omega-3, 6, 7 and 9 according to the position of a carbon participating in a double bond.

The unsaturated fatty acids include Omega-3 ($\omega$-3) fatty acids.

Here, the "omega-3 ($\omega$-3) fatty acids" refers to an unsaturated fatty acid in which a double bond starts from the third carbon at the end of the carbon chain, and includes alpha-linolenic acid (ALA), eicosapentaenoic acid (EPA) and docosahexaenoic acid (DHA).

The unsaturated fatty acids include omega-6 ($\omega$-6) fatty acids.

Here, the "omega-6 ($\omega$-6) fatty acids" refers to unsaturated fatty acids in which a double bond starts from the sixth carbon at the end of a carbon chain, and includes linoleic acid (LA), gamma-linolenic acid (GLA), dihomo-gamma-linolenic acid (DGLA) and arachidonic acid (AA).

The unsaturated fatty acids include omega-7 ($\omega$-7) fatty acids.

Here, the "omega-7 ($\omega$-7) fatty acids" refers to unsaturated fatty acids in which a double bond starts from the seventh carbon at the end of a carbon chain, and includes paullinic acid, palmitoleic acid or vaccenic acid.

The unsaturated fatty acids include omega-9 ($\omega$-9) fatty acids.

Here, the "omega-9 ($\omega$-9) fatty acids" refers to unsaturated fatty acids in which a double bond starts from the ninth carbon at the end of a carbon chain, and includes oleic acid, elaidic acid, eicosenoic acid, erucic acid and nervonic acid.

In one exemplary embodiment, the unsaturated fatty acid may be an omega-6 ($\omega$-6) fatty acid.

In another exemplary embodiment, the unsaturated fatty acid may be an omega-9 ($\omega$-9) fatty acid.

In addition, the unsaturated fatty acid may be classified as a CN:DN unsaturated fatty acid by representing the number of carbons and the number of double bonds.

The term "CN:DM unsaturated fatty acid" refers to an unsaturated fatty acid consisting of N number of carbons (C) and including M number of double bonds (D). Here, N may be an integer of 4 to 36, and M may be an integer of 1 to 35.

For example, the unsaturated fatty acid consisting of 18 carbons and including 2 double bonds may be classified by being represented as a C18:D2 unsaturated fatty acid.

In one exemplary embodiment, the unsaturated fatty acid includes a CN:D1 unsaturated fatty acid.

Here, N may be an integer of 4 to 36.

Preferably, the CN:D1 unsaturated fatty acid may be a C8:D1 unsaturated fatty acid, a C10:D1 unsaturated fatty acid, a C12:D1 unsaturated fatty acid, a C14:D1 unsaturated fatty acid, a C16:D1 unsaturated fatty acid, a C18:D1 unsaturated fatty acid, a C20:D1 unsaturated fatty acid, a C22:D1 unsaturated fatty acid or a C24:D1 unsaturated fatty acid.

In another exemplary embodiment, the unsaturated fatty acid includes a CN:D2 unsaturated fatty acid.

Here, N may be an integer of 4 to 36.

Preferably, the CN:D2 unsaturated fatty acid may be a C8:D2 unsaturated fatty acid, a C10:D2 unsaturated fatty acid, a C12:D2 unsaturated fatty acid, a C14:D2 unsaturated fatty acid, a C16:D2 unsaturated fatty acid, a C18:D2 unsaturated fatty acid, a C20:D2 unsaturated fatty acid, a C22:D2 unsaturated fatty acid or a C24:D2 unsaturated fatty acid.

In still another exemplary embodiment, the unsaturated fatty acid includes a CN:D3 unsaturated fatty acid.

Here, N may be an integer of 4 to 36.

Preferably, the CN:D3 unsaturated fatty acid may be a C8:D3 unsaturated fatty acid, a C10:D3 unsaturated fatty acid, a C12:D3 unsaturated fatty acid, a C14:D3 unsaturated fatty acid, a C16:D3 unsaturated fatty acid, a C18:D3 unsaturated fatty acid, a C20:D3 unsaturated fatty acid, a C22:D3 unsaturated fatty acid or a C24:D3 unsaturated fatty acid.

In yet another exemplary embodiment, the unsaturated fatty acid includes a CN:D4 unsaturated fatty acid.

Here, N may be an integer of 4 to 36.

Preferably, the CN:D4 unsaturated fatty acid may be a C8:D4 unsaturated fatty acid, a C10:D4 unsaturated fatty acid, a C12:D4 unsaturated fatty acid, a C14:D4 unsaturated fatty acid, a C16:D4 unsaturated fatty acid, a C18:D4 unsaturated fatty acid, a C20:D4 unsaturated fatty acid, a C22:D4 unsaturated fatty acid or a C24:D4 unsaturated fatty acid.

In yet another exemplary embodiment, the unsaturated fatty acid includes a CN:D5 unsaturated fatty acid.

Here, N may be an integer of 4 to 36.

Preferably, the CN:D5 unsaturated fatty acid may be a C8:D5 unsaturated fatty acid, a C10:D5 unsaturated fatty acid, a C12:D5 unsaturated fatty acid, a C14:D5 unsaturated fatty acid, a C16:D5 unsaturated fatty acid, a C18:D5 unsaturated fatty acid, a C20:D5 unsaturated fatty acid, a C22:D5 unsaturated fatty acid or a C24:D5 unsaturated fatty acid.

In yet another exemplary embodiment, the unsaturated fatty acid includes a CN:D6 unsaturated fatty acid.

Here, N may be an integer of 4 to 36.

Preferably, the CN:D6 unsaturated fatty acid may be a C8:D6 unsaturated fatty acid, a C10:D6 unsaturated fatty acid, a C12:D6 unsaturated fatty acid, a C14:D6 unsaturated fatty acid, a C16:D6 unsaturated fatty acid, a C18:D6 unsaturated fatty acid, a C20:D6 unsaturated fatty acid, a C22:D6 unsaturated fatty acid or a C24:D6 unsaturated fatty acid.

In yet another exemplary embodiment, the unsaturated fatty acid includes a CN:DK unsaturated fatty acid.

Here, N may be an integer of 4 to 36, and K may be an integer of 7 to 35.

In one exemplary embodiment, the unsaturated fatty acid may be a C8 to 24:D1 unsaturated fatty acid.

Preferably, the unsaturated fatty acid may be selected from the group consisting of a C16:D1 unsaturated fatty acid, a C18:D1 unsaturated fatty acid, a C20:D1 unsaturated fatty acid and a C22:D1 unsaturated fatty acid.

Most preferably, the unsaturated fatty acid may be a C18:D1 unsaturated fatty acid or a C20:D1 unsaturated fatty acid.

In another exemplary embodiment, the unsaturated fatty acid may be a C8 to 24:D2 unsaturated fatty acid.

Preferably, the unsaturated fatty acid may be selected from the group consisting of a C16:D2 unsaturated fatty acid, a C18:D2 unsaturated fatty acid, a C20:D2 unsaturated fatty acid and a C22:D2 unsaturated fatty acid.

Most preferably, the unsaturated fatty acid may be a C18:D2 unsaturated fatty acid or a C20:D2 unsaturated fatty acid.

Unsaturated Fatty Acid Biosynthesis-Associated Factor

Unsaturated Fatty Acid Biosynthesis-Associated Factor

Another aspect of the present invention is an artificially manipulated or modified unsaturated fatty acid biosynthesis-associated factor.

The term "unsaturated fatty acid biosynthesis-associated factor" used herein refers to all factors directly participating in or indirectly affecting the biosynthesis of an unsaturated fatty acid. Here, the factor may be DNA, RNA, a gene, a peptide, a polypeptide or a protein.

In an exemplary embodiment, the unsaturated fatty acid biosynthesis-associated factor includes various materials capable of controlling the biosynthesis of an unsaturated fatty acid, which are non-natural, that is, artificially manipulated. For example, the unsaturated fatty acid biosynthesis-associated factor may be a genetically manipulated or modified gene or protein, which is expressed in a plant.

The term "artificially manipulated" means an artificially modified state, which is not a naturally occurring state.

The term "genetically manipulated" means that a genetic modification is artificially introduced to plant-derived substances cited in the present invention, and may be, for example, genes and gene products (polypeptides, proteins, etc.) in which their genomes are artificially modified for a specific purpose.

As an preferable example, the present invention provides a unsaturated fatty acid biosynthesis-associated factor which is genetically manipulated or modified for a specific purpose.

Genes or proteins having the functions listed below may have multiple types of functions, not only one type of unsaturated fatty acid biosynthesis-associated function. In addition, as needed, two or more unsaturated fatty acid biosynthesis-associated functions and factors may be provided.

An unsaturated fatty acid biosynthesis-associated factor may produce an unsaturated fatty acid by forming one or more double bonds in a saturated fatty acid.

The unsaturated fatty acid biosynthesis-associated factor may form new one or more double bonds in an unsaturated fatty acid.

The unsaturated fatty acid biosynthesis-associated factor may change a position of one or more double bonds included in an unsaturated fatty acid.

The unsaturated fatty acid biosynthesis-associated factor may remove one or more double bonds of an unsaturated fatty acid having two or more double bonds.

The unsaturated fatty acid biosynthesis-associated factor may change a cis-unsaturated fatty acid into a trans-unsaturated fatty acid.

The unsaturated fatty acid biosynthesis-associated factor may change a trans-unsaturated fatty acid into a cis-unsaturated fatty acid.

The unsaturated fatty acid biosynthesis-associated factor may control the content of an unsaturated fatty acid included in a plant.

The unsaturated fatty acid biosynthesis-associated factor may increase the content of a specific unsaturated fatty acid included in a plant.

The unsaturated fatty acid biosynthesis-associated factor may decrease the content of a specific unsaturated fatty acid included in a plant.

In an Exemplary Embodiment, the Unsaturated Fatty Acid Biosynthesis-Associated Factor May be an Unsaturated Fatty Acid Biosynthesis-Associated Factor of a Plant.

Preferably, the unsaturated fatty acid biosynthesis-associated factor may be a FAD gene or FAD protein.

Most preferably, the unsaturated fatty acid biosynthesis-associated factor may be one or more selected from the group consisting of FAD2, FAD3, FADE, FAD7 and FAD8.

In any exemplary embodiment, the unsaturated fatty acid biosynthesis-associated factor may be FAD2.

A FAD2 (omega-6 fatty acid desaturase) gene refers to a gene (full-length DNA, cDNA or mRNA) encoding the FAD2 protein also referred to as FAD2-1, FAD2-1B or GMFAD2-1B. In one example, the FAD2 gene may be one or more genes selected from the group consisting of the following genes, but the present invention is not limited thereto: genes encoding plant, for example, soybean (*Glycine max*) FAD2 (e.g., NCBI Accession No. NP_001341865.1, XP_006605883.1, XP_006605882.1, XP_006605885.1, XP_006605884.1, or XP_014627765.1), for example, FAD2 genes represented by NCBI Accession No. NM_001354936.1, XM_006605820.2, XM_006605819.2, XM_006605822.2, XM_006605821.2, or XM_014772279.1.

In any exemplary embodiment, the unsaturated fatty acid biosynthesis-associated factor may be FAD3.

A FAD3 (microsomal omega-3 fatty acid desaturase) gene refers to a gene (full-length DNA, cDNA or mRNA) encoding a FAD3 protein also referred to as Fanx. In one example, the FAD3 gene may be one or more genes selected from the group consisting of the following genes, but the present invention is not limited thereto: a gene encoding plant, for example, soybean (*Glycine max*) FAD3 (e.g., NCBI Accession No. NP_001237507.1), for example, an FAD3 gene represented by NCBI Accession No. NM_001250578.1.

In any exemplary embodiment, the unsaturated fatty acid biosynthesis-associated factor may be FAD6.

A FAD6 (fatty acid desaturase 6) gene refers to a gene (full-length DNA, cDNA or mRNA) encoding a FAD6 protein also referred to as FADC or SFD4. In one example, the FAD6 gene may be one or more genes selected from the group consisting of the following genes, but the present invention is not limited thereto: a gene encoding a plant, for example, *Arabidopsis thaliana* FAD6 (e.g., NCBI Accession No. NP_194824.1), for example, a FAD6 gene represented by NCBI Accession No. NM_119243.4.

In any exemplary embodiment, the unsaturated fatty acid biosynthesis-associated factor may be FAD7.

A FAD7 (chloroplast omega 3 fatty acid desaturase isoform 2) gene refers to a gene (full-length DNA, cDNA or mRNA) encoding a FAD7 protein. In one example, the FAD7 gene may be one or more genes selected from the group consisting of the following genes, but the present invention is not limited thereto: a gene encoding a plant, for example, soybean (*Glycine max*) FAD7 (e.g., NCBI Accession No. NP_001237361.1), for example, a FAD7 gene represented by NCBI Accession No. NM_001250432.1.

In any exemplary embodiment, the unsaturated fatty acid biosynthesis-associated factor may be FAD8.

A FAD8 (omega-3 fatty acid desaturase, chloroplastic-like) gene refers to a gene (full-length DNA, cDNA or mRNA) encoding a FAD8 protein. In one example, the FAD8 gene may be one or more genes selected from the group consisting of the following genes, but the present invention is not limited thereto: a gene encoding a plant, for example, soybean (*Glycine max*) FAD8 (e.g., NCBI Accession No. NP_001239777.1), for example, a FAD8 gene represented by NCBI Accession No. NM_001252848.1.

The unsaturated fatty acid biosynthesis-associated factor may be derived from a plant such as soybean, *Arabidopsis thaliana*, sesame, corn and the like, etc.

Information about the genes may be obtained from a known database such as GeneBank of the National Center for Biotechnology Information (NCBI).

In one exemplary embodiment of the present invention, the unsaturated fatty acid biosynthesis-associated factor, for example, FAD2, FAD3, FADE, FAD7 or FAD8, may be artificially manipulated unsaturated fatty acid biosynthesis-associated factor.

In a certain embodiment, the artificially manipulated unsaturated fatty acid biosynthesis-associated factor may be genetically manipulated.

The gene manipulation or modification may be achieved by artificial insertion, deletion, substitution or inversion occurring in a partial or entire region of the genomic sequence of a wild type gene. In addition, the gene manipulation or modification may be achieved by fusion of manipulation or modification of two or more genes.

For example, the gene may be further activated by such gene manipulation or modification, such that a protein encoded from the gene is to be expressed in the form of a protein having an improved function, compared to the innate function. In an example, when a function of the protein encoded by a specific gene is A, a function of a protein expressed by a manipulated gene may be totally different from A or may have an additional function (A+B) including A. For example, a fusion of two or more proteins may be expressed using two or more genes having different or complementary functions due to such gene manipulation or modification.

For example, two or more proteins may be expressed separately or independently in cells by using two or more genes having different or complementary functions due to such gene manipulation or modification.

The manipulated unsaturated fatty acid biosynthesis-associated factor may produce an unsaturated fatty acid by forming one or more double bonds in a saturated fatty acid.

The manipulated unsaturated fatty acid biosynthesis-associated factor may form new one or more double bonds in an unsaturated fatty acid.

The manipulated unsaturated fatty acid biosynthesis-associated factor may change positions of one or more double bonds included in an unsaturated fatty acid.

The manipulated unsaturated fatty acid biosynthesis-associated factor may remove one or more double bonds of an unsaturated fatty acid having two or more double bonds.

The manipulated unsaturated fatty acid biosynthesis-associated factor may change a cis-unsaturated fatty acid into a trans-unsaturated fatty acid.

The manipulated unsaturated fatty acid biosynthesis-associated factor may change a trans-unsaturated fatty acid into a cis-unsaturated fatty acid.

The manipulated unsaturated fatty acid biosynthesis-associated factor may control the content of an unsaturated fatty acid included in a plant.

The manipulated unsaturated fatty acid biosynthesis-associated factor may increase the content of a specific unsaturated fatty acid included in a plant.

The manipulated unsaturated fatty acid biosynthesis-associated factor may decrease the content of a specific unsaturated fatty acid included in a plant.

The manipulation includes all types of structural or functional modifications of the unsaturated fatty acid biosynthesis-associated factor.

The structural modification of the unsaturated fatty acid biosynthesis-associated factor includes all types of modifications, which are not the same as those of a wild type existing in a natural state.

For example, when the unsaturated fatty acid biosynthesis-associated factor is DNA, RNA or a gene, the structural modification may be the loss of one or more nucleotides.

The structural modification may be the insertion of one or more nucleotides.

Here, the inserted nucleotides include all of a subject including an unsaturated fatty acid biosynthesis-associated factor and nucleotides entering from the outside of the subject.

The structural modification may be the substitution of one or more nucleotides.

The structural modification may include the chemical modification of one or more nucleotides.

Here, the chemical modification includes all of the addition, removal and substitution of chemical functional groups.

As another example, when the unsaturated fatty acid biosynthesis-associated factor is a peptide, a polypeptide or a protein, the structural modification may be the loss of one or more amino acids.

The structural modification may be the insertion of one or more amino acids.

Here, the inserted amino acids include all of a subject including an unsaturated fatty acid biosynthesis-associated factor and amino acids entering from the outside of the subject.

The structural modification may be the substitution of one or more amino acids.

The structural modification may include the chemical modification of one or more amino acids.

Here, the chemical modification includes all of the addition, removal and substitution of chemical functional groups.

The structural modification may be the partial or entire attachment of a different peptide, polypeptide or protein.

Here, the different peptide, polypeptide or protein may be an unsaturated fatty acid biosynthesis-associated factor, or a peptide, polypeptide or protein having a different function.

The functional modification of the unsaturated fatty acid biosynthesis-associated factor may include all types having an improved or reduced function, compared to that of a wild type existing in a natural state, and having a third different function.

For example, when the unsaturated fatty acid biosynthesis-associated factor is a peptide, polypeptide or protein, the functional modification may be a mutation of the unsaturated fatty acid biosynthesis-associated factor.

Here, the mutation may be a mutation that enhances or suppresses a function of the unsaturated fatty acid biosynthesis-associated factor.

The functional modification may have an additional function of the unsaturated fatty acid biosynthesis-associated factor.

Here, the additional function may be the same or a different function. In addition, the unsaturated fatty acid biosynthesis-associated factor having the additional function may be fused with a different peptide, polypeptide or protein.

The functional modification may be the enhancement in functionality due to increased expression of the unsaturated fatty acid biosynthesis-associated factor.

The functional modification may be the degradation in functionality due to decreased expression of the unsaturated fatty acid biosynthesis-associated factor.

In an exemplary embodiment, the manipulated unsaturated fatty acid biosynthesis-associated factor may be induced by one or more of the following mutations:

all or partial deletions of the unsaturated fatty acid biosynthesis-associated factor, that is, a gene to be manipulated (hereinafter, referred to as a target gene), for example, deletion of 1 bp or longer nucleotides, for example, 1 to 30, 1 to 27, 1 to 25, 1 to 23, 1 to 20, 1 to 15, 1 to 10, 1 to 5, 1 to 3, or 1 nucleotide of the target gene, substitution of 1 bp or longer nucleotides, for example, 1 to 30, 1 to 27, 1 to 25, 1 to 23, 1 to 20, 1 to 15, 1 to 10, 1 to 5, 1 to 3, or 1 nucleotide of the target gene with a nucleotide different from a wild type, and insertion of one or more nucleotides, for example, 1 to 30, 1 to 27, 1 to 25, 1 to 23, 1 to 20, 1 to 15, 1 to 10, 1 to 5, 1 to 3, or 1 nucleotide (each independently selected from A, T, C and G) into a certain position of the target gene.

A part of the modified target gene ("target region") may be a continuous 1 bp or more, 3 bp or more, 5 bp or more, 7 bp or more, 10 bp or more, 12 bp or more, 15 bp or more, 17 bp or more, or 20 bp or more, for example, 1 bp to 30 bp, 3 bp to 30 bp, 5 bp to 30 bp, 7 bp to 30 bp, 10 bp to 30 bp, 12 bp to 30 bp, 15 bp to 30 bp, 17 bp to 30 bp, 20 bp to 30 bp, 1 bp to 27 bp, 3 bp to 27 bp, 5 bp to 27 bp, 7 bp to 27 bp, 10 bp to 27 bp, 12 bp to 27 bp, 15 bp to 27 bp, 17 bp to 27 bp, 20 bp to 27 bp, 1 bp to 25 bp, 3 bp to 25 bp, 5 bp to 25 bp, 7 bp to 25 bp, 10 bp to 25 bp, 12 bp to 25 bp, 15 bp to 25 bp, 17 bp to 25 bp, 20 bp to 25 bp, 1 bp to 23 bp, 3 bp to 23 bp, 5 bp to 23 bp, 7 bp to 23 bp, 10 bp to 23 bp, 12 bp to 23 bp, 15 bp to 23 bp, 17 bp to 23 bp, 20 bp to 23 bp, 1 bp to 20 bp, 3 bp to 20 bp, 5 bp to 20 bp, 7 bp to 20 bp, 10 bp to 20 bp, 12 bp to 20 bp, 15 bp to 20 bp, 17 bp to 20 bp, 21 bp to 25 bp, 18 bp to 22 bp, or 21 bp to 23 bp region of the base sequence of the gene.

System for Controlling Unsaturated Fatty Acids

One aspect of the present invention relates to a system for controlling an unsaturated fatty acid, which controls the biosynthesis of an unsaturated fatty acid by artificially manipulating an unsaturated fatty acid biosynthesis-associated factor.

The term "system for controlling an unsaturated fatty acid" used herein includes all phenomena affecting the promotion or inhibition of the biosynthesis of an unsaturated fatty acid, and/or the increase or inhibition of the production of unsaturated fatty acids by changing functions of the artificially manipulated unsaturated fatty acid biosynthesis-associated factor, and includes all materials, compositions, methods and uses directly or indirectly involved in the system of controlling the biosynthesis of an unsaturated fatty acid.

Each factor constituting the system for controlling the biosynthesis of an unsaturated fatty acid is also referred to as an "unsaturated fatty acid controlling factor."

The system of the present invention includes a modified mechanism in a plant body, which is associated with an artificially manipulated unsaturated fatty acid biosynthesis-associated factor. By the artificially manipulated unsaturated fatty acid biosynthesis-associated factor, in any exemplary embodiment, the biosynthesis of a C8 to 24:D1 unsaturated fatty acid may be controlled, in any exemplary embodiment, the biosynthesis of a C8 to 24:D2 unsaturated fatty acid may be controlled, in any exemplary embodiment, the production amount of a C8 to 24:D1 unsaturated fatty acid may be controlled, in any exemplary embodiment, the production amount of a C8 to 24:D2 unsaturated fatty acid may be controlled, in any exemplary embodiment, the content of a C8 to 24:D1 unsaturated fatty acid in a plant body may be controlled, in any exemplary embodiment, the content of a C8 to 24:D2 unsaturated fatty acid in a plant body may be controlled, in any exemplary embodiment, the content ratio of the C8 to 24:D1 unsaturated fatty acid and the C8 to 24:D2 unsaturated fatty acid in a plant body may be controlled, in any exemplary embodiment, a double bond of the C8 to 24:D1 unsaturated fatty acid may be added or removed, and in any exemplary embodiment, a double bond of the C8 to 24:D2 unsaturated fatty acid may be added or removed.

In another exemplary embodiment, the system for controlling an unsaturated fatty acid of the present invention includes a composition for manipulating an unsaturated fatty acid biosynthesis-associated factor.

The composition for manipulation may be a composition capable of artificially manipulating an unsaturated fatty acid biosynthesis-associated factor, and preferably, a composition for gene manipulation.

Hereinafter, the composition for gene manipulation will be described.

Composition for Manipulating Unsaturated Fatty Acid Biosynthesis-Associated Factor Manipulation or modification of substances involved in the unsaturated fatty acid biosynthesis-associated factor and the system for controlling an unsaturated fatty acid of the present invention is preferably accomplished by genetic manipulation.

In one aspect, composition and method for manipulating a gene by targeting a partial or entire non-coding or coding region of the unsaturated fatty acid biosynthesis-associated factor may be provided.

In an exemplary embodiment, the composition and method may be used in manipulation or modification of one or more unsaturated fatty acid biosynthesis-associated genes involved in the formation of a desired system for controlling an unsaturated fatty acid. The manipulation or modification may be performed by modification of nucleic acids constituting a gene. As a result of the manipulation, all of knockdown, knock out, and knock in are included.

In an exemplary embodiment, the manipulation may be performed by targeting a promoter region, or a transcription sequence, for example, an intron or exon sequence. A coding sequence, for example, a coding region, an initial coding region may be targeted for the modification of expression and knockout.

In an exemplary embodiment, the modification of nucleic acids may be substitution, deletion, and/or insertion of one or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In an exemplary embodiment, for the knockout of one or more unsaturated fatty acid biosynthesis-associated genes, elimination of expression of one or more of the genes, or one or more knockouts of one or two alleles, the above-mentioned region may be targeted such that one or more unsaturated fatty acid biosynthesis-associated genes contain a deletion or mutation.

In an exemplary embodiment, the knockdown of a gene may be used to decrease the expression of undesired alleles or transcriptomes.

In an exemplary embodiment, non-coding sequences of a promoter, an enhancer, an intron, a 3'UTR, and/or a polyadenylation signal may be targeted to be used in modifying an unsaturated fatty acid biosynthesis-associated gene affecting an unsaturated fatty acid biosynthesis function.

In an exemplary embodiment, the activity of an unsaturated fatty acid biosynthesis-associated gene may be regulated, for example, activated or inactivated by the modification of nucleic acids of the gene.

In an exemplary embodiment, the modification of nucleic acids of the gene may catalyze cleavage of a single strand or double strands, that is, breaks of nucleic acid strands in a specific region of the target gene by a guide nucleic acid-editor protein complex, resulting in inactivation of the target gene.

In an exemplary embodiment, the nucleic acid strand breaks may be repaired through a mechanism such as homologous recombination or non-homologous end joining (NHEJ).

In this case, when the NHEJ mechanism takes place, a change in DNA sequence is induced at the cleavage site, resulting in inactivation of the gene. The repair by NHEJ may induce substitution, insertion or deletion of a short gene fragment, and may be used in the induction of a corresponding gene knockout.

In another aspect, the present invention provides a composition for manipulating an unsaturated fatty acid biosynthesis-associated factor.

The composition for manipulation is a composition that is able to artificially manipulate an unsaturated fatty acid biosynthesis-associated factor, and preferably, a composition for gene manipulation.

The composition may be employed in gene manipulation for one or more unsaturated fatty acid biosynthesis-associated factors involved in formation of a desired system for controlling an unsaturated fatty acid.

The gene manipulation may be performed in consideration of a gene expression regulating process.

In an exemplary embodiment, it may be performed by selecting a suitable manipulation means for each stage of transcription, RNA processing, RNA transporting, RNA degradation, translation, and protein modification regulating stages.

In an exemplary embodiment, small RNA (sRNA) interferes with mRNA or reduces stability thereof using RNA interference (RNAi) or RNA silencing, and in some cases, breaks up mRNA to interrupt the delivery of protein synthesis information, resulting in regulation of the expression of genetic information.

The gene manipulation may be performed by modification of nucleic acids constituting an unsaturated fatty acid biosynthesis-associated factor. As manipulation results, all of knockdown, knockout, and knockin are included.

In a certain embodiment, the modification of nucleic acids may be substitution, deletion, and/or insertion of one or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In a certain embodiment, for knockout of one or more unsaturated fatty acid biosynthesis-associated factors, elimination of the expression of one or more factors, or one or more knockouts of one or two alleles, the gene may be manipulated such that one or more unsaturated fatty acid biosynthesis-associated factors contain a deletion or mutation.

In a certain embodiment, knockdown of the unsaturated fatty acid biosynthesis-associated factor may be used to decrease expression of undesired alleles or transcriptomes.

In a certain embodiment, the modification of nucleic acids may be insertion of one or more nucleic acid fragments or genes. Here, the nucleic acid fragment may be a nucleic acid sequence consisting of one or more nucleotides, and a length of the nucleic acid fragment may be 1 to 40 bp, 1 to 50 bp, 1 to 60 bp, 1 to 70 bp, 1 to 80 bp, 1 to 90 bp, 1 to 100 bp, 1 to 500 bp or 1 to 1000 bp. Here, the inserted gene may be one of the unsaturated fatty acid biosynthesis-associated factors, or a gene having a different function.

In an exemplary embodiment, the modification of nucleic acids may employ a wild type or variant enzyme which is capable of catalyzing hydrolysis (cleavage) of bonds between nucleic acids in a DNA or RNA molecule, preferably, a DNA molecule. It may also employ a guide nucleic acid-editor protein complex.

For example, the gene may be manipulated using one or more nucleases selected from the group consisting of a meganuclease, a zinc finger nuclease, CRISPR/Cas9 (Cas9 protein), CRISPR-Cpf1 (Cpf1 protein) and a TALE-nuclease, thereby regulating the expression of genetic information.

In a certain embodiment, non-limitedly, the gene manipulation may be mediated by NHEJ or homology-directed repair (HDR) using a guide nucleic acid-editor protein complex, for example, a CRISPR/Cas system.

In this case, when the NHEJ mechanism takes place, a change in DNA sequence may be induced at a cleavage site, thereby inactivating the gene. Repair by NHEJ may induce substitution, insertion or deletion of a short gene fragment, and may be used in the induction of the knockout of a corresponding gene.

In another aspect, the present invention may provide the gene manipulation site.

In an exemplary embodiment, when the gene is modified by NHEJ-mediated modification, the gene manipulation site may be a site in the gene, triggering the decrease or elimination of expression of an unsaturated fatty acid biosynthesis-associated gene product.

For example, the site may be in an initial coding region,
a promoter sequence,
an enhancer sequence,
a specific intron sequence, or
a specific exon sequence.

In an exemplary embodiment, the composition for manipulating an unsaturated fatty acid biosynthesis-associated factor may target
an unsaturated fatty acid biosynthesis-associated factor affecting the regulation of biosynthesis of unsaturated fatty acid, such as an FAD gene, preferably an FAD2 gene, an FAD3 gene, an FAD6 gene, an FAD7 gene, or an FAD8 gene, as a manipulation subject. Most preferably, the composition for manipulating an unsaturated fatty acid biosynthesis-associated factor may target an FAD2 gene as a manipulation subject.

Examples of target regions of the FAD2 gene, that is, target sequences for regions in which gene manipulation occurs or which are recognized for gene manipulation are summarized in Table 1.

The target sequence may target one or more genes.

The target sequence may simultaneously target two or more genes. Here, the two or more genes may be homologous genes or heterologous genes.

The gene may contain one or more target sequences.

The gene may be simultaneously targeted at two or more target sequences.

The gene may be changed in the site and number of gene manipulations according to the number of target sequences.

The gene manipulation may be designed in various forms depending on the number and positions of the target sequences.

The gene manipulation may simultaneously occur in two or more target sequences. Here, the two or more target sequences may be present in the homologous gene or heterologous gene.

The gene manipulation may be simultaneously performed with respect to the two or more genes. Here, the two or more genes may be homologous genes or heterologous genes.

Hereinafter, examples of target sequences which are able to be used in embodiments of the present invention are shown in the following tables:

TABLE 1

Table 1. Target sequences of FAD2 gene

| No. | Target sequence (including PAM) |
|---|---|
| 1 | ATAGATTGGCCATGCAATGAGGG (SEQ ID NO: 1) |
| 2 | AATAGATTGGCCATGCAATGAGG (SEQ ID NO: 2) |

TABLE 1-continued

Table 1. Target sequences of FAD2 gene

| No. | Target sequence (including PAM) |
|---|---|
| 3 | CCTTGGAGAACCCAATAGATTGG (SEQ ID NO: 3) |
| 4 | TGGGTGATTGCTCACGAGTGTGG (SEQ ID NO: 4) |
| 5 | TTTTAGTCCCTTATTTCTCATGG (SEQ ID NO: 5) |
| 6 | AAACACTTCATCACGGTCAAGGG (SEQ ID NO: 6) |
| 7 | GTGTTTGGAACCCTTGAGAGAGG (SEQ ID NO: 7) |
| 8 | GTGAATGGTGGCTTTGTGTTTGG (SEQ ID NO: 8) |
| 9 | ACAAAGCCACCATTCACTGTTGG (SEQ ID NO: 9) |
| 10 | AGTTGGCCAACAGTGAATGGTGG (SEQ ID NO: 10) |
| 11 | TTGAGTTGGCCAACAGTGAATGG (SEQ ID NO: 11) |
| 12 | TGAAAGGTCATAAACAACATAGG (SEQ ID NO: 12) |
| 13 | CAAACACTTCATCACGGTCAAGG (SEQ ID NO: 13) |
| 14 | AACCAAAATCCAAAGTTGCATGG (SEQ ID NO: 14) |
| 15 | TGGGAGCATAAGGGTGGTAGTGG (SEQ ID NO: 15) |
| 16 | AATATATGGGAGCATAAGGGTGG (SEQ ID NO: 16) |
| 17 | GTTTGGCTGCTATGTGTTTATGG (SEQ ID NO: 17) |
| 18 | TTTGGCTGCTATGTGTTTATGGG (SEQ ID NO: 18) |
| 19 | TTGGCTGCTATGTGTTTATGGGG (SEQ ID NO: 19) |
| 20 | GCAACTATGGACAGAGATTATGG (SEQ ID NO: 20) |
| 21 | CACCATTTTACAAGGCACTGTGG (SEQ ID NO: 21) |
| 22 | CTTCATCTGGCTCCACATAGAGG (SEQ ID NO: 22) |
| 23 | CTCTATGTGGAGCCAGATGAAGG (SEQ ID NO: 23) |
| 24 | TTCTCGGATGTTCCTTCATCTGG (SEQ ID NO: 24) |
| 25 | AGATGAAGGAACATCCGAGAAGG (SEQ ID NO: 25) |
| 26 | GATGAAGGAACATCCGAGAAGGG (SEQ ID NO: 26) |
| 27 | CATCCGAGAAGGGCGTGTATTGG (SEQ ID NO: 27) |
| 28 | GTACCAATACACGCCCTTCTCGG (SEQ ID NO: 28) |
| 29 | AGAAGGGCGTGTATTGGTACAGG (SEQ ID NO: 29) |
| 30 | TTGGGACAAACACTTCATCACGG (SEQ ID NO: 30) |

Composition for Manipulation-Gene Scissors System

The system for controlling an unsaturated fatty acid of the present invention may include a guide nucleic acid-editor protein complex as a composition for manipulating an unsaturated fatty acid biosynthesis-associated factor.

Guide Nucleic Acid-Editor Protein Complex

The term "guide nucleic acid-editor protein complex" refers to a complex formed through the interaction between a guide nucleic acid and an editor protein, and the nucleic acid-protein complex includes a guide nucleic acid and an editor protein.

The term "guide nucleic acid" refers to a nucleic acid capable of recognizing a target nucleic acid, gene, chromosome or protein.

The guide nucleic acid may be present in the form of DNA, RNA or a DNA/RNA hybrid, and may have a nucleic acid sequence of 5 to 150 bases.

The guide nucleic acid may include one or more domains.

The domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The guide nucleic acid may have one continuous nucleic acid sequence.

For example, the one continuous nucleic acid sequence may be (N)m, where N represents A, T, C or G, or A, U, C or G, and m is an integer of 1 to 150.

The guide nucleic acid may have two or more continuous nucleic acid sequences.

For example, the two or more continuous nucleic acid sequences may be (N)m and (N)o, where N represents A, T, C or G, or A, U, C or G, m and o are an integer of 1 to 150, and m and o may be the same as or different from each other.

The term "editor protein" refers to a peptide, polypeptide or protein which is able to directly bind to or interact with, without direct binding to, a nucleic acid.

The editor protein may be an enzyme.

The editor protein may be a fusion protein.

Here, the "fusion protein" refers to a protein that is produced by fusing an enzyme with an additional domain, peptide, polypeptide or protein.

The term "enzyme" refers to a protein that contains a domain capable of cleaving a nucleic acid, gene, chromosome or protein.

The additional domain, peptide, polypeptide or protein may be a functional domain, peptide, polypeptide or protein, which has a function the same as or different from the enzyme.

The fusion protein may include an additional domain, peptide, polypeptide or protein at one or more regions of the amino terminus (N-terminus) of the enzyme or the vicinity thereof; the carboxyl terminus (C-terminus) or the vicinity thereof; the middle part of the enzyme; and a combination thereof.

The fusion protein may include a functional domain, peptide, polypeptide or protein at one or more regions of the N-terminus of the enzyme or the vicinity thereof; the C-terminus or the vicinity thereof; the middle part of the enzyme; and a combination thereof.

The guide nucleic acid-editor protein complex may serve to modify a subject.

The subject may be a target nucleic acid, gene, chromosome or protein.

For example, the guide nucleic acid-editor protein complex may result in final regulation (e.g., inhibition, suppression, reduction, increase or promotion) of the expression of a protein of interest, removal of the protein, or expression of a new protein.

Here, the guide nucleic acid-editor protein complex may act at a DNA, RNA, gene or chromosome level.

The guide nucleic acid-editor protein complex may act in gene transcription and translation stages.

The guide nucleic acid-editor protein complex may act at a protein level.

1. Guide Nucleic Acids

The guide nucleic acid is a nucleic acid that is capable of recognizing a target nucleic acid, gene, chromosome or protein, and forms a guide nucleic acid-protein complex.

Here, the guide nucleic acid is configured to recognize or target a nucleic acid, gene, chromosome or protein targeted by the guide nucleic acid-protein complex.

The guide nucleic acid may be present in the form of DNA, RNA or a DNA/RNA mixture, and have a 5 to 150-nucleic acid sequence.

The guide nucleic acid may be present in a linear or circular shape.

The guide nucleic acid may be one continuous nucleic acid sequence.

For example, the one continuous nucleic acid sequence may be (N)m, where N is A, T, C or G, or A, U, C or G, and m is an integer of 1 to 150.

The guide nucleic acid may be two or more continuous nucleic acid sequences.

For example, the two or more continuous nucleic acid sequences may be (N)m and (N)o, where N represents A, T, C or G, or A, U, C or G, m and o are an integer of 1 to 150, and may be the same as or different from each other.

The guide nucleic acid may include one or more domains.

Here, the domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The domains will be described below.

i) Guide Domain

The term "guide domain" is a domain having a complementary guide sequence which is able to form a complementary bond with a target sequence on a target gene or nucleic acid, and serves to specifically interact with the target gene or nucleic acid.

The guide sequence is a nucleic acid sequence complementary to the target sequence on a target gene or nucleic acid, which has, for example, at least 50%, 55%, 60%, 65%, 70%, 75%, 80%, 85%, 90%, 95% or more complementarity or complete complementarity.

The guide domain may be a sequence of 5 to 50 bases.

In an example, the guide domain may be a sequence of 5 to 50, 10 to 50, 15 to 50, 20 to 50, 25 to 50, 30 to 50, 35 to 50, 40 to 50 or 45 to 50 bases.

In another example, the guide domain may be a sequence of 1 to 5, 5 to 10, 10 to 15, 15 to 20, 20 to 25, 25 to 30, 30 to 35, 35 to 40, 40 to 45, or 45 to 50 bases.

The guide domain may have a guide sequence.

The guide sequence may be a complementary base sequence which is able to form a complementary bond with the target sequence on the target gene or nucleic acid.

The guide sequence may be a nucleic acid sequence complementary to the target sequence on the target gene or nucleic acid, which has, for example, at least 70%, 75%, 80%, 85%, 90%, 95% or more complementarity or complete complementarity.

The guide sequence may be a 5 to 50 bases sequence.

In an example, the guide domain may be a 5 to 50, 10 to 50, 15 to 50, 20 to 50, 25 to 50, 30 to 50, 35 to 50, 40 to 50, or 45 to 50-base sequence.

In another example, the guide sequence may be a 1 to 5, 5 to 10, 10 to 15, 15 to 20, 20 to 25, 25 to 30, 30 to 35, 35 to 40, 40 to 45, or 45 to 50-base sequence.

In addition, the guide domain may include a guide sequence and an additional base sequence.

The additional base sequence may be utilized to improve or degrade the function of the guide domain.

The additional base sequence may be utilized to improve or degrade the function of the guide sequence.

The additional base sequence may be a 1 to 35-base sequence.

In one example, the additional base sequence may be a 5 to 35, 10 to 35, 15 to 35, 20 to 35, 25 to 35 or 30 to 35-base sequence.

In another example, the additional base sequence may be a 1 to 5, 5 to 10, 10 to 15, 15 to 20, 20 to 25, 25 to 30 or 30 to 35-base sequence.

The additional base sequence may be located at the 5' end of the guide sequence.

The additional base sequence may be located at the 3' end of the guide sequence.

ii) First Complementary Domain

The term "first complementary domain" is a nucleic acid sequence including a nucleic acid sequence complementary to a second complementary domain, and has enough complementarity so as to form a double strand with the second complementary domain.

The first complementary domain may be a 5 to 35-base sequence.

In an example, the first complementary domain may be a 5 to 35, 10 to 35, 15 to 35, 20 to 35, 25 to 35, or 30 to 35-base sequence.

In another example, the first complementary domain may be a 1 to 5, 5 to 10, 10 to 15, 15 to 20, 20 to 25, 25 to 30 or 30 to 35-base sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-base sequence.

In one example, the linker domain may be a 1 to 5, 5 to 10, 10 to 15, 15 to 20, 20 to 25, or 25 to 30-base sequence.

In another example, the linker domain may be a 1 to 30, 5 to 30, 10 to 30, 15 to 30, 20 to 30, or 25 to 30-base sequence.

iv) Second Complementary Domain

The term "second complementary domain" is a nucleic acid sequence including a nucleic acid sequence complementary to the first complementary domain, and has enough complementarity so as to form a double strand with the first complementary domain.

The second complementary domain may have a base sequence complementary to the first complementary domain, and a base sequence having no complementarity to the first complementary domain, for example, a base sequence not forming a double strand with the first complementary domain, and may have a longer base sequence than the first complementary domain.

The second complementary domain may have a 5 to 35-base sequence.

In an example, the second complementary domain may be a 1 to 35, 5 to 35, 10 to 35, 15 to 35, 20 to 35, 25 to 35, or 30 to 35-base sequence.

In another example, the second complementary domain may be a 1 to 5, 5 to 10, 10 to 15, 15 to 20, 20 to 25, 25 to 30, or 30 to 35-base sequence.

v) Proximal Domain

The term "proximal domain" is a nucleic acid sequence located adjacent to the second complementary domain.

The proximal domain may have a complementary base sequence therein, and may be formed in a double strand due to a complementary base sequence.

The proximal domain may be a 1 to 20-base sequence.

In one example, the proximal domain may be a 1 to 20, 5 to 20, 10 to 20 or 15 to 20-base sequence.

In another example, the proximal domain may be a 1 to 5, 5 to 10, 10 to 15 or 15 to 20-base sequence.

vi) Tail Domain

The term "tail domain" is a nucleic acid sequence located at one or more ends of the both ends of the guide nucleic acid.

The tail domain may have a complementary base sequence therein, and may be formed in a double strand due to a complementary base sequence.

The tail domain may be a 1 to 50-base sequence.

In an example, the tail domain may be a 5 to 50, 10 to 50, 15 to 50, 20 to 50, 25 to 50, 30 to 50, 35 to 50, 40 to 50, or 45 to 50-base sequence.

In another example, the tail domain may be a 1 to 5, 5 to 10, 10 to 15, 15 to 20, 20 to 25, 25 to 30, 30 to 35, 35 to 40, 40 to 45, or 45 to 50-base sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

As a specific example of the guide nucleic acid of the present invention, gRNA will be described below.

qRNA

The term "gRNA" refers to a nucleic acid capable of specifically targeting a gRNA-CRISPR enzyme complex, that is, a CRISPR complex, with respect to a target gene or nucleic acid. In addition, the gRNA is a nucleic acid-specific RNA which may bind to a CRISPR enzyme and guide the CRISPR enzyme to the target gene or nucleic acid.

The gRNA may include multiple domains. Due to each domain, interactions may occur in a three-dimensional structure or active form of a gRNA strand, or between these strands.

The gRNA may be called single-stranded gRNA (single RNA molecule); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain, a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid and a first complementary domain; and a second strand which includes a second complementary domain, a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; a second complementary domain, and a domain having a sequence complementary to the first complementary domain sequence, thereby forming a double-stranded nucleic acid with the first complementary domain in the 5' to 3' direction.

i) Guide Domain

The guide domain includes a complementary guide sequence capable of forming a complementary bond with a target sequence on a target gene or nucleic acid. The guide sequence may be a nucleic acid sequence having complementarity to the target sequence on the target gene or nucleic acid, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

The guide domain may be a 5 to 50-base sequence.

As an exemplary embodiment, the guide domain may be a 16, 17, 18, 19, 20, 21, 22, 23, 24 or 25-base sequence.

As an exemplary embodiment, the guide domain may include a 16, 17, 18, 19, 20, 21, 22, 23, 24 or 25-base sequence.

Here, the guide domain may include a guide sequence.

The guide sequence may be a complementary base sequence capable of forming a complementary bond with a target sequence on a target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of a unsaturated fatty acid biosynthesis-associated factor such as an FAD gene, preferably an FAD2 gene, an FAD3 gene, an FAD6 gene, an FAD7 or an FAD8 gene, which has, for example, at least 70%, 75%, 80%, 85%, 90% or 95% or more complementarity or complete complementarity.

The guide sequence may be a 5 to 50-base sequence.

In an exemplary embodiment, the guide sequence may be a 16, 17, 18, 19, 20, 21, 22, 23, 24 or 25-base sequence.

In one exemplary embodiment, the guide sequence may include a 16, 17, 18, 19, 20, 21, 22, 23, 24 or 25-base sequence.

In one exemplary embodiment, the guide sequence may be a nucleic acid sequence complementary to a target sequence of the FAD2 gene, which is a 16, 17, 18, 19, 20, 21, 22, 23, 24 or 25-base sequence.

In one exemplary embodiment, the guide sequence may be a nucleic acid sequence complementary to a target sequence of the FAD3 gene, which is a 16, 17, 18, 19, 20, 21, 22, 23, 24 or 25-base sequence.

In one exemplary embodiment, the guide sequence may be a nucleic acid sequence complementary to a target sequence of the FAD6 gene, which is a 16, 17, 18, 19, 20, 21, 22, 23, 24 or 25-base sequence.

In one exemplary embodiment, the guide sequence may be a nucleic acid sequence complementary to a target sequence of the FAD7 gene, which is a 16, 17, 18, 19, 20, 21, 22, 23, 24 or 25-base sequence.

In one exemplary embodiment, the guide sequence may be a nucleic acid sequence complementary to a target sequence of the FAD8 gene, which is a 16, 17, 18, 19, 20, 21, 22, 23, 24 or 25-base sequence.

Here, target sequences of the target genes, that is, the unsaturated fatty acid biosynthesis-associated factors such as the FAD2 gene for the guide sequence are listed above in Table 1, but the present invention is not limited thereto.

Here, the guide domain may include a guide sequence and an additional base sequence.

The additional base sequence may be a 1 to 35-base sequence.

In one exemplary embodiment, the additional base sequence may be a 1, 2, 3, 4, 5, 6, 7, 8, 9 or 10-base sequence.

For example, the additional base sequence may be a single base sequence, guanine (G), or a sequence of two bases, GG.

The additional base sequence may be located at the 5' end of the guide sequence.

The additional base sequence may be located at the 3' end of the guide sequence.

Selectively, a part or all of the base sequence of the guide domain may include a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

ii) First Complementary Domain

The first complementary domain includes a nucleic acid sequence complementary to a second complementary domain, and has enough complementarity such that it is able to form a double strand with the second complementary domain.

Here, the first complementary domain may be a 5 to 35-base sequence. The first complementary domain may include a 5 to 35-base sequence.

In one exemplary embodiment, the first complementary domain may be a 5, 6, 7, 8, 9, 10, 11, 12, 13, 14, 15, 16, 17, 18, 19, 20, 21, 22, 23, 24, or 25-base sequence.

In another embodiment, the first complementary domain may include a 5, 6, 7, 8, 9, 10, 11, 12, 13, 14, 15, 16, 17, 18, 19, 20, 21, 22, 23, 24, or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Staphylococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUAGAGCUA-3' (SEQ ID NO: 42) or a base sequence having partial, that is, at least 50% or more, or complete homology with 5'-GUUUAGAGCUA-3'(SEQ ID NO: 42). Here, the first complementary domain may further include (X)n, resulting in 5'-GUUUAGAGCUA(X)n-3'(SEQ ID NO: 42). The X may be selected from the group consisting of bases A, T, U and G, and the n may represent the number of bases, which is an integer of 5 to 15. Here, the (X)n may be n repeats of the same base, or a mixture of n bases of A, T, U and G.

In another embodiment, when the first complementary domain is the first complementary domain of *Campylobacter jejuni* or a first complementary domain derived therefrom, the first complementary domain may be 5'-GUUUAGUCCCUUUUUAAAUUUCUU-3'(SEQ ID NO: 43), or a base sequence having partial, that is, at least 50% or more, or complete homology with 5'-GUUUAGUCCCUUUUUAAAUUUCUU-3'(SEQ ID NO: 43). Here, the first complementary domain may further include (X)n, resulting in 5'-GUUUAGUCCCUUUUUAAAUUUCUU(X)n-3'(SEQ ID NO: 43). The X may be selected from the group consisting of bases A, T, U and G, and the n may represent the number of bases, which is an integer of 5 to 15. Here, the (X)n may represent n repeats of the same base, or a mixture of n bases of A, T, U and G.

In another embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasiicus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *candidatus Methanoplasma termitum* or *Eubacterium eligens*, or a first complementary domain derived therefrom.

For example, when the first complementary domain is the first complementary domain of Parcubacteria bacterium or a first complementary domain derived therefrom, the first complementary domain may be 5'-UUUGUAGAU-3', or a base sequence having partial, that is, at least 50% or more homology with 5'-UUUGUAGAU-3'. Here, the first complementary domain may further include (X)n, resulting in 5'-(X)nUUUGUAGAU-3'. The X may be selected from the group consisting of bases A, T, U and G, and the n may represent the number of bases, which is an integer of 1 to 5. Here, the (X)n may represent n repeats of the same base, or a mixture of n bases of A, T, U and G.

Selectively, a part or all of the base sequence of the first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iii) Linker Domain

The linker domain is a nucleic acid sequence connecting two or more domains, and connects two or more identical or different domains. The linker domain may be connected with two or more domains by covalent bonding or non-covalent bonding, or may connect two or more domains by covalent or non-covalent bonding.

The linker domain may be a nucleic acid sequence connecting a first complementary domain with a second complementary domain to produce single-stranded gRNA.

The linker domain may be connected with the first complementary domain and the second complementary domain by covalent or non-covalent bonding.

The linker domain may connect the first complementary domain with the second complementary domain by covalent or non-covalent bonding The linker domain may be a 1 to 30-base sequence. The linker domain may include a 1 to 30-base sequence.

In an exemplary embodiment, the linker domain may be a 1 to 5, 5 to 10, 10 to 15, 15 to 20, 20 to 25 or 25 to 30-base sequence.

In an exemplary embodiment, the linker domain may include a 1 to 5, 5 to 10, 10 to 15, 15 to 20, 20 to 25, or 25 to 30-base sequence.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding. The linker domain may be used to produce single-stranded gRNA by being connected with crRNA and tracrRNA of double-stranded gRNA or connecting the crRNA with the tracrRNA by covalent or non-covalent bonding.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iv) Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be a 5 to 35-base sequence. The first complementary domain may include a 5 to 35-base sequence.

In an exemplary embodiment, the second complementary domain may be a 5, 6, 7, 8, 9, 10, 11, 12, 13, 14, 15, 16, 17, 18, 19, 20, 21, 22, 23, 24 or 25-base sequence.

In an exemplary embodiment, the second complementary domain may include a 5, 6, 7, 8, 9, 10, 11, 12, 13, 14, 15, 16, 17, 18, 19, 20, 21, 22, 23, 24 or 25-base sequence.

In addition, the second complementary domain may have homology with a natural second complementary domain, or may be derived from the natural second complementary domain. In addition, the second complementary domain may have a difference in base sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Staphylococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3'(SEQ ID NO: 44), or a base sequence having partial, that is, at least 50% or more homology with 5'-UAGCAAGUUAAAAU-3'(SEQ ID NO: 44) (a base sequence forming a double strand with the first complementary domain is underlined). Here, the second complementary domain may further include (X)n and/or (X)m, resulting in 5'-(X)n UAGCAAGUUAAAAU(X)m-3' (SEQ ID NO: 44). The X may be selected from the group consisting of bases A, T, U and G, and each of the n and m may represent the number of bases, in which the n may be an integer of 1 to 15, and the m may be an integer of 1 to 6. Here, the (X)n may represent n repeats of the same base, or a mixture of n bases of A, T, U and G. In addition, (X)m may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3'(SEQ ID NO: 45), or a base sequence having partial, that is, at least 50% or more homology with 5'-AAGAAAUUUAAAAAGGGACUAAAAU-3'(SEQ ID NO: 45) (a base sequence forming a double strand with the first complementary domain is underlined). Here, the second complementary domain may further include (X)n and/or (X)m, resulting in 5'-(X)nAAGAAAUUUAAAAAGGGACUAAAAU(X)m-3'(SEQ ID NO: 45). The X may be selected from the group consisting of bases A, T, U and G, and each of the n and m may represent the number of bases, in which the n may be an integer of 1 to 15, and the m may be an integer of 1 to 6. Here, (X)n may represent n repeats of the same base, or a mixture of n bases of A, T, U and G. In addition, (X)m may represent m repeats of the same base, or a mixture of m bases of A, T, U and G.

In another embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasiicus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *candidatus Methanoplasma termitum* or *Eubacterium eligens*, or a first complementary domain derived therefrom.

For example, when the second complementary domain is a second complementary domain of Parcubacteria bacterium or a second complementary domain derived therefrom, the second complementary domain may be 5'-AAAUUUC- UACU(SEQ ID NO: 46)-3', or a base sequence having partial, that is, at least 50% or more homology with 5'-AAAUUUCUACU-3'(SEQ ID NO: 46) (a base sequence forming a double strand with the first complementary domain is underlined). Here, the second complementary domain may further include (X)n and/or (X)m, resulting in 5'-(X)nAAAUUUCUACU(X)m-3'(SEQ ID NO: 46). The X may be selected from the group consisting of bases A, T, U and G, and each of the n and m may represent the number of bases, in which the n may be an integer of 1 to 10, and the m may be an integer of 1 to 6. Here, the (X)n may represent n repeats of the same base, or a mixture of n bases of A, T, U and G. In addition, the (X)m may represent m repeats of the same base, or a mixture of m bases of A, T, U and G.

Selectively, a part or all of the base sequence of the second complementary domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

v) Proximal Domain

The proximal domain is a sequence of 1 to 20 bases located adjacent to the second complementary domain, and a domain located at the 3'end direction of the second complementary domain. Here, the proximal domain may be used to form a double strand between complementary base sequences therein.

In one exemplary embodiment, the proximal domain may be a 5, 6, 7, 8, 8, 9, 10, 11, 12, 13, 14 or 15-base sequence.

In another embodiment, the proximal domain may include a 5, 6, 7, 8, 8, 9, 10, 11, 12, 13, 14 or 15-base sequence.

In addition, the proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes, Campylobacter jejuni, Streptococcus thermophilus, Staphylococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGCUAGUCCG-3'(SEQ ID NO: 47), or a base sequence having partial, that is, at least 50% or more homology with 5'-AAGGCUAGUCCG-3'(SEQ ID NO: 47). Here, the proximal domain may further include (X)n, resulting in 5'-AAGGCUAGUCCG(X)n-3'(SEQ ID NO: 47). The X may be selected from the group consisting of bases A, T, U and G, and the n may represent the number of bases, which is an integer of 1 to 15. Here, the (X)n may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3'(SEQ ID NO: 48), or a base sequence having at least 50% or more homology with 5'-AAAGAGUUUGC-3'(SEQ ID NO: 48). Here, the proximal domain may further include (X)n, resulting in 5'-AAAGAGUUUGC(X)n-3'(SEQ ID NO: 48). The X may be selected from the group consisting of bases A, T, U and G, and the n may represent the number of bases, which is an integer of 1 to 40. Here, the (X)n may represent n repeats of the same base, or a mixture of n bases of A, T, U and G.

Selectively, a part or all of the base sequence of the proximal domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

vi) Tail Domain

The tail domain is a domain which is able to be selectively added to the 3' end of single-stranded gRNA or double-stranded gRNA. The tail domain may be a 1 to 50-base sequence, or include a 1 to 50-base sequence. Here, the tail domain may be used to form a double strand between complementary base sequences therein.

In an exemplary embodiment, the tail domain may be a 1 to 5, 5 to 10, 10 to 15, 15 to 20, 20 to 25, 25 to 30, 30 to 35, 35 to 40, 40 to 45, or 45 to 50-base sequence.

In an exemplary embodiment, the tail domain may include a 1 to 5, 5 to 10, 10 to 15, 15 to 20, 20 to 25, 25 to 30, 30 to 35, 35 to 40, 40 to 45, or 45 to 50-base sequence.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Staphylococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3'(SEQ ID NO: 49), or a base sequence having partial, that is, at least 50% or more homology with 5'-UUAUCAAC-UUGAAAAAGUGGCACCGAGUCGGUGC-3'(SEQ ID NO: 49). Here, the tail domain may further include (X)n, resulting in 5'-UUAUCAAC-UUGAAAAAGUGGCACCGAGUCGGUGC(X)n-3'(SEQ ID NO: 49). The X may be selected from the group consisting of bases A, T, U and G, and the n may represent the number of bases, which is an integer of 1 to 15. Here, the (X)n may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3'(SEQ ID NO: 50), or a base sequence having partial, that is, at least 50% or more homology with 5'-GGGACUCUGCGGGGUUA-CAAUCCCCUAAAACCGCUUUU-3'(SEQ ID NO: 50). Here, the tail domain may further include (X)n, resulting in 5'-GGGACUCUGCGGGGUUACAAUCCCC-UAAAACCGCUUUU(X)n-3'(SEQ ID NO: 50).

The X may be selected from the group consisting of bases A, T, U and G, and the n may represent the number of bases, which is an integer of 1 to 15. Here, the (X)n may represent n repeats of the same base, or a mixture of n bases of A, T, U and G.

In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of the base sequence of the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of

5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

First Strand

Guide Domain

In the first strand, the guide domain includes a complementary guide sequence which is able to form a complementary bond with a target sequence on a target gene or nucleic acid. The guide sequence is a nucleic acid sequence complementary to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be a 5 to 50-base sequence, or includes a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence which is able to form a complementary bond with a target sequence on a target gene or nucleic acid, which has, for example, at least 70%, 75%, 80%, 85%, 90% or 95% or more complementarity or complete complementarity.

In an exemplary embodiment, the guide sequence may be a nucleic acid sequence complementary to a target gene, that is, a target sequence of a unsaturated fatty acid biosynthesis-associated factor such as an FAD gene, preferably an FAD2 gene, an FAD3 gene, an FAD6 gene, an FAD7 gene or an FAD8 gene, which has, for example, at least 70%, 75%, 80%, 85%, 90% or 95% or more complementarity or complete complementarity.

Here, the guide sequence may be a 5 to 50-base sequence or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the FAD2 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the FAD3 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the FAD6 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the FAD7 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the FAD8 gene. The guide sequence may be or include a 5 to 50-base sequence. For example, the guide sequence may be or include a 16, 17, 18, 19, 20, 21, 22, 23, 24 or 25-base sequence.

Here, for the guide sequence, target sequences of a target gene, that is, unsaturated fatty acid biosynthesis-associated factors such as an FAD2 gene are listed above in Table 1, but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may include one base, guanine (G), or two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain includes a nucleic acid sequence complementary to a second complementary domain of the second strand, and is a domain having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in base sequence according to a species existing in nature, may be derived from the first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Staphylococcus aureus* or *Neisseria meningitides*, or a first complementary domain derived therefrom.

Selectively, the first complementary domain may include an additional base sequence which does not undergo complementary bonding with the second complementary domain of the second strand.

Here, the additional base sequence may be a sequence of 1 to 15 bases. For example, the additional base sequence may be a sequence of 1 to 5, 5 to 10, or 10 to 15 bases.

Selectively, a part or all of the base sequence of the guide domain and/or first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the first strand may consist of 5'-[guide domain]-[first complementary domain]-3' as described above.

In addition, the first strand may optionally include an additional base sequence.

In one example, the first strand may be

5'-($N_{target}$)-(Q)$_m$-3'; or

5'-(X)$_a$-($N_{target}$)-(X)$_b$-(Q)$_m$-(X)$_c$-3'.

Here, the Ntarget is a base sequence capable of forming a complementary bond with a target sequence on a target gene or nucleic acid, and a base sequence region which may be changed according to a target sequence on a target gene or nucleic acid.

In one exemplary embodiment, Ntarget may be a base sequence capable of forming a complementary bond with a target gene, that is, a target sequence of an unsaturated fatty acid biosynthesis-associated factor such as an FAD gene, preferably an FAD2 gene, an FAD3 gene, an FAD6 gene, an FAD7 gene or an FAD8 gene.

Here, the (Q)m is a base sequence including the first complementary domain, which is able to form a complementary bond with the second complementary domain of the second strand. The (Q)m may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a *Streptococcus pyogenes*-derived first complementary domain, the (Q)m may be 5'-GUUUUAGAGCUA-3'(SEQ ID NO: 42), or a base sequence having at least 50% or more homology with 5'-GUUUUAGAGCUA-3'(SEQ ID NO: 42).

In another example, when the first complementary domain has partial or complete homology with a first complementary domain of *Campylobacter jejuni* or a *Campylobacter jejuni*-derived first complementary domain, the (Q)m may be 5'-GUUUUAGUCCC-UUUUUAAAUUUCUU-3'(SEQ ID NO: 43), or a base sequence having at least 50% or more homology with 5'-GUUUUAGUCCCUUUUUAAAUUUCUU-3'(SEQ ID NO: 43).

In still another example, when the first complementary domain has partial or complete homology with a first complementary domain of *Streptococcus thermophilus* or a *Streptococcus thermophilus*-derived first complementary domain, the (Q)m may be 5'-GUUUUAGAGCUGUGUU-GUUUCG-3'(SEQ ID NO: 51), or a base sequence having at least 50% or more homology with 5'-GUUUUAGAGCU-GUGUUGUUUCG-3'(SEQ ID NO: 51).

In addition, each of the (X)a, (X)b and (X)c is selectively an additional base sequence, where the X may be each independently selected from the group consisting of A, U, C and G, and each of the a, b and c may be the number of bases, which is 0 or an integer of 1 to 20.

Second Strand

The second strand may consist of a second complementary domain and a proximal domain, and selectively include a tail domain.

Second Complementary Domain

In the second strand, the second complementary domain includes a nucleic acid sequence complementary to the first complementary domain of the first strand, and has enough complementarity so as to form a double strand with the first complementary domain. The second complementary domain may include a base sequence complementary to the first complementary domain and a base sequence not complementary to the first complementary domain, for example, a base sequence not forming a double strand with the first complementary domain, and may have a longer base sequence than the first complementary domain.

Here, the second complementary domain may be a 5 to 35-base sequence, or include a 5 to 35-base sequence. For example, the second complementary domain may be or include a 5, 6, 7, 8, 9, 10, 11, 12, 13, 14, 15, 16, 17, 18, 19, 20, 21, 22, 23, 24 or 25-base sequence, but the present invention is not limited thereto.

The second complementary domain may have homology with a natural second complementary domain, or may be derived from a natural second complementary domain. In addition, the second complementary domain may have a difference in base sequence thereof according to a species existing in nature, may be derived from a second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of *Streptococcus pyogenes, Campylobacter jejuni, Streptococcus thermophilus, Staphylococcus aureus* or *Neisseria meningitides*, or a second complementary domain derived therefrom.

Selectively, the second complementary domain may further include an additional base sequence which does not undergo complementary bonding with the first complementary domain of the first strand.

Here, the additional base sequence may be a 1 to 25-base sequence. For example, the additional base sequence may be a 1 to 5, 5 to 10, 10 to 15, 15 to 20 or 20 to 25-base sequence.

Proximal Domain

In the second strand, the proximal domain is a sequence of 1 to 20 bases, and a domain located at the 3' end direction of the second complementary domain. For example, the proximal domain may be or include a sequence of 5, 6, 7, 8, 8, 9, 10, 11, 12, 13, 14 or 15 bases.

Here, the proximal domain may have a double strand bond between complementary base sequences therein.

In addition, the proximal domain may have homology with a natural proximal domain, or may be derived from a natural proximal domain. In addition, the proximal domain may have a difference in base sequence according to a species existing in nature, may be derived from a proximal domain of a species existing in nature, or may have partial or complete homology with the proximal domain of a species existing in nature.

In one exemplary embodiment, the proximal domain may have partial, that is, at least 50% or more, or complete homology with a proximal domain of *Streptococcus pyogenes, Campylobacter jejuni, Streptococcus thermophilus, Staphylococcus aureus* or *Neisseria meningitides*, or a proximal domain derived therefrom.

Tail Domain

Selectively, in the second strand, the tail domain may be a domain selectively added to the 3' end of the second strand, and the tail domain may be or include a 1 to 50-base sequence. For example, the tail domain may be or include a 1 to 5, 5 to 10, 10 to 15, 15 to 20, 20 to 25, 25 to 30, 30 to 35, 35 to 40, 40 to 45 or 45 to 50-base sequence.

Here, the tail domain may have a double strand bond between complementary base sequences therein.

In addition, the tail domain may have homology with a natural tail domain, or may be derived from a natural tail domain. In addition, the tail domain may have a difference in base sequence according to a species existing in nature, may be derived from a tail domain contained in the species existing in nature, or may have partial or complete homology with the tail domain contained in the species existing in nature.

In one exemplary embodiment, the tail domain may have partial, that is, at least 50% or more, or complete homology with a tail domain of *Streptococcus pyogenes, Campylobacter jejuni, Streptococcus thermophilus, Staphylococcus aureus* or *Neisseria meningitides*, or a tail domain derived therefrom.

In another embodiment, the tail domain may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of each of the base sequence of the second complementary domain, the proximal domain and/or the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the second strand may consist of 5'-[second complementary domain]-[proximal domain]-3' or 5'-[second complementary domain]-[proximal domain]-[tail domain]-3' as described above.

In addition, the second strand may selectively include an additional base sequence.

In one exemplary embodiment, the second strand may be 5'-(Z)h-(P)k-3'; or 5'-(X)d-(Z)h-(X)e-(P)k-(X)f-3'.

In another embodiment, the second strand may be 5'-(Z)h-(P)k-(F)i-3'; or 5'-(X)d-(Z)h-(X)e-(P)k-(X)f-(F)i-3'.

Here, the (Z)h is a base sequence including a second complementary domain, which is able to form a complementary bond with the first complementary domain of the first strand. The (Z)h may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Streptococcus pyogenes* or a second complementary domain derived therefrom, the (Z)h may be 5'-UAGCAAGUUAAAAU-3'(SEQ ID NO: 44), or a base sequence having at least 50% or more homology with 5'-UAGCAAGUUAAAAU-3'(SEQ ID NO: 44).

In another example, when the second complementary domain has partial or complete homology with a second complementary domain of *Campylobacter jejuni* or a second complementary domain derived therefrom, the (Z)h may be 5'-AAGAAAUUUAAAAAGGGACUAAAAU-3'(SEQ ID NO: 45), or a base sequence having at least 50% or more homology with 5'-AAGAAAUUUAAAAAGGGAC-UAAAAU-3'(SEQ ID NO: 45).

In still another example, when the second complementary domain has partial or complete homology with a second complementary domain of *Streptococcus thermophilus* or a second complementary domain derived therefrom, the (Z)h may be 5'-CGAAACAACACAGCGAGUUAAAAU-3' (SEQ ID NO: 52), or a base sequence having at least 50% or more homology with 5'-CGAAACAACACAGCGAGUUAAAAU-3'(SEQ ID NO: 52).

The (P)k is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the (P)k may be 5'-AAGGCUAGUCCG-3'(SEQ ID NO: 47), or a base sequence having at least 50% or more homology with 5'-AAGGCUAGUCCG-3'(SEQ ID NO: 47).

In another example, when the proximal domain has partial or complete homology with a proximal domain of *Campylobacter jejuni* or a proximal domain derived therefrom, the (P)k may be 5'-AAAGAGUUUGC-3'(SEQ ID NO: 48), or a base sequence having at least 50% or more homology with 5'-AAAGAGUUUGC-3'(SEQ ID NO: 48).

In still another example, when the proximal domain has partial or complete homology with a proximal domain of *Streptococcus thermophilus* or a proximal domain derived therefrom, the (P)k may be 5'-AAGGCUUAGUCCG-3' (SEQ ID NO: 53), or a base sequence having at least 50% or more homology with 5'-AAGGCUUAGUCCG-3'(SEQ ID NO: 53).

The (F)i may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)i may be 5'-UUAU-CAACUUGAAAAAGUGGCACCGAGUCGGUGC-3' (SEQ ID NO: 49), or a base sequence having at least 50% or more homology with 5'-UUAUCAAC-UUGAAAAAGUGGCACCGAGUCGGUGC-3'(SEQ ID NO: 49).

In another example, when the tail domain has partial or complete homology with a tail domain of *Campylobacter jejuni* or a tail domain derived therefrom, the (F)i may be 5'-GGGACUCUGCGGGGUUACAAUCCCC-UAAAACCGCUUUU-3'(SEQ ID NO: 50), or a base sequence having at least 50% or more homology with 5'-GGGACUCUGCGGGGUUACAAUCCCC-UAAAACCGCUUUU-3'(SEQ ID NO: 50).

In still another example, when the tail domain has partial or complete homology with a tail domain of *Streptococcus thermophilus* or a tail domain derived therefrom, the (F)i may be 5'-UACUCAACUUGAAAAG-GUGGCACCGAUUCGGUGUUUUU-3'(SEQ ID NO: 54), or a base sequence having at least 50% or more homology with 5'-UACUCAACUUGAAAAG-GUGGCACCGAUUCGGUGUUUUU-3'(SEQ ID NO: 54).

In addition, the (F)i may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)d, (X)e and (X)f may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into two types.
i) Single-Stranded gRNA

First, there is single-stranded gRNA in which a first strand or a second strand of the double-stranded gRNA is linked by a linker domain, and here, the single-stranded gRNA consists of 5'-[first strand]-[linker domain]-[second strand]-3'.

Specifically, the single-stranded gRNA may consist of
5'-[guide domain]-[first complementary domain]-[linker domain]-[second complementary domain]-[proximal domain]-3' or
5'-[guide domain]-[first complementary domain]-[linker domain]-[second complementary domain]-[proximal domain]-[tail domain]-3'.

Each domain except the linker domain is the same as the description of each domain of the first and second strands of the double-stranded gRNA.

Linker Domain

In the single-stranded gRNA, the linker domain is a domain connecting a first strand and a second strand, and specifically, is a nucleic acid sequence which connects a first complementary domain with a second complementary domain to produce single-stranded gRNA. Here, the linker domain may be connected with the first complementary domain and the second complementary domain by covalent bonding or non-covalent bonding, or connect the first complementary domain with the second complementary domain by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

The linker domain is suitable to be used in a single-stranded gRNA molecule, and may be connected with the first strand and the second strand of the double-stranded gRNA, or connect the first strand with the second strand by covalent or non-covalent bonding to be used in production of the single-stranded gRNA. The linker domain may be connected with crRNA and tracrRNA of the double-stranded gRNA, or connect crRNA with tracrRNA by covalent or non-covalent bonding to be used in production of the single-stranded gRNA.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3' as described above.

In addition, the single-stranded gRNA may selectively include an additional base sequence.

In one exemplary embodiment, the single-stranded gRNA may be

5'-(N$_{target}$)-(Q)$_m$-(L)$_i$-(Z)$_h$-(P)$_k$-3'; or
5'-(N$_{target}$)-(Q)$_m$-(L)$_i$-(Z)$_h$-(P)$_k$-(F)$_i$-3'.

In another embodiment, the single-stranded gRNA may be

5'-(X)$_a$-(N$_{target}$)-(X)$_b$-(Q)$_m$-(X)$_c$-(L)$_i$-(X)$_d$-(Z)$_h$-(X)$_e$-(P)$_k$-(X)$_f$-3'; or
5'-(X)$_a$-(N$_{target}$)-(X)$_b$-(Q)$_m$-(X)$_c$-(L)$_i$-(X)$_d$-(Z)$_h$-(X)$_e$-(P)$_k$-(X)$_f$-(F)$_i$-3'.

Here, the Ntarget is a base sequence capable of forming a complementary bond with a target sequence on a target gene or nucleic acid, and a base sequence region capable of being changed according to a target sequence on a target gene or nucleic acid.

In one exemplary embodiment, Ntarget is a base sequence capable of forming a complementary bond with a target gene, that is, a target sequence of an unsaturated fatty acid biosynthesis-associated factor such as an FAD gene, preferably an FAD2 gene, an FAD3 gene, an FAD6 gene, an FAD7 gene, or an FAD8 gene.

The (Q)m includes a base sequence including the first complementary domain, which is able to form a complementary bond with a second complementary domain. The (Q)m may be a sequence having partial or complete homology with a first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a first complementary domain derived therefrom, the (Q)m may be 5'-GUUUUA-GAGCUA-3'(SEQ ID NO: 42), or a base sequence having at least 50% or more homology with 5'-GUUUUAGAGCUA-3'(SEQ ID NO: 42).

In another example, when the first complementary domain has partial or complete homology with a first complementary domain of *Campylobacter jejuni* or a first complementary domain derived therefrom, the (Q)m may be 5'-GUUUUAGUCCCUUUUUAAAUUUCUU-3'(SEQ ID NO: 43), or a base sequence having at least 50% or more homology with 5'-GUUUUAGUCCC-UUUUUAAAUUUCUU-3'(SEQ ID NO: 43).

In still another example, when the first complementary domain has partial or complete homology with a first complementary domain of *Streptococcus thermophilus* or a first complementary domain derived therefrom, the (Q)m may be 5'-GUUUUAGAGCUGUGUUGUUUCG-3'(SEQ ID NO: 51), or a base sequence having at least 50% or more homology with 5'-GUUUUAGAGCUGUGUUGUUUCG-3'(SEQ ID NO: 51).

In addition, the (L)j is a base sequence including the linker domain, and connecting the first complementary domain with the second complementary domain, thereby producing single-stranded gRNA. Here, the L may be each independently selected from the group consisting of A, U, C and G, and the j may be the number of bases, which is an integer of 1 to 30.

The (Z)h is a base sequence including the second complementary domain, which is able to have a complementary bond with the first complementary domain. The (Z)h may be a sequence having partial or complete homology with the second complementary domain of a species existing in nature, and the base sequence of the second complementary domain may be changed according to the species of origin. The Z may be each independently selected from the group consisting of A, U, C and G, and the h is the number of bases, which may be an integer of 5 to 50.

For example, when the second complementary domain has partial or complete homology with a second complementary domain of *Streptococcus pyogenes* or a second complementary domain derived therefrom, the (Z)h may be 5'-UAGCAAGUUAAAAU-3'(SEQ ID NO: 44), or a base sequence having at least 50% or more homology with 5'-UAGCAAGUUAAAAU-3'(SEQ ID NO: 44).

In another example, when the second complementary domain has partial or complete homology with a second complementary domain of *Campylobacter jejuni* or a second complementary domain derived therefrom, the (Z)h may be 5'-AAGAAAUUUAAAAAGGGACUAAAAU-3'(SEQ ID NO: 45), or a base sequence having at least 50% or more homology with 5'-AAGAAAUUUAAAAAGGGAC-UAAAAU-3'(SEQ ID NO: 45).

In still another example, when the second complementary domain has partial or complete homology with a second complementary domain of *Streptococcus thermophilus* or a second complementary domain derived therefrom, the (Z)h may be 5'-CGAAACAACACAGCGAGUUAAAAU-3' (SEQ ID NO: 52), or a base sequence having at least 50% or more homology with 5'-CGAAACAACACAGCGAGUUAAAAU-3'(SEQ ID NO: 52).

The (P)k is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the (P)k may be 5'-AAGGCUAGUCCG-3'(SEQ ID NO: 47), or a base sequence having at least 50% or more homology with 5'-AAGGCUAGUCCG-3'(SEQ ID NO: 47).

In another example, when the proximal domain has partial or complete homology with a proximal domain of *Campylobacter jejuni* or a proximal domain derived therefrom, the (P)k may be 5'-AAAGAGUUUGC-3'(SEQ ID NO: 48), or a base sequence having at least 50% or more homology with 5'-AAAGAGUUUGC-3'(SEQ ID NO: 48).

In still another example, when the proximal domain has partial or complete homology with a proximal domain of *Streptococcus thermophilus* or a proximal domain derived therefrom, the (P)k may be 5'-AAGGCUUAGUCCG-3' (SEQ ID NO: 53), or a base sequence having at least 50% or more homology with 5'-AAGGCUUAGUCCG-3'(SEQ ID NO: 53).

The (F)i may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)i may be 5'-UUAU-CAACUUGAAAAAGUGGCACCGAGUCGGUGC-3' (SEQ ID NO: 49), or a base sequence having at least 50% or more homology with 5'-UUAUCAAC-UUGAAAAAGUGGCACCGAGUCGGUGC-3'(SEQ ID NO: 49).

In another example, when the tail domain has partial or complete homology with a tail domain of *Campylobacter jejuni* or a tail domain derived therefrom, the (F)i may be 5'-GGGACUCUGCGGGGUUACAAUCCCC-UAAAACCGCUUUU-3' (SEQ ID NO: 50), or a base sequence having at least 50% or more homology with 5'-GGGACUCUGCGGGGUUACAAUCCCC-UAAAACCGCUUUU-3'(SEQ ID NO: 50).

In still another example, when the tail domain has partial or complete homology with a tail domain of *Streptococcus thermophilus* or a tail domain derived therefrom, the (F)i may be 5'-UACUCAACUUGAAAAG-GUGGCACCGAUUCGGUGUUUUU-3'(SEQ ID NO: 54), or a base sequence having at least 50% or more homology with 5'-UACUCAACUUGAAAAG-GUGGCACCGAUUCGGUGUUUUU-3'(SEQ ID NO: 54).

In addition, the (F)i may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)a, (X)b, (X)c, (X)d, (X)e and (X)f may be base sequences selectively added, where the X may be each independently selected from the group consisting of A, U, C and G, and each of the a, b, c, d, e and f may be the number of bases, which is 0 or an integer of 1 to 20.

ii) Single-Stranded gRNA

Second, the single-stranded gRNA may be single-stranded gRNA consisting of a guide domain, a first complementary domain and a second complementary domain, and here, the single-stranded gRNA may consist of:

5'-[second complementary domain]-[first complementary domain]-[guide domain]-3'; or 5'-[second complementary domain]-[linker domain]-[first complementary domain]-[guide domain]-3'.

Guide Domain

In the single-stranded gRNA, the guide domain includes a complementary guide sequence capable of forming a complementary bond with a target sequence on a target gene or nucleic acid. The guide sequence may be a nucleic acid sequence having complementarity to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be or include a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence capable of forming a complementary bond with a target sequence on a target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of an unsaturated fatty acid biosynthesis-associated factor such as an FAD gene, preferably an FAD2 gene, an FAD3 gene, an FAD6 gene, an FAD7 gene or an FAD8 gene, which has, for example, at least 70%, 75%, 80%, 85%, 90% or 95% or more complementarity or complete complementarity.

Here, the guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the FAD2 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the FAD3 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the FAD6 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the FAD7 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the FAD8 gene. The guide sequence may be or include a 5 to 50-base sequence. For example, the guide sequence may be or include a 16, 17, 18, 19, 20, 21, 22, 23, 24 or 25-base sequence.

Here, target sequences of the target genes, that is, the unsaturated fatty acid biosynthesis-associated factor such as the FAD2 gene for the guide sequence are listed above in Table 1, but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may be a single base sequence, guanine (G), or a sequence of two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain is a domain including a nucleic acid sequence complementary to the second complementary domain, and having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasiicus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas cre-*

*vioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *candidatus Methanoplasma termitum* or *Eubacterium eligens*, or a first complementary domain derived therefrom.

Selectively, the first complementary domain may include an additional base sequence which does not undergo complementary bonding with the second complementary domain.

Here, the additional base sequence may be a 1 to 15-base sequence. For example, the additional base sequence may be a 1 to 5, 5 to 10, or 10 to 15-base sequence.

Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be or include a 5 to 35-base sequence. For example, the second complementary domain may be a 5, 6, 7, 8, 9, 10, 11, 12, 13, 14, 15, 16, 17, 18, 19, 20, 21, 22, 23, 24 or 25-base sequence.

The second complementary domain may have homology with a natural second complementary domain, or may be derived from the natural second complementary domain. In addition, the second complementary domain may have a difference in base sequence of the second complementary domain according to a species existing in nature, and may be derived from second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of Parcubacteria bacterium (GWC2011_GWC2_44_17), Lachnospiraceae bacterium (MC2017), *Butyrivibrio proteoclasiicus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smiihella* sp. (SC_KO8D17), *Leptospira inadai*, Lachnospiraceae bacterium (MA2020), *Francisella novicida* (U112), *candidatus Methanoplasma termitum* or *Eubacterium eligens*, or a second complementary domain derived therefrom.

Selectively, the second complementary domain may include an additional base sequence which does not undergo complementary bonding with the first complementary domain.

Here, the additional base sequence may be a 1 to 15-base sequence. For example, the additional base sequence may be a 1 to 5, 5 to 10, or 10 to 15-base sequence.

Linker Domain

Selectively, the linker domain is a nucleic acid sequence connecting a first complementary domain with a second complementary domain to produce single-stranded gRNA. Here, the linker domain may be connected with the first complementary domain and the second complementary domain by covalent or non-covalent bonding, or may connect the first and second complementary domains by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

Selectively, a part or all of the base sequence of the guide domain, the first complementary domain, the second complementary domain and the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[second complementary domain]-[first complementary domain]-[guide domain]-3' or 5'-[second complementary domain]-[linker domain]-[first complementary domain]-[guide domain]-3' as described above.

In addition, the single-stranded gRNA may selectively include an additional base sequence.

In one exemplary embodiment, the single-stranded gRNA may be

5'-$(Z)_h$-$(Q)_m$-$(N_{target})$-3'; or
5'-$(X)_a$-$(Z)_h$-$(X)_b$-$(Q)_m$-$(X)_c$-$(N_{target})$-3'.

In another embodiment, the single-stranded gRNA may be

5'-$(Z)_h$-$(L)_j$-$(Q)_m$-$(N_{target})$-3'; or
5'-$(X)_a$-$(Z)_h$-$(L)_j$-$(Q)_m$-$(X)_c$-$(N_{target})$-3'.

Here, the Ntarget is a base sequence capable of forming a complementary bond with a target sequence on a target gene or nucleic acid, and a base sequence region which may be changed according to a target sequence on a target gene or nucleic acid.

In one exemplary embodiment, Ntarget may be a base sequence capable of forming a complementary bond with a target gene, that is, a target sequence of an unsaturated fatty acid biosynthesis-associated factor such as an FAD gene, preferably an FAD2 gene, an FAD3 gene, an FAD6 gene, an FAD7 gene or an FAD8 gene.

The $(Q)_m$ is a base sequence including the first complementary domain, which is able to form a complementary bond with the second complementary domain of the second strand. The $(Q)_m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of Parcubacteria bacterium or a first complementary domain derived therefrom, the $(Q)_m$ may be 5'-UUUGUAGAU-3', or a base sequence having at least 50% or more homology with 5'-UUUGUAGAU-3'.

The $(Z)_h$ is a base sequence including a second complementary domain, which is able to form a complementary bond with the first complementary domain of the first strand. The $(Z)_h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of Parcubacteria bacterium or a Parcubacteria bacterium-derived second complementary domain, the (Z)h may be 5'-AAAUUUCUACU-3'(SEQ ID NO: 46), or a base sequence having at least 50% or more homology with 5'-AAAUUUCUACU-3'(SEQ ID NO: 46).

In addition, the (L)j is a base sequence including the linker domain, which connects the first complementary domain with the second complementary domain. Here, the L may be each independently selected from the group consisting of A, U, C and G, and the j may be the number of bases, which is an integer of 1 to 30.

In addition, each of the (X)a, (X)b and (X)c is selectively an additional base sequence, where the X may be each independently selected from the group consisting of A, U, C and G, and the a, b and c may be the number of bases, which is 0 or an integer of 1 to 20.

2. Editor Protein

An editor protein refers to a peptide, polypeptide or protein which is able to directly bind to or interact with, without direct binding to, a nucleic acid.

The nucleic acid may be a nucleic acid contained in a target nucleic acid, gene or chromosome.

The nucleic acid may be a guide nucleic acid.

The editor protein may be an enzyme.

The editor protein may be a fusion protein.

Here, the fusion protein refers to a protein produced by fusing an enzyme with an additional domain, peptide, polypeptide or protein.

The enzyme refers to a protein including a domain which is able to cleave a nucleic acid, gene, chromosome or protein.

The enzyme may be a nuclease, protease or restriction enzyme.

The additional domain, peptide, polypeptide or protein may be a functional domain, peptide, polypeptide or protein, which has a function the same as or different from the enzyme.

The fusion protein may include an additional domain, peptide, polypeptide or protein at one or more of an N-terminus of an enzyme or the proximity thereof; a C-terminus of the enzyme or the proximity thereof; the middle region of an enzyme; and a combination thereof.

The fusion protein may include a functional domain, peptide, polypeptide or protein at one or more of an N-terminus of an enzyme or the proximity thereof; a C-terminus of the enzyme or the proximity thereof; the middle region of an enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV(SEQ ID NO: 55); NLS derived from nucleoplasmin (e.g., nucleoplasmin bipartite NLS with a sequence KRPAATKKAGQAKKKK(SEQ ID NO: 56)); c-myc NLS with an amino acid sequence PAAKRVKLD(SEQ ID NO: 57) or RQRRNELKRSP(SEQ ID NO: 58); hRNPA1 M9 NLS with a sequence NQSSNFGPMKGGNFGGRSSGPYGGGGQYFAK-PRNQGGY(SEQ ID NO: 59); an importin-α-derived IBB domain sequence RMRIZFKNKGKDTAELRRRRVEVS-VELRKAKKDEQILKRRNV(SEQ ID NO: 60); myoma T protein sequences VSRKRPRP(SEQ ID NO: 61) and PPK-KARED(SEQ ID NO: 62); human p53 sequence PQPKKKPL(SEQ ID NO: 63); a mouse c-abl IV sequence SALIKKKKMAP(SEQ ID NO: 64); influenza virus NS1 sequences DRLRR and PKQKKRK(SEQ ID NO: 66); a hepatitis virus-δ antigen sequence RKLKKKIKKL(SEQ ID NO: 67); a mouse Mx1 protein sequence REKKKFLKRR (SEQ ID NO: 68); a human poly(ADP-ribose) polymerase sequence KRKGDEVDGVDEVAKKKSKK(SEQ ID NO: 69); or steroid hormone receptor (human) glucocorticoid sequence RKCLQAGMNLEARKTKK(SEQ ID NO: 70), but the present invention is not limited thereto.

The editor protein may include a complete active enzyme.

Here, the "complete active enzyme" refers to an enzyme having the same function as a function of a wild-type enzyme, and for example, the wild-type enzyme cleaving the double strand of DNA has complete enzyme activity of entirely cleaving the double strand of DNA.

In addition, the complete active enzyme includes an enzyme having an improved function compared to the function of the wild-type enzyme, and for example, a specific modification or manipulation type of the wild-type enzyme cleaving the double strand of DNA has full enzyme activity which is improved compared to the wild-type enzyme, that is, activity of cleaving the double strand of DNA.

The editor protein may include an incomplete or partially active enzyme.

Here, the "incomplete or partially active enzyme" refers to an enzyme having some of the functions of the wild-type enzyme, and for example, a specific modification or manipulation type of the wild-type enzyme cleaving the double strand of DNA has incomplete or partial enzyme activity of cleaving a part of the double strand, that is, a single strand of DNA.

The editor protein may include an inactive enzyme.

Here, the "inactive enzyme" refers to an enzyme in which the function of a wild-type enzyme is completely inactivated. For example, a specific modification or manipulation type of the wild-type enzyme cleaving the double strand of DNA has inactivity so as not to completely cleave the DNA double strand.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

As one exemplary embodiment of the editor protein of the present invention, a CRISPR enzyme will be described below.

CRISPR Enzyme

The term "CRISPR enzyme" is a main protein component of a CRISPR-Cas system, and forms a complex with gRNA, resulting in the CRISPR-Cas system.

The CRISPR enzyme is a nucleic acid or polypeptide (or a protein) having a sequence encoding the CRISPR enzyme, and representatively, a Type II CRISPR enzyme or Type V CRISPR enzyme is widely used.

The Type II CRISPR enzyme is Cas9, which may be derived from various microorganisms such as *Streptococcus pyogenes, Streptococcus thermophilus, Streptococcus sp., Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas sp., Crocosphaera watsonii, Cyanothece sp., Microcystis aeruginosa, Synechococcus sp., Acetohalobium arabaticum, Ammonifex degensii, Caldicelulosiruptor bescii, candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter sp., Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc sp., Arthrospira maxima, Arthrospira platensis, Arthrospira sp., Lyngbya sp., Microcoleus chthonoplastes, Oscillatoria sp., Petrotoga mobilis, Thermosipho africanus* and *Acaryochloris marina*.

The term "Cas9" is an enzyme which binds to gRNA so as to cleave or modify a target sequence or position on a target gene or nucleic acid, and may consist of an HNH domain capable of cleaving a nucleic acid strand forming a complementary bond with gRNA, an RuvC domain capable of cleaving a nucleic acid strand forming a complementary bond with gRNA, an REC domain recognizing a target and a PI domain recognizing PAM. Hiroshi Nishimasu et al. (2014) Cell 156:935-949 may be referenced for specific structural characteristics of Cas9.

In addition, the Type V CRISPR enzyme may be Cpf1, which may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacillus, Methylobacterium* or *Acidaminococcus*.

The Cpf1 may consist of an RuvC domain similar and corresponding to the RuvC domain of Cas9, an Nuc domain without the HNH domain of Cas9, an REC domain recognizing a target, a WED domain and a PI domain recognizing PAM. For specific structural characteristics of Cpf1, Takashi Yamano et al. (2016) Cell 165:949-962 may be referenced.

The CRISPR enzyme of the Cas9 or Cpf1 protein may be isolated from a microorganism existing in nature or non-naturally produced by a recombinant or synthetic method.

Type II CRISPR Enzyme

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, or the HNH domain is used to include HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII. For example, in the case of SpCas9, the RuvC domain is assembled from each of three divided RuvC domains (RuvC I, RuvCII and RuvCIII) located at the sequences of amino acids 1 to 59, 718 to 769 and 909 to 1098 of SpCas9, respectively.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs. For example, in the case of SpCas9, the HNH domain is located at amino acid sequence 775 to 908 of SpCas9.

The PI domain recognizes a specific base sequence in a target gene or nucleic acid, that is, a protospacer adjacent motif (PAM) or interacts with PAM. For example, in the case of SpCas9, the PI domain is located at the sequence of amino acids 1099 to 1368 of SpCas9.

Here, the PAM may vary according to the origin of the type II CRISPR enzyme. For example, when the CRISPR enzyme is SpCas9, PAM may be 5'-NGG-3', when the CRISPR enzyme is *Streptococcus thermophilus* Cas9 (StCas9), PAM may be 5'-NNAGAAW-3'(W=A or T), when the CRISPR enzyme is *Neisseria meningitides* Cas9 (NmCas9), PAM may be 5'-NNNNGATT-3', and when the CRISPR enzyme is *Campylobacter jejuni* Cas9 (CjCas9), PAM may be 5'-NNNVRYAC-3' (V=G or C or A, R=A or G, Y=C or T), where the N may be A, T, G or C; or A, U, G or C.

Type V CRISPR Enzyme

Type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence.

The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species.

In one example, the PAM sequence recognized by Cpf1 may be 5'-TTN-3' (N is A, T, C or G).

CRISPR Enzyme Activity

A CRISPR enzyme cleaves a double or single strand of a target gene or nucleic acid, and has nuclease activity causing breakage or deletion of the double or single strand. Generally, the wild-type type II CRISPR enzyme or type V CRISPR enzyme cleaves the double strand of the target gene or nucleic acid.

To manipulate or modify the above-described nuclease activity of the CRISPR enzyme, the CRISPR enzyme may be manipulated or modified, such a manipulated or modified CRISPR enzyme may be modified into an incompletely or partially active or inactive enzyme.

Incompletely or Partially Active Enzyme

A CRISPR enzyme modified to change enzyme activity, thereby exhibiting incomplete or partial activity is called a nickase.

The term "nickase" refers to a CRISPR enzyme manipulated or modified to cleave only one strand of the double strand of the target gene or nucleic acid, and the nickase has nuclease activity of cleaving a single strand, for example, a strand that is not complementary or complementary to gRNA of the target gene or nucleic acid. Therefore, to cleave the double strand, nuclease activity of the two nickases is needed.

For example, the nickase may have nuclease activity by the RuvC domain. That is, the nickase may include nuclease activity of the HNH domain, and to this end, the HNH domain may be manipulated or modified.

In one example, provided that the CRISPR enzyme is the type II CRISPR enzyme, in the case of SpCas9, when the residue 840 in the amino acid sequence of SpCas9 is mutated from histidine to alanine, the nuclease activity of the HNH domain is inactivated to be used as a nickase. Since the nickase produced thereby has nuclease activity of the RuvC domain, it is able to cleave a strand which does not form a complementary bond with a non-complementary strand of the target gene or nucleic acid, that is, gRNA.

In another exemplary embodiment, in the case of CjCas9, when the residue 559 in the amino acid sequence of CjCas9 is mutated from histidine to alanine, the nuclease activity of the HNH domain is inactivated to be used as a nickase. The nickase produced thereby has nuclease activity by the RuvC domain, and thus is able to cleave a non-complementary strand of the target gene or nucleic acid, that is, a strand that does not form a complementary bond with gRNA.

For example, the nickase may have nuclease activity by the HNH domain. That is, the nickase may include the nuclease activity of the RuvC domain, and to this end, the RuvC domain may be manipulated or modified.

In one example, provided that the CRISPR enzyme is the type II CRISPR enzyme, in one exemplary embodiment, in the case of SpCas9, when the residue 10 in the amino acid sequence of SpCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

In another exemplary embodiment, in the case of CjCas9, when the residue 8 in the amino acid sequence of CjCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

Inactive Enzyme

A CRISPR enzyme which is modified to make enzyme activity completely inactive is called an inactive CRISPR enzyme.

The term "inactive CRISPR enzyme" refers to a CRISPR enzyme which is modified not to completely cleave the double strand of the target gene or nucleic acid, and the inactive CRISPR enzyme has nuclease inactivity due to the mutation in the domain with nuclease activity of the wild-type CRISPR enzyme. The inactive CRISPR enzyme may be one in which the nuclease activities of the RuvC domain and the HNH domain are inactivated.

For example, the inactive CRISPR enzyme may be manipulated or modified in the RuvC domain and the HNH domain so as to inactive nuclease activity.

In one example, provided that the CRISPR enzyme is the type II CRISPR enzyme, in one exemplary embodiment, in the case of SpCas9, when the residues 10 and 840 in the amino acid sequence of SpCas9 are mutated from aspartic acid and histidine to alanine, respectively, nuclease activities by the RuvC domain and the HNH domain are inactivated, such that the double strand may not cleave completely the double strand of the target gene or nucleic acid.

In another exemplary embodiment, in the case of CjCas9, when the residues 8 and 559 in the amino acid sequence of CjCas9 are mutated from aspartic acid and histidine to alanine, the nuclease activities by the RuvC domain and the HNH domain are inactivated, such that the double strand may not cleave completely the double strand of the target gene or nucleic acid.

Other Activities

The CRISPR enzyme may have endonuclease activity, exonuclease activity or helicase activity, that is, an ability to anneal the helix structure of the double-stranded nucleic acid, in addition to the above-described nuclease activity.

In addition, the CRISPR enzyme may be modified to completely, incompletely, or partially activate the endonuclease activity, exonuclease activity or helicase activity.

Targeting of CRISPR Enzyme

The CRISPR enzyme may interact with gRNA, thereby forming a gRNA-CRISPR enzyme complex, that is, a CRISPR complex, and lead a guide sequence to approach a target sequence including a PAM sequence in cooperation with gRNA. Here, the ability of the CRISPR enzyme to interact with the target gene or nucleic acid is dependent on the PAM sequence.

The PAM sequence is a sequence present in the target gene or nucleic acid, which may be recognized by the PI domain of the CRISPR enzyme. The PAM sequence may vary depending on the origin of the CRISPR enzyme. That is, there are various PAM sequences which are able to be specifically recognized according to species.

In one example, provided that the CRISPR enzyme is the type II CRISPR enzyme, in the case of SpCas9, the PAM sequence may be 5'-NGG-3', 5'-NAG-3' and/or 5'-NGA-3', in the case of StCas9, the PAM sequence may be 5'-NGGNG-3' and/or 5'-NNAGAAW-3' (W=A or T), in the case of NmCas9, the PAM sequence may be 5'-NNNNGATT-3' and/or 5'-NNNGCTT-3', in the case of CjCas9, the PAM sequence may be 5'-NNNVRYAC-3' (V=G, C or A; R=A or G; Y=C or T), in the case of *Streptococcus mutans* Cas9 (SmCas9), the PAM sequence may be 5'-NGG-3' and/or 5'-NAAR-3' (R=A or G), and in the case of *Staphylococcus aureus* Cas9 (SaCas9), the PAM sequence may be 5'-NNGRR-3', 5'-NNGRRT-3' and/or 5'-NNGRRV-3' (R=A or G; V=G, C or A).

In another example, provided that the CRISPR enzyme is the type V CRISPR enzyme, in the case of Cpf1, the PAM sequence may be 5'-TTN-3'. Here, the N may be A, T, G or C; or A, U, G or C.

The CRISPR enzyme capable of recognizing a specific PAM sequence may be manipulated or modified using the PAM sequence capable of being specifically recognized according to species. For example, the PI domain of SpCas9 may be replaced with the PI domain of CjCas9 so as to have the nuclease activity of SpCas9 and recognize a CjCas9-specific PAM sequence, thereby producing SpCas9 recognizing the CjCas9-specific PAM sequence. A specifically recognized PAM sequence may be changed by substitution or replacement of the PI domain.

CRISPR Enzyme Mutant

The CRISPR enzyme may be modified to improve or inhibit various characteristics such as nuclease activity, helicase activity, an ability to interact with gRNA, and an ability to approach the target gene or nucleic acid, for example, PAM recognizing ability of the CRISPR enzyme.

In addition, the CRISPR enzyme mutant may be a CRISPR enzyme which interacts with gRNA to form a gRNA-CRISPR enzyme complex, that is, a CRISPR complex, and is modified or manipulated to improve target specificity, when approaching or localized to the target gene or nucleic acid, such that only a double or single strand of the target gene or nucleic acid is cleaved without cleavage of a double or single strand of a non-target gene or nucleic acid which partially forms a complementary bond with gRNA and a non-target gene or nucleic acid which does not form a complementary bond therewith.

Here, an effect of cleaving the double or single strand of the non-target gene or nucleic acid partially forming a complementary bond with gRNA and the non-target gene or nucleic acid not forming a complementary bond therewith is referred to as an off-target effect, a position or base sequence of the non-target gene or nucleic acid partially forming a complementary bond with gRNA and the non-target gene or nucleic acid not forming a complementary bond therewith is referred to as an off-target. Here, there may be one or more off-targets. One the other hand, the cleavage effect of the double or single strand of the target gene or nucleic acid is referred to as an on-target effect, and a location or target sequence of the target gene or nucleic acid is referred to as an on-target.

The CRISPR enzyme mutant is modified in at least one of the amino acids of a naturally-occurring CRISPR enzyme, and may be modified, for example, improved or inhibited in one or more of the various characteristics such as nuclease activity, helicase activity, an ability to interact with gRNA, an ability to approach the target gene or nucleic acid and target specificity, compared to the unmodified CRISPR enzyme. Here, the modification may be substitution, removal, addition of an amino acid, or a mixture thereof.

In the CRISPR enzyme mutant, the modification may be a modification of one or two or more amino acids located in a region consisting of amino acids having positive charges, present in the naturally-occurring CRISPR enzyme.

For example, the modification may be a modification of one or two or more amino acids of the positively-charged amino acids such as lysine (K), arginine (R) and histidine (H), present in the naturally-occurring CRISPR enzyme.

The modification may be a modification of one or two or more amino acids located in a region composed of non-positively-charged amino acids present in the naturally-occurring CRISPR enzyme.

For example, the modification may be a modification of one or two or more amino acids of the non-positively-charged amino acids, that is, aspartic acid (D), glutamic acid (E), serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In another example, the modification may be a modification of one or two or more amino acids of non-charged amino acids, that is, serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one or two or more of the amino acids having hydrophobic residues present in the naturally-occurring CRISPR enzyme.

For example, the modification may be a modification of one or two or more amino acids of glycine (G), alanine (A), valine (V), isoleucine (I), leucine (L), methionine (M), phenylalanine (F), tyrosine (Y) and tryptophan (W), present in the naturally-occurring CRISPR enzyme.

The modification may be a modification of one or two or more of the amino acids having polar residues, present in the naturally-occurring CRISPR enzyme.

For example, the modification may be a modification of one or two or more amino acids of serine (S), threonine (T), asparagine (N), glutamine (Q), cysteine (C), proline (P), lysine (K), arginine (R), histidine (H), aspartic acid (D) and glutamic acid (E), present in the naturally-occurring CRISPR enzyme.

In addition, the modification may be a modification of one or two or more of the amino acids including lysine (K), arginine (R) and histidine (H), present in the naturally-occurring CRISPR enzyme.

For example, the modification may be a substitution of one or two or more of the amino acids including lysine (K), arginine (R) and histidine (H), present in the naturally-occurring CRISPR enzyme.

The modification may be a modification of one or two or more of the amino acids including aspartic acid (D) and glutamic acid (E), present in the naturally-occurring CRISPR enzyme.

For example, the modification may be a substitution of one or two or more of the amino acids including aspartic acid (D) and glutamic acid (E), present in the naturally-occurring CRISPR enzyme.

The modification may be a modification of one or two or more of the amino acids including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

For example, the modification may be a substitution of one or two or more of the amino acid including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (W), present in the naturally-occurring CRISPR enzyme.

In addition, the modification may be a modification of one, two, three, four, five, six, seven or more of the amino acids present in the naturally-occurring CRISPR enzyme.

In addition, in the CRISPR enzyme mutant, the modification may be a modification of one or two or more of the amino acids present in the RuvC domain of the CRISPR enzyme. Here, the RuvC domain may be an RuvCI, RuvCII or RuvCIII domain.

The modification may be a modification of one or two or more of the amino acids present in the HNH domain of the CRISPR enzyme.

The modification may be a modification of one or two or more of the amino acids present in the REC domain of the CRISPR enzyme.

The modification may be one or two or more of the amino acids present in the PI domain of the CRISPR enzyme.

The modification may be a modification of two or more of the amino acids contained in at least two or more domains of the REC, RuvC, HNH and PI domains of the CRISPR enzyme.

In one example, the modification may be a modification of two or more of the amino acids contained in the REC and RuvC domains of the CRISPR enzyme.

In one exemplary embodiment, in the SpCas9 mutant, the modification may be a modification of at least two or more of the A203, H277, G366, F539, I601, M763, D965 and F1038 amino acids contained in the REC and RuvC domains of SpCas9.

In another example, the modification may be a modification of two or more of the amino acids contained in the REC and HNH domains of the CRISPR enzyme.

In one exemplary embodiment, in the SpCas9 mutant, the modification may be a modification of at least two or more of the A203, H277, G366, F539, I601 and K890 amino acids contained in the REC and HNH domains of SpCas9.

In one example, the modification may be a modification of two or more of the amino acids contained in the REC and PI domains of the CRISPR enzyme.

In one exemplary embodiment, in the SpCas9 mutant, the modification may be a modification of at least two or more of the A203, H277, G366, F539, I601, T1102 and D1127 amino acids contained in the REC and PI domains of SpCas9.

In another example, the modification may be a modification of three or more of the amino acids contained in the REC, RuvC and HNH domains of the CRISPR enzyme.

In one exemplary embodiment, in the SpCas9 mutant, the modification may be a modification of at least three or more of the A203, H277, G366, F539, I601, M763, K890, D965 and F1038 amino acids contained in the REC, RuvC and HNH domains of SpCas9.

In one example, the modification may be a modification of three or more of the amino acids contained in the REC, RuvC and PI domains contained in the CRISPR enzyme.

In one exemplary embodiment, in the SpCas9 mutant, the modification may be a modification of at least three or more of the A203, H277, G366, F539, I601, M763, D965, F1038, T1102 and D1127 amino acids contained in the REC, RuvC and PI domains of SpCas9.

In another example, the modification may be a modification of three or more of the amino acids contained in the REC, HNH and PI domains of the CRISPR enzyme.

In one exemplary embodiment, in the SpCas9 mutant, the modification may be a modification of at least three or more of the A203, H277, G366, F539, I601, K890, T1102 and D1127 amino acids contained in the REC, HNH and PI domains of SpCas9.

In one example, the modification may be a modification of three or more of the amino acids contained in the RuvC, HNH and PI domains of the CRISPR enzyme.

In one exemplary embodiment, in the SpCas9 mutant, the modification may be a modification of at least three or more of the M763, K890, D965, F1038, T1102 and D1127 amino acids contained in the RuvC, HNH and PI domains of SpCas9.

In another example, the modification may be a modification of four or more of the amino acids contained in the REC, RuvC, HNH and PI domains of the CRISPR enzyme.

In one exemplary embodiment, in the SpCas9 mutant, the modification may be a modification of at least four or more of the A203, H277, G366, F539, I601, M763, K890, D965, F1038, T1102 and D1127 amino acids contained in the REC, RuvC, HNH and PI domains of SpCas9.

In addition, in the CRISPR enzyme mutant, the modification may be a modification of one or two or more of the amino acids participating in the nuclease activity of the CRISPR enzyme.

For example, in the SpCas9 mutant, the modification may be a modification of one or two or more of the group consisting of the amino acids D10, E762, H840, N854, N863 and D986, or one or two or more of the group consisting of the amino acids corresponding to other Cas9 orthologs.

The modification may be a modification for partially inactivating the nuclease activity of the CRISPR enzyme, and such a CRISPR enzyme mutant may be a nickase.

Here, the modification may be a modification for inactivating the nuclease activity of the RuvC domain of the CRISPR enzyme, and such a CRISPR enzyme mutant may not cleave a non-complementary strand of a target gene or nucleic acid, that is, a strand which does not form a complementary bond with gRNA.

In one exemplary embodiment, in the case of SpCas9, when residue 10 of the amino acid sequence of SpCas9 is mutated from aspartic acid to alanine, that is, when mutated to D10A, the nuclease activity of the RuvC domain is inactivated, and thus the SpCas9 may be used as a nickase. The nickase produced thereby may not cleave a non-complementary strand of the target gene or nucleic acid, that is, a strand that does not form a complementary bond with gRNA.

In another exemplary embodiment, in the case of CjCas9, when residue 8 of the amino acid sequence of CjCas9 is mutated from aspartic acid to alanine, that is, when mutated to D8A, the nuclease activity of the RuvC domain is inactivated, and thus the CjCas9 may be used as a nickase. The nickase produced thereby may not cleave a non-complementary strand of the target gene or nucleic acid, that is, a strand that does not form a complementary bond with gRNA.

In addition, here, the modification may be a modification for inactivating the nuclease activity of the HNH domain of the CRISPR enzyme, and such a CRISPR enzyme mutant may not cleave a complementary strand of the target gene or nucleic acid, that is, a strand forming a complementary bond with gRNA.

In one exemplary embodiment, in the case of SpCas9, when residue 840 of the amino acid sequence of SpCas9 is mutated from histidine to alanine, that is, when mutated to H840A, the nuclease activity of the HNH domain is inactivated, and thus the SpCas9 may be used as a nickase. The nickase produced thereby may not cleave a complementary strand of the target gene or nucleic acid, that is, a strand that forms a complementary bond with gRNA.

In another exemplary embodiment, in the case of CjCas9, when residue 559 of the amino acid sequence of CjCas9 is mutated from histidine to alanine, that is, when mutated to H559A, the nuclease activity of the HNH domain is inactivated, and thus the CjCas9 may be used as a nickase. The nickase produced thereby may not cleave a complementary strand of the target gene or nucleic acid, that is, a strand that forms a complementary bond with gRNA.

In addition, the modification may be a modification for completely inactivating the nuclease activity of the CRISPR enzyme, and such a CRISPR enzyme mutant may be an inactive CRISPR enzyme.

Here, the modification may be a modification for inactivating the nuclease activities of the RuvC and HNH domains of the CRISPR enzyme, and such a CRISPR enzyme mutant may does not cleave a double strand of the target gene or nucleic acid.

In one exemplary embodiment, in the case of SpCas9, when the residues 10 and 840 in the amino acid sequence of SpCas9 are mutated from aspartic acid and histidine to alanine, that is, mutated to D10A and H840A, respectively, the nuclease activities of the RuvC domain and the HNH domain are inactivated, the double strand of the target gene or nucleic acid may not be completely cleaved.

In another exemplary embodiment, in the case of CjCas9, when residues 8 and 559 of the amino acid sequence of CjCas9 are mutated from aspartic acid and histidine to alanine, that is, mutated to D8A and H559A, respectively, the nuclease activities by the RuvC and HNH domains are inactivated, and thus the double strand of the target gene or nucleic acid may not be completely cleaved.

In addition, the CRISPR enzyme mutant may further include an optionally functional domain, in addition to the innate characteristics of the CRISPR enzyme, and such a CRISPR enzyme mutant may have an additional characteristic in addition to the innate characteristics.

Here, the functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The functional domain, peptide, polypeptide or protein may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in base repair or editing of C into T or U, or G into A.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain may be a nuclear localization sequence or signal (NLS) or a nuclear export sequence or signal (NES).

In one example, the CRISPR enzyme may include one or more NLSs. Here, one or more NLSs may be included at an N-terminus of an CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV(SEQ ID NO: 55); NLS from nucleoplasmin (e.g., nucleoplasmin bipartite NLS having the sequence KRPAATKKAGQAKKKK(SEQ ID NO: 56)); c-myc NLS having the amino acid sequence PAAKRVKLD(SEQ ID NO: 57) or RQRRNELKRSP(SEQ ID NO: 58); hRNPA1 M9 NLS having the sequence NQSSNFGPMKGGNFGGRSSGPYGGGGQYFAK-PRNQGGY(SEQ ID NO: 59); the sequence RMRIZFKNKGKDTAELRRRRVEVSVELRKAKKD-EQILKRRNV(SEQ ID NO: 60) of the IBB domain from importin-α; the sequences VSRKRPRP(SEQ ID NO: 61) and PPKKARED(SEQ ID NO: 62) of a myoma T protein; the sequence PQPKKKPL(SEQ ID NO: 63) of human p53; the sequence SALIKKKKKMAP(SEQ ID NO: 64) of mouse c-abl IV; the sequences DRLRR(SEQ ID NO: 65) and PKQKKRK(SEQ ID NO: 66) of influenza virus NS1; the sequence RKLKKKIKKL(SEQ ID NO: 67) of a hepatitis delta virus antigen; the sequence REKKKFLKRR(SEQ ID NO: 68) of a mouse Mx1 protein; the sequence KRKGDEVDGVDEVAKKKSKK(SEQ ID NO: 69) of a human poly (ADP-ribose) polymerase; or the NLS sequence RKCLQAGMNLEARKTKK(SEQ ID NO: 70), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

Here, the split-type CRISPR enzyme may be a completely, incompletely or partially active enzyme or inactive enzyme.

For example, the SpCas9 may be divided into two parts between the residue 656, tyrosine, and the residue 657, threonine, thereby generating split SpCas9.

In addition, the split-type CRISPR enzyme may selectively include an additional domain, peptide, polypeptide or protein for reconstitution.

Here, the "reconstitution" refers to formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycine is present, thereby producing a reconstituted CRISPR enzyme.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

3. Target Sequence

The term "target sequence" is a base sequence present in a target gene or nucleic acid, and has complementarity to a guide sequence contained in a guide domain of a guide nucleic acid. The target sequence is a base sequence which may vary according to a target gene or nucleic acid, that is, a subject for gene manipulation or correction, which may be designed in various forms according to the target gene or nucleic acid.

The target sequence may form a complementary bond with the guide sequence contained in the guide domain of the guide nucleic acid, and a length of the target sequence may be the same as that of the guide sequence.

The target sequence may be a 5 to 50-base sequence.

In an embodiment, the target sequence may be a 16, 17, 18, 19, 20, 21, 22, 23, 24 or 25-base sequence.

The target sequence may be a nucleic acid sequence complementary to the guide sequence contained in the guide domain of the guide nucleic acid, which has, for example, at least 70%, 75%, 80%, 85%, 90% or 95% or more complementarity or complete complementarity.

In one example, the target sequence may be or include a 1 to 8-base sequence, which is not complementary to the guide sequence contained in the guide domain of the guide nucleic acid.

In addition, the target sequence may be a base sequence adjacent to a nucleic acid sequence that is able to be recognized by an editor protein.

In one example, the target sequence may be a continuous 5 to 50-base sequence adjacent to the 5' end and/or 3' end of the nucleic acid sequence that is able to be recognized by the editor protein.

In one exemplary embodiment, target sequences for a gRNA-CRISPR enzyme complex will be described below.

When the target gene or nucleic acid is targeted by the gRNA-CRISPR enzyme complex, the target sequence has complementarity to the guide sequence contained in the guide domain of gRNA. The target sequence is a base sequence which varies according to the target gene or nucleic acid, that is, a subject for gene manipulation or correction, which may be designed in various forms according to the target gene or nucleic acid.

In addition, the target sequence may be a base sequence adjacent to a PAM sequence which is able to be recognized by the CRISPR enzyme, that is, Cas9 or Cpf1.

In one example, the target sequence may be a continuous 5 to 50-base sequence adjacent to the 5' end and/or 3' end of the PAM sequence which is recognized by the CRISPR enzyme.

In one exemplary embodiment, when the CRISPR enzyme is SpCas9, the target sequence may be a continuous 16 to 25-base sequence adjacent to the 5' end and/or 3' end of a 5'-NGG-3', 5'-NAG-3' and/or 5'-NGA-3' (N=A, T, G or C; or A, U, G or C) sequence.

In another exemplary embodiment, when the CRISPR enzyme is StCas9, the target sequence may be a continuous 16 to 25-base sequence adjacent to the 5' end and/or 3' end of a 5'-NGGNG-3' and/or 5'-NNAGAAW-3' (W=A or T, and N=A, T, G or C; or A, U, G or C) sequence.

In still another exemplary embodiment, when the CRISPR enzyme is NmCas9, the target sequence may be a continuous 16 to 25-base sequence adjacent to the 5' end and/or 3' end of a 5'-NNNNGATT-3' and/or 5'-NNNGCTT-3' (N=A, T, G or C; or A, U, G or C) sequence.

In one exemplary embodiment, when the CRISPR enzyme is CjCas9, the target sequence may be a continuous 16 to 25-base sequence adjacent to the 5' end and/or 3' end of a 5'-NNNVRYAC-3' (V=G, C or A; R=A or G, Y=C or T, N=A, T, G or C; or A, U, G or C) sequence.

In another exemplary embodiment, when the CRISPR enzyme is SmCas9, the target sequence may be a continuous 16 to 25-base sequence adjacent to the 5' end and/or 3' end of a 5'-NGG-3' and/or 5'-NAAR-3'(R=A or G, N=A, T, G or C; or A, U, G or C) sequence.

In yet another exemplary embodiment, when the CRISPR enzyme is SaCas9, the target sequence may be a continuous 16 to 25-base sequence adjacent to the 5' end and/or 3' end of a 5'-NNGRR-3', 5'-NNGRRT-3' and/or 5'-NNGRRV-3' (R=A or G, V=G, C or A, N=A, T, G or C; or A, U, G or C) sequence.

In one exemplary embodiment, when the CRISPR enzyme is Cpf1, the target sequence may be a continuous 16 to 25-base sequence adjacent to the 5' end and/or 3' end of a 5'-TTN-3' (N=A, T, G or C; or A, U, G or C) sequence.

In one exemplary embodiment of the present invention, the target sequence may be a nucleic acid sequence contained in one or more genes selected from the group consisting of an FAD2 gene, an FAD3 gene, an FAD6 gene, an FAD7 gene, and an FAD8 gene.

The target sequence may be a nucleic acid sequence contained in the FAD2 gene.

The target sequence may be a nucleic acid sequence contained in the FAD3 gene.

The target sequence may be a nucleic acid sequence contained in the FAD6 gene.

The target sequence may be a nucleic acid sequence contained in the FAD7 gene.

The target sequence may be a nucleic acid sequence contained in the FAD8 gene.

Alternatively, the target sequence may be a partial nucleic acid sequence of one or more genes selected from the group consisting of an FAD2 gene, an FAD3 gene, an FAD6 gene, an FAD7 gene, and an FAD8 gene.

The target sequence may be a partial nucleic acid sequence of the FAD2 gene.

The target sequence may be a partial nucleic acid sequence of the FAD3 gene.

The target sequence may be a partial nucleic acid sequence of the FAD6 gene.

The target sequence may be a partial nucleic acid sequence of the FAD7 gene.

The target sequence may be a partial nucleic acid sequence of the FAD8 gene.

Alternatively, the target sequence may be a nucleic acid sequence of the coding or non-coding region or a mixture thereof of one or more genes selected from the group consisting of an FAD2 gene, an FAD3 gene, an FAD6 gene, an FAD7 gene, and an FAD8 gene.

The target sequence may be a nucleic acid sequence of the coding or non-coding region or a mixture thereof of the FAD2 gene.

The target sequence may be a nucleic acid sequence of the coding or non-coding region or a mixture thereof of the FAD3 gene.

The target sequence may be a nucleic acid sequence of the coding or non-coding region or a mixture thereof of the FAD6 gene.

The target sequence may be a nucleic acid sequence of the coding or non-coding region or a mixture thereof of the FAD7 gene.

The target sequence may be a nucleic acid sequence of the coding or non-coding region or a mixture thereof of the FAD8 gene.

Alternatively, the target sequence may be a nucleic acid sequence of the promoter, enhancer, 3'UTR or polyadenyl (polyA) region or a mixture thereof of one or more genes selected from the group consisting of an FAD2 gene, an FAD3 gene, an FAD6 gene, an FAD7 gene, and an FAD8 gene.

The target sequence may be a nucleic acid sequence of the promoter, enhancer, 3'UTR or polyadenyl (polyA) region or a mixture thereof of the FAD2 gene.

The target sequence may be a nucleic acid sequence of the promoter, enhancer, 3'UTR or polyadenyl (polyA) region or a mixture thereof of the FAD3 gene.

The target sequence may be a nucleic acid sequence of the promoter, enhancer, 3'UTR or polyadenyl (polyA) region or a mixture thereof of the FAD6 gene.

The target sequence may be a nucleic acid sequence of the promoter, enhancer, 3'UTR or polyadenyl (polyA) region or a mixture thereof of the FAD7 gene.

The target sequence may be a nucleic acid sequence of the promoter, enhancer, 3'UTR or polyadenyl (polyA) region or a mixture thereof of the FAD8 gene.

Alternatively, the target sequence may be a nucleic acid sequence of an exon, an intron or a mixture thereof of one or more genes selected from the group consisting of an FAD2 gene, an FAD3 gene, an FAD6 gene, an FAD7 gene, and an FAD8 gene.

The target sequence may be a nucleic acid sequence of an exon, an intron or a mixture thereof of the FAD2 gene.

The target sequence may be a nucleic acid sequence of an exon, an intron or a mixture thereof of the FAD3 gene.

The target sequence may be a nucleic acid sequence of an exon, an intron or a mixture thereof of the FAD6 gene.

The target sequence may be a nucleic acid sequence of an exon, an intron or a mixture thereof of the FAD7 gene.

The target sequence may be a nucleic acid sequence of an exon, an intron or a mixture thereof of the FAD8 gene.

Alternatively, The target sequence may be a nucleic acid sequence including or adjacent to a mutated region (e.g., a region different from a wild-type gene) of one or more genes selected from the group consisting of an FAD2 gene, an FAD3 gene, an FAD6 gene, an FAD7 gene, and an FAD8 gene.

The target sequence may be a nucleic acid sequence including or adjacent to a mutated region of the FAD2 gene.

The target sequence may be a nucleic acid sequence including or adjacent to a mutated region of the FAD3 gene.

The target sequence may be a nucleic acid sequence including or adjacent to a mutated region of the FAD6 gene.

The target sequence may be a nucleic acid sequence including or adjacent to a mutated region of the FAD7 gene.

The target sequence may be a nucleic acid sequence including or adjacent to a mutated region of the FAD8 gene.

Alternatively, the target sequence may be a continuous 5 to 50-nucleic acid sequence of one or more genes selected from the group consisting of an FAD2 gene, an FAD3 gene, an FAD6 gene, an FAD7 gene, and an FAD8 gene.

The target sequence may be a continuous 5 to 50-nucleic acid sequence of the FAD2 gene.

The target sequence may be a continuous 5 to 50-nucleic acid sequence of the FAD3 gene.

The target sequence may be a continuous 5 to 50-nucleic acid sequence of the FAD6 gene.

The target sequence may be a continuous 5 to 50-nucleic acid sequence of the FAD7 gene.

The target sequence may be a continuous 5 to 50-nucleic acid sequence of the FAD8 gene.

As one exemplary embodiment of the present invention, the above target sequences of the FAD2 gene are summarized in Table 1.

Unsaturated Fatty Acid Biosynthesis-Associated Factor-Manipulated Product

4. Guide Nucleic Acid-Editor Protein Complex and Use Thereof

A guide nucleic acid-editor protein complex may modify a target.

For example, the guide nucleic acid-editor protein complex may be used to ultimately regulate (e.g., inhibit, suppress, reduce, increase or promote) the expression of a protein of interest, remove a protein, regulate (e.g., inhibit, suppress, reduce, increase or promote) protein activity, or express a new protein.

Here, the guide nucleic acid-editor protein complex may act at a DNA, RNA, gene or chromosomal level.

For example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of the target DNA.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of target RNA.

In one example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target gene.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target chromosome.

The guide nucleic acid-editor protein complex may act at gene transcription and translation stages.

In one example, the guide nucleic acid-editor protein complex may promote or suppress the transcription of a target gene, thereby regulating (e.g., inhibiting, suppressing, reducing, increasing or promoting) the expression of a protein encoded by the target gene.

In another example, the guide nucleic acid-editor protein complex may promote or suppress the translation of a target gene, thereby regulating (e.g., inhibiting, suppressing, reducing, increasing or promoting) the expression of a protein encoded by the target gene.

The guide nucleic acid-editor protein complex may act at a protein level.

In one example, the guide nucleic acid-editor protein complex may manipulate or modify a target protein, thereby removing the target protein or regulating (e.g., inhibiting, suppressing, reducing, increasing or promoting) protein activity.

In one exemplary embodiment, the present invention provides a guide nucleic acid-editor protein complex used to manipulate a unsaturated fatty acid biosynthesis-associated factor, for example, an FAD gene, preferably an FAD2 gene, an FAD3 gene, an FAD6 gene, an FAD7 gene, and/or an FAD8 gene. Preferably, a gRNA-CRISPR enzyme complex is provided.

Particularly, the present invention may provide gRNA including a guide domain capable of forming a complementary bond with a target sequence from a gene, for example, isolated or non-natural gRNA and DNA encoding the same. The gRNA and the DNA sequence encoding the same may be designed to be able to complementarily bind to a target sequence listed in Table 1.

In addition, a target region of the gRNA is designed to provide a third gene, which has a nucleic acid modification, for example, double or single strand breaks; or a specific function at a target site in an FAD2 gene, an FAD3 gene, an FAD6 gene, an FAD7 gene, and/or an FAD8 gene.

In addition, when two or more gRNAs are used to induce two or more cleaving events in a target gene, for example, a double or single strand break, the two or more cleaving events may occur due to the same or different Cas9 proteins.

The gRNA may target, for example, two or more of the FAD2 gene, the FAD3 gene, the FAD6 gene, the FAD7 gene, and/or the FAD8 gene, or
  two or more regions in each of the FAD2 gene, the FAD3 gene, the FAD6 gene, the FAD7 gene, and/or the FAD8 gene, and
may independently induce the cleavage of a double strand and/or a single strand of the FAD2 gene, the FAD3 gene, the FAD6 gene, the FAD7 gene, and/or the FAD8 gene, or
  may induce the insertion of one foreign nucleotide into a cleavage site of the FAD2 gene, the FAD3 gene, the FAD6 gene, the FAD7 gene, and/or the FAD8 gene.

In addition, in another exemplary embodiment of the present invention, a nucleic acid constituting the guide nucleic acid-editor protein complex may include:
  (a) a sequence encoding a guide nucleic acid including a guide domain, which is complementary to a target sequence of the FAD2 gene as described herein; and
  (b) a sequence encoding an editor protein.

Here, there may be two or more of the (a) according to a target region, and the (b) may employ the same or two or more editor proteins.

In an embodiment, the nucleic acid may be designed to target an enzymatically inactive editor protein or a fusion protein (e.g., a transcription repressor domain fusion) thereof to place it sufficiently adjacent to a knockdown target site in order to reduce, decrease or inhibit expression of the FAD2 gene.

Besides, it should be obvious that the above-described structure, function, and all applications of the guide nucleic acid-editor protein complex will be utilized in manipulation of the FAD2 gene, the FAD3 gene, the FAD6 gene, the FAD7 gene, and/or the FAD8 gene.

Use of Guide Nucleic Acid-Editor Protein Complex

In an embodiment for the use of the guide nucleic acid-editor protein complex of the present invention, the manipulation or modification of target DNA, RNA, genes or chromosomes using the gRNA-CRISPR enzyme complex will be described below.

Gene Manipulation

A target gene or nucleic acid may be manipulated or corrected using the above-described gRNA-CRISPR enzyme complex, that is, the CRISPR complex. Here, the manipulation or correction of the target gene or nucleic acid includes all of the stages of i) cleaving or damaging the target gene or nucleic acid and ii) repairing the damaged target gene or nucleic acid.

i) Cleavage or Damage of Target Gene or Nucleic Acid
  i) The cleavage or damage of the target gene or nucleic acid may be cleavage or damage of the target gene or nucleic acid using the CRISPR complex, and particularly, cleavage or damage of a target sequence in the target gene or nucleic acid.

In one example, the cleavage or damage of the target gene or nucleic acid using the CRISPR complex may be complete cleavage or damage to the double strand of a target sequence.

In one exemplary embodiment, when wild-type SpCas9 is used, the double strand of a target sequence forming a complementary bond with gRNA may be completely cleaved.

In another exemplary embodiment, when SpCas9 nickase (D10A) and SpCas9 nickase (H840A) are used, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In still another exemplary embodiment, when SpCas9 nickase (D10A) and SpCas9 nickase (H840A), and two gRNAs having different target sequences are used, a complementary single strand of a target sequence forming a complementary bond with the first gRNA may be cleaved by the SpCas9 nickase (D10A), a non-complementary single strand of a target sequence forming a complementary bond with the second gRNS may be cleaved by the SpCas9 nickase (H840A), and the cleavages may take place sequentially or simultaneously.

In another example, the cleavage or damage of a target gene or nucleic acid using the CRISPR complex may be cleavage or damage to only the single strand of a target sequence. Here, the single strand may be a complementary single strand of a target sequence forming a complementary bond with gRNA, or a non-complementary single strand of the target sequence forming a complementary bond with gRNA.

In one exemplary embodiment, when SpCas9 nickase (D10A) is used, a complementary single strand of a target sequence forming a complementary bond with gRNA may be cleaved by the SpCas9 nickase (D10A), but a non-complementary single strand of the target sequence forming a complementary bond with gRNA may not be cleaved.

In another exemplary embodiment, when SpCas9 nickase (H840A) is used, a complementary single strand of a target sequence forming a complementary bond with gRNA may be cleaved by the SpCas9 nickase (H840A), but a non-complementary single strand of the target sequence forming a complementary bond with gRNA may not be cleaved.

In yet another example, the cleavage or damage of a target gene or nucleic acid using the CRISPR complex may be partial removal of a nucleic acid fragment.

In one exemplary embodiment, when two gRNAs having different target sequences and wild-type SpCas9 are used, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

In another exemplary embodiment, when two gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand nay be cleaved by the SpCas9 nickase (H840A), resulting in the removal of nucleic acid fragments by the first and second gRNAs, the wild-type SpCas9, the SpCas9 nickase (D10A) and the SpCas9 nickase (H840A).

In still another exemplary embodiment, when two gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand may be cleaved by the SpCas9 nickase (H840A), a complementary double strand of a target sequence forming a complementary bond with the second gRNA may be cleaved by the SpCas9 nickase (D10A), and a non-complementary single strand may be cleaved by the SpCas9 nickase (H840A), resulting in the removal of nucleic acid fragments by the first and second gRNAs, the SpCas9 nickase (D10A) and the SpCas9 nickase (H840A).

In yet another exemplary embodiment, when three gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand of a target sequence forming a complementary bond with the third gRNA may be cleaved by the SpCas9 nickase (H840A), resulting in the removal of nucleic acid fragments by the first gRNA, the second gRNA, the third gRNA, the wild-type SpCas9, the SpCas9 nickase (D10A) and the SpCas9 nickase (H840A).

In yet another exemplary embodiment, when four gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), a complementary single strand of a target sequence forming a complementary bond with the third gRNA may be cleaved by the SpCas9 nickase (D10A), and a non-complementary single strand of a target sequence forming a complementary bond with fourth gRNA may be cleaved by the SpCas9 nickase (H840A), resulting in the removal of nucleic acid fragments by the first gRNA, the second gRNA, the third gRNA, the fourth gRNA, the SpCas9 nickase (D10A) and the SpCas9 nickase (H840A).

ii) Repair or Restoration of Damaged Target Gene or Nucleic Acid

The target gene or nucleic acid cleaved or damaged by the CRISPR complex may be repaired or restored through non-homologous end joining (NHEJ) and homology-directed repairing (HDR).

Non-Homologous End Joining (NHEJ)

NHEJ is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutation in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a gene targeted by the CRISPR complex may be performed using such NHEJ. A double strand or two single strands of a target gene or nucleic acid may be cleaved using the CRISPR enzyme such as Cas9 or Cpf1, and the broken double strand or two single strands of the target gene or nucleic acid may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

Homology Directed Repairing (HDR)

HDR is a correction method without an error, which uses a homologous sequence as a template to repair or restoration a damaged gene or nucleic acid, and generally, to repair or restoration broken DNA, that is, to restore innate information of cells, the broken DNA is repaired using information of a complementary base sequence which is not modified or information of a sister chromatid. The most common type of HDR is homologous recombination (HR). HDR is a repair or restoration method usually occurring in the S or G2/M phase of actively dividing cells.

To repair or restore damaged DNA using HDR, rather than using a complementary base sequence or sister chromatin of the cells, a DNA template artificially synthesized using information of a complementary base sequence or homologous base sequence, that is, a nucleic acid template including a complementary base sequence or homologous base sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the target gene or nucleic acid modified by a mutation to a normal gene or nucleic acid, or a gene or nucleic acid to be expressed in cells, but the present invention is not limited thereto.

In one example, a double or single strand of a target gene or nucleic acid may be cleaved using the CRISPR complex, a nucleic acid template including a base sequence complementary to a base sequence adjacent to the cleavage site may be provided to cells, and the cleaved base sequence of the target gene or nucleic acid may be repaired or restored through HDR.

Here, the nucleic acid template including the complementary base sequence may have broken DNA, that is, a cleaved double or single strand of a complementary base sequence, and further include a nucleic acid sequence or nucleic acid fragment to be inserted into the broken DNA. An additional nucleic acid sequence or nucleic acid fragment may be inserted into a cleaved site of the broken DNA, that is, the target gene or nucleic acid using the nucleic acid template including a nucleic acid sequence or nucleic acid fragment to be inserted into the complementary base sequence. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The complementary base sequence may be a base sequence having complementary bonds with broken DNA, that is, right and left base sequences of the cleaved double or single strand of the target gene or nucleic acid. Alternatively, the complementary base sequence may be a base sequence having complementary bonds with broken DNA, that is, 3' and 5' ends of the cleaved double or single strand of the target gene or nucleic acid. The complementary base sequence may be a 15 to 3000-base sequence, a length or size of the complementary base sequence may be suitably designed according to a size of the nucleic acid template or the target gene. Here, as the nucleic acid template, a double- or single-stranded nucleic acid may be used, or it may be linear or circular, but the present invention is not limited thereto.

In another example, a double- or single-stranded target gene or nucleic acid is cleaved using the CRISPR complex, a nucleic acid template including a homologous base sequence with a base sequence adjacent to a cleavage site is provided to cells, and the cleaved base sequence of the target gene or nucleic acid may be repaired or restored by HDR.

Here, the nucleic acid template including the homologous base sequence may be broken DNA, that is, a cleaved double- or single-stranded homologous base sequence, and further include a nucleic acid sequence or nucleic acid fragment to be inserted into the broken DNA. An additional nucleic acid sequence or nucleic acid fragment may be inserted into broken DNA, that is, a cleaved site of a target gene or nucleic acid using the nucleic acid template including a homologous base sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The homologous base sequence may be broken DNA, that is, a base sequence having homology with cleaved double-stranded base sequence or right and left single-stranded base sequences of a target gene or nucleic acid. Alternatively, the complementary base sequence may be a base sequence having homology with broken DNA, that is, the 3' and 5' ends of a cleaved double or single strand of a target gene or nucleic acid. The homologous base sequence may be a 15 to 3000-base sequence, and a length or size of the homologous base sequence may be suitably designed according to a size of the nucleic acid template or a target gene or nucleic acid. Here, as the nucleic acid template, a double- or single-stranded nucleic acid may be used and may be linear or circular, but the present invention is not limited thereto.

Other than the NHEJ and HDR, there are methods of repairing or restoring broken DNA.

Single-Strand Annealing (SSA)

SSA is a method of repairing double strand breaks between two repeat sequences present in a target nucleic acid, and generally uses a repeat sequence of more than 30 bases. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

SSA, similar to HDR, utilizes a complementary sequence, that is, a complementary repeat sequence, and in contrast, does not requires a nucleic acid template for modifying or correcting a target nucleic acid sequence.

Single-Strand Break Repair (SSBA)

Single strand breaks in a genome are repaired through a separate mechanism, SSBR, from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single base. After DNA gap filling, a DNA ligase promotes end joining.

Mismatch Repair (MMR)

MMR works on mismatched DNA bases. Each of an MSH2/6 or MSH2/3 complex has ATPase activity and thus plays an important role in recognizing a mismatch and initiating a repair, and the MSH2/6 primarily recognizes base-base mismatches and identifies one or two base mismatches, but the MSH2/3 primarily recognizes a larger mismatch.

Base Excision Repair (BER)

BER is a repair method which is active throughout the entire cell cycle, and used to remove a small non-helix-distorting base damaged region from the genome. In the damaged DNA, damaged bases are removed by cleaving an N-glycoside bond joining a base to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary base, and then an end of the newly-filled complementary base is ligated with the backbone by a DNA ligase, resulting in repair of the damaged DNA.

Nucleotide Excision Repair (NER)

NER is an excision mechanism important for removing large helix-distorting damage from DNA, and when the damage is recognized, a short single-strand DNA segment containing the damaged region is removed, resulting in a single strand gap of 22 to 30 bases. The generated gap is filled with a new complementary base, and an end of the newly filled complementary base is ligated with the backbone by a DNA ligase, resulting in the repair of the damaged DNA.

Gene Manipulation Effects

Manipulation or correction of a target gene or nucleic acid may largely lead to effects of knockout, knockdown, and knockin.

Knockout

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or nucleic acid is edited or corrected using a gRNA-CRISPR enzyme complex, that is, a CRISPR complex, the target gene or nucleic acid may be cleaved using the CRISPR complex. The damaged target gene or nucleic acid may be repaired through NHEJ using the CRISPR complex. The damaged target gene or nucleic acid may have indels due to NHEJ, and thereby, specific knockout for the target gene or nucleic acid may be induced.

Knockdown

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when a target gene or nucleic acid is edited or corrected using a gRNA-CRISPR inactive enzyme-transcription inhibitory activity domain complex, that is, a CRISPR inactive complex including a transcription inhibitory activity domain, the CRISPR inactive complex may specifically bind to the target gene or nucleic acid, transcription of the target gene or nucleic acid may be inhibited by the transcription inhibitory activity domain included in the CRISPR inactive complex, thereby inducing knockdown in which expression of the corresponding gene or nucleic acid is inhibited.

Knockin

The term "knockin" refers to insertion of a specific nucleic acid or gene into a target gene or nucleic acid, and here, the "specific nucleic acid" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited or corrected using a gRNA-CRISPR enzyme complex, that is, a CRISPR complex, the target gene or nucleic acid may be cleaved using the CRISPR complex. The target gene or nucleic acid damaged using the CRISPR complex may be repaired through HDR. Here, a specific nucleic acid may be inserted into the damaged gene or nucleic acid using a donor.

The term "donor" refers to a nucleic acid sequence that helps HDR-based repair of the damaged gene or nucleic acid, and here, the donor may include a specific nucleic acid.

The donor may be a double- or single-stranded nucleic acid.

The donor may be present in a linear or circular shape.

The donor may include a nucleic acid sequence having homology with a target gene or nucleic acid.

For example, the donor may include a nucleic acid sequence having homology with each of base sequences at a location into which a specific nucleic acid is to be inserted, for example, upstream (left) and downstream (right) of a damaged nucleic acid. Here, the specific nucleic acid to be inserted may be located between a nucleic acid sequence having homology with a base sequence downstream of the damaged nucleic acid and a nucleic acid sequence having homology with a base sequence upstream of the damaged nucleic acid. Here, the homologous nucleic acid sequence may have at least 50%, 55%, 60%, 65%, 70%, 75%, 80%, 85%, 90% or 95% or more homology or complete homology.

The donor may optionally include an additional nucleic acid sequence. Here, the additional nucleic acid sequence may serve to increase donor stability, knockin efficiency or HDR efficiency.

For example, the additional nucleic acid sequence may be an A, T-rich nucleic acid sequence, that is, an A-T rich domain. In addition, the additional nucleic acid sequence may be a scaffold/matrix attachment region (SMAR).

In one exemplary embodiment relating to a gene manipulation effect of the present invention, a manipulated target gene obtained using a gRNA-CRISPR enzyme complex, that is, a manipulated unsaturated fatty acid biosynthesis-associated factor may have the following constitution.

In one exemplary embodiment, when the unsaturated fatty acid biosynthesis-associated factor is a gene,
the constitution of the artificially manipulated unsaturated fatty acid biosynthesis-associated factor by the gRNA-CRISPR enzyme complex may include modification of one or more nucleic acids among
a deletion or insertion of one or more nucleotides;
a substitution with one or more nucleotides different from a wild-type gene; and
an insertion of one or more foreign nucleotides
in a continuous 1 bp to 50 bp, 1 bp to 40 bp or 1 bp to 30 bp, preferably, 3 bp to 25 bp region in the base sequence, which is located in a PAM sequence in a nucleic acid sequence constituting the unsaturated fatty acid biosynthesis-associated factor or adjacent to a 5' end and/or 3' end thereof.

In addition, a chemical modification of one or more nucleotides may be included in the nucleic acid sequence constituting the unsaturated fatty acid biosynthesis-associated factor.

Here, the "foreign nucleotide" is the concept including all exogeneous, for example, heterologous or artificially-synthesized nucleotides, other than nucleotides innately included in the unsaturated fatty acid biosynthesis-associated factor. The foreign nucleotide also includes a nucleotide with a size of several hundred, thousand or tens of thousands of bp to express a protein having a specific function, as well as a small oligonucleotide with a size of 50 bp or less. Such a foreign nucleotide may be a donor.

The chemical modification may include methylation, acetylation, phosphorylation, ubiquitination, ADP-ribosylation, myristylation, and glycosylation, for example, substitution of some functional groups contained in a nucleotide with any one of a hydrogen atom, a fluorine atom, an —O-alkyl group, an —O-acyl group, and an amino group, but the present invention is not limited thereto. In addition, to increase transferability of a nucleic acid molecule, the functional groups may also be substituted with any one of —Br, —Cl, —R, —R'OR, —SH, —SR, —N3 and —CN (R=alkyl, aryl, alkylene). In addition, the phosphate backbone of at least one nucleotide may be substituted with any one of an alkylphosphonate form, a phosphoroamidate form and a boranophosphate form. In addition, the chemical modification may be a substitution of at least one type of nucleotide contained in the nucleic acid molecule with any one of a locked nucleic acid (LNA), an unlocked nucleic acid (UNA), a morpholino, and a peptide nucleic acid (PNA), and the chemical modification may be bonding of the nucleic acid molecule with one or more selected from the group consisting of a lipid, a cell-penetrating peptide and a cell-target ligand.

To form a desired unsaturated fatty acid biosynthesis controlling system, artificial modification using a gRNA-CRISPR enzyme complex may be applied to the nucleic acid constituting the unsaturated fatty acid biosynthesis-associated factor.

A region including the nucleic acid modification of the unsaturated fatty acid biosynthesis-associated factor may be a target region or target sequence.

Such a target sequence may be a target for the gRNA-CRISPR enzyme complex, and the target sequence may include or not include a PAM sequence recognized by the CRISPR enzyme. Such a target sequence may provide a critical standard in a gRNA designing stage to those of ordinary skill in the art.

Such nucleic acid modification includes the "cleavage" of a nucleic acid.

The term "cleavage" in a target region refers to breakage of a covalent backbone of polynucleotides. The cleavage includes enzymatic or chemical hydrolysis of a phosphodiester bond, but the present invention is not limited thereto, and also include various other methods. The cleavage is able to be performed on both of a single strand and a double strand, and the cleavage of a double strand may result from distinct single-strand cleavage. The double-strand cleavage may generate blunt ends or staggered ends.

When an inactivated CRISPR enzyme is used, it may induce a factor possessing a specific function to approach a certain region of the target region or unsaturated fatty acid biosynthesis-associated factor without the cleavage process. Chemical modification of one or more nucleotides in the nucleic acid sequence of the unsaturated fatty acid biosynthesis-associated factor may be included according to such a specific function.

In one example, various indels may occur due to target and non-target activities through the nucleic acid cleavage formed by the gRNA-CRISPR enzyme complex.

The term "indel" is the generic term for an insertion or deletion mutation occurring in-between some bases in a DNA base sequence. The indel may be introduced into a target sequence during repair by an HDR or NHEJ mechanism when the gRNA-CRISPR enzyme complex cleaves the nucleic acid (DNA or RNA) of the unsaturated fatty acid biosynthesis-associated factor as described above.

The artificially manipulated unsaturated fatty acid biosynthesis-associated factor of the present invention refers to modification of the nucleic acid sequence of an original gene by cleavage, indels, or insertion using a donor of such a nucleic acid, and contributes to a desired system for controlling unsaturated fatty acids biosynthesis, for example, exhibition of an effect of promoting or suppressing a specific unsaturated fatty acid.

For example, a specific protein may be expressed and its activity may be stimulated by the artificially manipulated unsaturated fatty acid biosynthesis-associated factor.

A specific protein may be inactivated by the artificially manipulated unsaturated fatty acid biosynthesis-associated factor.

In one example, a specific target region of each unsaturated fatty acid biosynthesis-associated factor of the genome, for example, reverse regulatory genes such as an FAD2 gene, an FAD3 gene, an FAD6 gene, an FAD7 gene, and/or an FAD8 gene may be cleaved, resulting in knockdown or knockout of the gene.

In another example, targeted knockdown may be mediated using an enzymatically inactive CRISPR enzyme fused to a transcription repressor domain or chromatin-modified protein to change transcription, for example, to block, negatively regulate or decrease the transcription of an FAD2 gene, an FAD3 gene, an FAD6 gene, an FAD7 gene, and/or an FAD8 gene.

A production of unsaturated fatty acids may be regulated by the artificially manipulated unsaturated fatty acid biosynthesis-associated factor.

A plant body increased or decreased in the content of a specific unsaturated fatty acid or a processed product using the plant body may be produced by the artificially manipulated unsaturated fatty acid biosynthesis-associated factor.

In one exemplary embodiment of the present invention, the artificially manipulated unsaturated fatty acid biosynthesis-associated factor may provide various artificially manipulated unsaturated fatty acid biosynthesis-associated factors according to the constitutional characteristic of the gRNA-CRISPR enzyme complex (e.g., included in a target region of the unsaturated fatty acid biosynthesis-associated factor or different in the adjacent major PAM sequence).

Hereinafter, while representative examples of CRISPR enzymes and an unsaturated fatty acid biosynthesis-associated gene have been illustrated, they are merely specific examples, and thus the present invention is not limited thereto.

For example, when the CRISPR enzyme is a SpCas9 protein, the PAM sequence is 5'-NGG-3' (N is A, T, G, or C), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NGG-3' sequence in a target gene.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a) deletion of one or more nucleotides of a continuous 1 bp to 25 bp, for example, 17 bp to 23 bp, region in the base sequence adjacent to the 5' end and/or 3' end of the 5'-NGG-3' (N is A, T, C or G) sequence, b) substitution of one or more nucleotides of a continuous 1 bp to 25 bp, for example, 17 bp to 23 bp, region in the base sequence adjacent to the 5' end and/or 3' end of the 5'-NGG-3' sequence with nucleotides different from those of the wild-type gene, c) insertion of one or more nucleotides into a continuous 1 bp to 25 bp, for example, 17 bp to 23 bp, region in the base sequence adjacent to the 5' end and/or 3' end of the 5'-NGG-3' sequence, or d) a combination of two or more selected from a) through c) in the nucleic acid sequence of the unsaturated fatty acid biosynthesis-associated factor.

For example, when the CRISPR enzyme is a CjCas9 protein, the PAM sequence is 5'-NNNNRYAC-3' (each N is independently A, T, C or G, R is A or G, and Y is C or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNRYAC-3' sequence in a target gene.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a') deletion of one or more nucleotides of a continuous 1 bp to 25 bp, for example, 17 bp to 23 bp, region in the base sequence adjacent to the 5' end and/or 3' end of the 5'-NNNNRYAC-3' (each N is independently A, T, C or G, R is A or G, and Y is C or T), b') substitution of one or more nucleotides of a continuous 1 bp to 25 bp, for example, 17 bp to 23 bp, region in the base sequence adjacent to the 5' end and/or 3' end of the 5'-NNNNRYAC-3' sequence with nucleotides different from those of the wild-type gene, c') insertion of one or more nucleotides into a continuous 1 bp to 25 bp, for example, 17 bp to 23 bp, region in the base sequence adjacent to the 5' end and/or 3' end of the 5'-NNNNRYAC-3' sequence, or d') a combination of two or more selected from a') through c') in the nucleic acid sequence of the unsaturated fatty acid biosynthesis-associated factor.

For example, when the CRISPR enzyme is a StCas9 protein, the PAM sequence is 5'-NNAGAAW-3' (each N is independently A, T, C or G, and W is A or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNAGAAW-3' sequence in a target gene.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a") deletion of one or more nucleotides of a continuous 1 bp to 25 bp, for example, 17 bp to 23 bp, region in the base sequence adjacent to the 5' end of the 5'-NNAGAAW-3' sequence (each N is independently A, T, C or G, and W is A or T), b") substitution of one or more nucleotides of a continuous 1 bp to 25 bp, for example, 17 bp to 23 bp, region in the base sequence adjacent to the 5' end and/or 3' end of the 5'-NNAGAAW-3' sequence with nucleotides different from those of the wild-type gene, c") insertion of one or more nucleotides into a continuous 1 bp to 25 bp, for example, 17 bp to 23 bp, region in the base sequence adjacent to the 5' end and/or 3' end of the 5'-NNAGAAW-3' sequence, or d") a combination of two or more selected from a") through c") in the nucleic acid sequence of the unsaturated fatty acid biosynthesis-associated factor.

For example, when the CRISPR enzyme is an NmCas9 protein, the PAM sequence is 5'-NNNNGATT-3'(each N is independently A, T, C or G), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNGATT-3' sequence in a target gene.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a'") deletion of one or more nucleotides of a continuous 1 bp to 25 bp, for example, 17 bp to 23 bp, region in the base sequence adjacent to the 5' end and/or the 3' end of the 5'-NNNNGATT-3' sequence (each N is independently A, T, C or G), b''') substitution of one or more nucleotides of a continuous 1 bp to 25 bp, for example, 17 bp to 23 bp, region in the base sequence adjacent to the 5' end and/or 3' end of the 5'-NNNNGATT-3' sequence with nucleotides different from those of the wild-type gene, c''') insertion of one or more nucleotides into a continuous 1 bp to 25 bp, for example, 17 bp to 23 bp, region in the base sequence adjacent to the 5'-NNNNGATT-3' sequence, or d''') a combination of two or more selected from a''') through c''') in the nucleic acid sequence of the unsaturated fatty acid biosynthesis-associated factor.

For example, when the CRISPR enzyme is an SaCas9 protein, the PAM sequence is 5'-NNGRR(T)-3' (each N is independently A, T, C or G, R is A or G, and (T) is a randomly addable sequence), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNGRR(T)-3' sequence in a target gene.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a'''') deletion of one or more nucleotides of a continuous 1 bp to 25 bp, for example, 17 bp to 23 bp region, in the base sequence adjacent to the 5' end and/or the 3' end of the 5'-NNGRR(T)-3' sequence (each N is independently A, T, C or G, R is A or G, and (T) is a randomly addable sequence), b'''') substitution of one or more nucleotides of a continuous 1 bp to 25 bp, for example, 17 bp to 23 bp, region in the base sequence adjacent to the 5' end and/or 3' end of the 5'-NNGRR(T)-3' sequence with nucleotides different from those of the wild-type gene, c'''') insertion of one or more nucleotides into a continuous 1 bp to 25 bp, for example, 17 bp to 23 bp, region in the base sequence adjacent to the 5'-NNGRR(T)-3' sequence, or d'''') a combination of two or more selected from a'''') through c'''') in the nucleic acid sequence of the unsaturated fatty acid biosynthesis-associated factor.

For example, when the CRISPR enzyme is a Cpf1 protein, the PAM sequence is 5'-TTN-3' (N is A, T, C or G), and the cleaved base sequence region (target region) may be a continuous 10 bp to 30 bp, for example, 15 bp to 26 bp, 17 bp to 30 bp or 17 bp to 26 bp, region in the base sequence adjacent to the 5' end or the 3' end of the 5'-TTN-3' sequence.

The Cpf1 protein may be derived from a microorganism such as Parcubacteria bacterium (GWC2011_GWC2_44_17), Lachnospiraceae bacterium (MC2017), Butyrivibrio proteoclasiicus, Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Smiihella sp. (SC_KO8D17), Leptospira inadai, Lachnospiraceae bacterium (MA2020), Francisella novicida (U112), candidatus Methanoplasma termitum, or Eubacterium eligens, for example, Parcubacteria bacterium (GWC2011_GWC2_44_17), Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Leptospira inadai, Lachnospiraceae bacterium (MA2020), Francisella novicida (U112), candidatus Methanoplasma termitum, or Eubacterium eligens, but the present invention is not limited thereto.

The present invention may provide an artificially manipulated unsaturated fatty acid biosynthesis-associated factor, for example, an artificially manipulated FAD2 gene, FAD3 gene, FAD6 gene, FAD7 gene, and/or FAD8 gene, which is prepared by a''''') deletion of one or more nucleotides of a continuous 10 bp to 30 bp, for example, 15 bp to 26 bp, region in the base sequence adjacent to the 5' end and/or the 3' end of the 5'-TTN-3' sequence (N is A, T, C or G), b''''') substitution of one or more nucleotides of a continuous 10 bp to 30 bp, for example, 15 bp to 26 bp, region in the base sequence adjacent to the 5' end and/or 3' end of the 5'-TTN-3' sequence with nucleotides different from those of the wild-type gene, c''''') insertion of one or more nucleotides of a continuous 10 bp to 30 bp, for example, 15 bp to 26 bp, region in the base sequence adjacent to the 5' end and/or 3' end of the 5'-TTN-3' sequence, or d''''') a combination of two or more selected from a''''') through c''''') in the nucleic acid sequence of the unsaturated fatty acid biosynthesis-associated factor.

In another exemplary embodiment, when the unsaturated fatty acid biosynthesis-associated factor is a protein, the artificially manipulated protein includes all proteins involved in formation of new or modified unsaturated fatty acid biosynthesis by a direct or indirect action of the gRNA-CRISPR enzyme complex.

For example, the artificially manipulated protein may be a protein expressed by an unsaturated fatty acid biosynthesis-associated factor (gene) artificially manipulated by the gRNA-CRISPR enzyme complex or another protein increased or reduced by an influence by such protein activity, but the present invention is not limited thereto.

The artificially manipulated unsaturated fatty acid biosynthesis-associated factor (protein) may have an amino acid composition and activity corresponding to the composition of the artificially manipulated unsaturated fatty acid biosynthesis-associated factor (gene).

As an embodiment, an (i) artificially manipulated protein which is changed in expression characteristics may be provided.

For example, protein modification may have one or more characteristics:

a decrease or increase in expression level according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the unsaturated fatty acid biosynthesis-associated factor or adjacent to the 5' end and/or the 3' end thereof;

a decrease or increase in expression level according to the substitution with one or more nucleotides different from those of a wild-type gene;

a decrease or increase in expression level, expression of a fusion protein or independent expression of a specific protein according to the insertion of one or more foreign nucleotides; and a decrease or increase in expression level of a third protein influenced by expression characteristics of the above-described proteins.

An (ii) artificially manipulated protein which is changed in structural characteristics may be provided.

For example, protein modification may have one or more characteristics:

a change in codons, amino acids and three-dimensional structure according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the unsaturated fatty acid biosynthesis-associated factor or adjacent to the 5' end and/or the 3' end thereof;

a change in codons, amino acids, and three-dimensional structure thereby according to the substitution with one or more nucleotides different from a wild-type gene;

a change in codons, amino acids, and three-dimensional structure, or a fusion structure with a specific protein or independent structure from which a specific protein is separated according to the insertion of one or more foreign nucleotides; and a change in codons, amino acids, and three-dimensional structure of a third protein influenced by the above-described protein changed in structural characteristic.

An (iii) artificially manipulated protein changed in functional characteristics may be provided.

For example, protein modification may have one or more characteristics:

the activation or inactivation of a specific function by protein modification caused by a deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the unsaturated fatty acid biosynthesis-associated factor or adjacent to the 5' end and/or the 3' end thereof;

the activation or inactivation of a specific function or introduction of a new function by protein modification caused by substitution with one or more nucleotides different from those of a wild-type gene;

the activation or inactivation of a specific function or introduction of a new function by protein modification caused by insertion of one or more foreign nucleotides, particularly, introduction of a third function to an existing function due to fusion or independent expression of a specific protein; and the change in the function of a third protein influenced by the above-described protein changed in functional characteristics.

In addition, a protein artificially manipulated by the chemical modification of one or more nucleotides in the nucleic acid sequence constituting the unsaturated fatty acid biosynthesis-associated factor may be included.

For example, one or more of the expression, structural and functional characteristics of a protein caused by methylation, acetylation, phosphorylation, ubiquitination, ADP-ribosylation, myristylation and glycosylation may be changed.

For example, the third structure and function may be achieved by binding of a third protein into the nucleic acid sequence of the gene due to the chemical modification of nucleotides.

5. Other Additional Components

An additional component may be selectively added to increase the efficiency of a guide nucleic acid-editor protein complex or improve the repair efficiency of a damaged gene or nucleic acid.

The additional component may be selectively used to improve the efficiency of the guide nucleic acid-editor protein complex.

Activator

The additional component may be used as an activator to increase the cleavage efficiency of a target nucleic acid, gene or chromosome of the guide nucleic acid-editor protein complex.

The term "activator" refers to a nucleic acid serving to stabilize the bonding between the guide nucleic acid-editor protein complex and the target nucleic acid, gene or chromosome, or to allow the guide nucleic acid-editor protein complex to more easily approach the target nucleic acid, gene or chromosome.

The activator may be a double-stranded nucleic acid or single-stranded nucleic acid.

The activator may be linear or circular.

The activator may be divided into a "helper" that stabilizes the bonding between the guide nucleic acid-editor protein complex and the target nucleic acid, gene or chromosome, and an "escorter" that serves to allow the guide nucleic acid-editor protein complex to more easily approach the target nucleic acid, gene or chromosome.

The helper may increase the cleavage efficiency of the guide nucleic acid-editor protein complex with respect to the target nucleic acid, gene or chromosome.

For example, the helper includes a nucleic acid sequence having homology with the target nucleic acid, gene or chromosome. Therefore, when the guide nucleic acid-editor protein complex is bonded to the target nucleic acid, gene or chromosome, the homologous nucleic acid sequence included in the helper may form an additional complementary bond with the target nucleic acid, gene or chromosome to stabilize the bonding between the guide nucleic acid-editor protein complex and the target nucleic acid, gene or chromosome.

The escorter may increase the cleavage efficiency of the guide nucleic acid-editor protein complex with respect to the target nucleic acid, gene or chromosome.

For example, the escorter includes a nucleic acid sequence having homology with the target nucleic acid, gene or chromosome. Here, the homologous nucleic acid sequence included in the escorter may partly form a complementary bond with a guide nucleic acid of the guide nucleic acid-editor protein complex. Therefore, the escorter partly forming a complementary bond with the guide nucleic acid-editor protein complex may partly form a complementary bond with the target nucleic acid, gene or chromosome, and as a result, may allow the guide nucleic acid-editor protein complex to accurately approach the position of the target nucleic acid, gene or chromosome.

The homologous nucleic acid sequence may have at least 50%, 55%, 60%, 65%, 70%, 75%, 80%, 85%, 90% or 95% or more homology, or complete homology.

In addition, the additional component may be selectively used to improve the repair efficiency of the damaged gene or nucleic acid.

Assistor

The additional component may be used as an assistor to improve the repair efficiency of the damaged gene or nucleic acid.

The term "assistor" refers to a nucleic acid that serves to participate in a repair process or increase the repair efficiency of the damaged gene or nucleic acid, for example, the gene or nucleic acid cleaved by the guide nucleic acid-editor protein complex.

The assistor may be a double-stranded nucleic acid or single-stranded nucleic acid.

The assistor may be present in a linear or circular shape.

The assistor may be divided into an "NHEJ assistor" that participates in a repair process using NHEJ or improves repair efficiency and an "HDR assistor" that participates in a repair process using HDR or improves repair efficiency according to a repair method.

The NHEJ assistor may participate in a repair process or improve the repair efficiency of the damaged gene or nucleic acid using NHEJ.

For example, the NHEJ assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and include a nucleic acid sequence having homology with the nucleic acid sequence at the other end (e.g., the 5' end) of the damaged nucleic acid sequence. In addition, a nucleic acid sequence having homology with each of the base sequences upstream and downstream of the damaged nucleic acid sequence may be included. The nucleic acid sequence having such homology may assist two parts of the damaged nucleic acid sequence to be placed in close proximity, thereby increasing the repair efficiency of the damaged nucleic acid by NHEJ.

The HDR assistor may participate in the repair process or improve repair efficiency of the damaged gene or nucleic acid using HDR.

For example, the HDR assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and a nucleic acid sequence having homology with the nucleic acid sequence at the other end (e.g., the 5' end) of the damaged nucleic acid sequence. Alternatively, a nucleic acid sequence having homology with each of the base sequences upstream and downstream of the damaged nucleic acid sequence may be included. The nucleic acid sequence having such homology may serve as a template of the damaged nucleic acid sequence to increase the repair efficiency of the damaged nucleic acid by HDR.

In another example, the HDR assistor may include a nucleic acid sequence having homology with a part of the damaged nucleic acid sequence and a specific nucleic acid, for example, a nucleic acid or gene to be inserted. Here, the homologous nucleic acid sequence may include a nucleic acid sequence having homology with each of the base sequences upstream and downstream of the damaged nucleic acid sequence. The specific nucleic acid may be located between a nucleic acid sequence having homology with a base sequence downstream of the damaged nucleic acid and a nucleic acid sequence having homology with a base sequence upstream of the damaged nucleic acid. The nucleic acid sequence having such homology and specific nucleic acid may serve as a donor to insert a specific nucleic acid into the damaged nucleic acid, thereby increasing HDR efficiency for knockin.

The homologous nucleic acid sequence may have at least 50%, 55%, 60%, 65%, 70%, 75%, 80%, 85%, 90% or 95% or more homology or complete homology.

6. Subject

The term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target nucleic acid, gene, chromosome or protein of the guide nucleic acid-editor protein complex.

The organism may be cells, tissue, or a plant.

The cells may be eukaryotic cells.

The eukaryotic cells may be plant cells.

The tissue may be tissue of a plant such as a leaf, stem, root, flower, fruit or callus, and the like, etc.

The plant may be a plant in various periods from a seed to a mature body.

The plant may be a plant body including an unsaturated fatty acid.

In addition, the subject may be a specimen or sample including a target nucleic acid, gene, chromosome or protein of the guide nucleic acid-editor protein complex.

The specimen or sample may be obtained from a plant body.

In the present invention, as a specific example, the subject may include a target gene or nucleic acid of the guide nucleic acid-editor protein complex.

Here, the target gene may be an unsaturated fatty acid biosynthesis-associated factor, for example, an FAD2 gene, an FAD3 gene, an FAD6 gene, an FAD7 gene, and/or an FAD8 gene.

The target gene may be a wild type, or a modified form in the wild-type.

In one exemplary embodiment of the present invention, the subject may include a gene or nucleic acid manipulated by the guide nucleic acid-editor protein complex.

Here, the manipulated gene may be an unsaturated fatty acid biosynthesis-associated factor, for example, an FAD2 gene, an FAD3 gene, an FAD6 gene, an FAD7 gene, and/or an FAD8 gene.

Here, the guide nucleic acid may target an unsaturated fatty acid biosynthesis-associated factor, for example, an FAD2 gene, an FAD3 gene, an FAD6 gene, an FAD7 gene, and/or an FAD8 gene.

The guide nucleic acid may be a nucleic acid sequence complementary to a target sequence of the FAD2 gene, FAD3 gene, FAD6 gene, FAD7 gene, and/or FAD8 gene.

The guide nucleic acid may target one or more genes.

The guide nucleic acid may simultaneously target two or more genes. Here, the two or more genes may be homologous or heterologous genes.

The guide nucleic acid may target one or more target sequences.

The guide nucleic acid may be designed in various forms according to the number or locations of the target sequences.

In one exemplary embodiment of the present invention, the guide nucleic acid may be a nucleic acid sequence complementary to one or more target sequences of the sequences listed in Table 1.

In a certain embodiment, for artificial manipulation of the FAD2 gene, a guide nucleic acid sequence corresponding to any one of the target sequences of SEQ ID NOs: 1 to 30.

In a certain embodiment, for artificial manipulation of the FAD2 gene, an editor protein that interacts with a guide nucleic acid sequence corresponding to, for example, forming a complex with any one of the target sequences of SEQ ID NOs: 1 to 30, for example, SEQ ID NOs: 7 or 30, is provided.

In a certain embodiment, a nucleic acid modification product of each gene in which artificial manipulation occurs at a target sequence region of any one of SEQ ID NOs: 1 to 30, for example, SEQ ID NOs: 7 or 30, and an expression product thereof are provided.

7. Delivery

The guide nucleic acid, editor protein or guide nucleic acid-editor protein complex may be delivered or introduced into a subject by various delivering methods and various forms.

The guide nucleic acid may be delivered or introduced into a subject in the form of DNA, RNA or a mixed form.

The editor protein may be delivered or introduced into a subject in the form of DNA, RNA, a DNA/RNA mixture, a peptide, a polypeptide, which encodes the editor protein, or a protein.

The guide nucleic acid-editor protein complex may be delivered or introduced into a target in the form of DNA, RNA or a mixture thereof, which encodes each component, that is, a guide nucleic acid or an editor protein.

The guide nucleic acid-editor protein complex may be delivered or introduced into a subject as a complex of a guide nucleic acid having a form of DNA, RNA or a mixture thereof and an editor protein having a form of a peptide, polypeptide or protein.

In addition, an additional component capable of increasing or inhibiting the efficiency of the guide nucleic acid-editor protein complex may be delivered or introduced into a subject by various delivering methods and in various forms.

The additional component may be delivered or introduced into a subject in the form of DNA, RNA, a DNA/RNA mixture, a peptide, a polypeptide or a protein.

i) Delivery in Form of DNA, RNA or Mixture Thereof

The form of DNA, RNA or a mixture thereof, which encodes the guide nucleic acid and/or editor protein may be delivered or introduced into a subject by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

Vector-Based Introduction

The nucleic acid sequence encoding the guide nucleic acid and/or editor protein may be delivered or introduced into a subject by a vector.

The vector may include a nucleic acid sequence encoding a guide nucleic acid and/or editor protein.

For example, the vector may simultaneously include nucleic acid sequences, which encode the guide nucleic acid and the editor protein, respectively.

For example, the vector may include the nucleic acid sequence encoding the guide nucleic acid.

As an example, domains included in the guide nucleic acid may be contained all in one vector, or may be divided and then contained in different vectors.

For example, the vector may include the nucleic acid sequence encoding the editor protein.

In one example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

For example, a promoter useful for the guide nucleic acid and/or the editor protein may be a root specific expression promoter, a seed specific promoter, whole-body expression inducible promoter or a leaf or the others tissue specific promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a mosaic virus, a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant mosaic virus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

In addition, a vector may be included in a bacterium and introduced into a subject.

Here, the vector may be included in an *Agrobacterium* and introduced into a subject, but the present invention is not limited thereto.

Generally, a method of transferring a desired genetic material to a subject using agrobacteria is most widely used, and in the case of a plant, to genetically modify the plant, the DNA of the agrobacteria may be inserted into the chromosome of a plant body in a form of a nucleic acid protein called a plasmid. This may serve to transfer a genetic material into cells of the plant body, and the transferred genetic material is fused in the cells. The above-described method may be widely used to produce an *Agrobacterium* gene-modified crop, and other than this, it can also be used as a system for studying the reaction of cells for genetic transformation.

Non-Vector-Based Introduction

A nucleic acid sequence encoding a guide nucleic acid and/or editor protein may be delivered or introduced into a subject using a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, particle bombardment, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

As an example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nanovesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

Other additives may be included.

ii) Delivery in Form of Peptide, Polypeptide or Protein

An editor protein in the form of a peptide, polypeptide or protein may be delivered or introduced into a subject by a method known in the art.

The peptide, polypeptide or protein form may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

iii) Delivery in Form of Nucleic Acid-Protein Mixture

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

In the present invention, as an embodiment of a method for delivering the guide nucleic acid and/or editor protein into a subject, the delivery of gRNA, a CRISPR enzyme or a gRNA-CRISPR enzyme complex will be described below.

In an embodiment of the present invention, a nucleic acid sequence encoding the gRNA and/or CRISPR enzyme will be delivered or introduced into a subject using a vector.

The vector may include the nucleic acid sequence encoding the gRNA and/or CRISPR enzyme.

For example, the vector may simultaneously include the nucleic acid sequences encoding the gRNA and the CRISPR enzyme.

For example, the vector may include the nucleic acid sequence encoding the gRNA.

In one example, domains contained in the gRNA may be contained in one vector, or may be divided and then contained in different vectors.

For example, the vector may include the nucleic acid sequence encoding the CRISPR enzyme.

In one example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

For example, a promoter useful for the guide nucleic acid and/or the editor protein may be a root specific expression promoter, a seed specific promoter, whole-body expression inducible promoter or a leaf or the others tissue specific promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a mosaic virus, a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The gRNA and/or CRISPR enzyme may be introduced into a subject using a virus having such a characteristic. The gRNA and/or CRISPR enzyme introduced using the virus may be temporarily expressed in the subject (e.g., cells). Alternatively, the gRNA and/or CRISPR enzyme introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector only including gRNA or a CRISPR enzyme or a viral vector including both of gRNA and a CRISPR enzyme may be designed. Alternatively, a viral vector including gRNA, a CRISPR enzyme and additional components may be designed.

In one example, a nucleic acid sequence encoding gRNA and/or a CRISPR enzyme may be delivered or introduced by a recombinant mosaic virus.

In another example, a nucleic acid sequence encoding gRNA and/or a CRISPR enzyme may be delivered or introduced by a recombinant adenovirus.

In still another example, a nucleic acid sequence encoding gRNA and/or a CRISPR enzyme may be delivered or introduced by recombinant AAV.

In yet another example, a nucleic acid sequence encoding gRNA and/or a CRISPR enzyme may be delivered or introduced by one or more hybrids of hybrid viruses, for example, the viruses described herein.

The vector may be included in a bacterium and introduced into a subject.

Here, the vector may be included in an *Agrobacterium* and introduced into a subject, but the present invention is not limited thereto.

As an example, a vector including a nucleic acid sequence(s) encoding gRNA and/or a CRISPR enzyme may be included in an *Agrobacterium* and introduced into a plant body.

In one exemplary embodiment of the present invention, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

8. Transformant

The term "transformant" refers to an organism into which a guide nucleic acid, editor protein or guide nucleic acid-editor protein complex is introduced, an organism in which a guide nucleic acid, editor protein or guide nucleic acid-editor protein complex is expressed, or a specimen or sample obtained from the organism.

The transformant may be an organism into which a guide nucleic acid, editor protein or guide nucleic acid-editor protein complex is introduced in the form of DNA, RNA or a mixture thereof.

For example, the transformant may be an organism into which a vector including a nucleic acid sequence encoding a guide nucleic acid and/or editor protein is introduced. Here, the vector may be a non-viral vector, viral vector or recombinant viral vector.

In another example, the transformant may be an organism into which a nucleic acid sequence encoding a guide nucleic acid and/or editor protein is introduced in a non-vector form. Here, the non-vector may be naked DNA, a DNA complex, mRNA or a mixture thereof.

The transformant may be an organism into which a guide nucleic acid, editor protein or guide nucleic acid-editor protein complex is introduced in the form of a peptide, polypeptide or protein.

The transformant may be an organism into which a guide nucleic acid, editor protein or guide nucleic acid-editor protein complex is introduced in the form of DNA, RNA, a peptide, a polypeptide, a protein or a mixture thereof.

For example, the transformant may be an organism into which a guide nucleic acid-editor protein complex including an RNA-type guide nucleic acid and a protein-type editor protein is introduced.

The transformant may be an organism including a target nucleic acid, gene, chromosome or protein of the guide nucleic acid-editor protein complex.

The organism may be cells, tissue or a plant.

The cells may be prokaryotic cells or eukaryotic cells.

The eukaryotic cells may be plant cells, but the present invention is not limited thereto.

The tissue may be tissue of a plant body such as a root, a stem, a leaf, a flower, a fruit or a callus, and the like, etc.

The transformant may be a plant body into which a guide nucleic acid, editor protein or guide nucleic acid-editor protein complex is introduced or expressed, or a specimen or sample obtained from the plant body.

The specimen or sample may be a root, a stem, a leaf, a flower, a fruit, a callus or cells thereof.

Use

One exemplary embodiment of the present invention relates to a use for producing a composition for artificially manipulating an unsaturated fatty acid biosynthesis-associated factor of a subject such as a plant, a plant body in which the content of a specific unsaturated fatty acid is controlled by an artificially manipulated unsaturated fatty acid biosynthesis-associated factor, or a processed product using the same.

Specific Unsaturated Fatty Acids

Soybean (*Glycine max* L.)

Soybeans are the most widely cultivated crop in the worldwide, and provide the highest quality vegetable oil and proteins in terms of production and use. Transformation technology is widely used to improve genetic characteristics of various effective genes in soybeans. A transgenic soybean plant body has been developed using a transformation system using an *Agrobacterium* based on a cotyledonary-node (CN) method (Hinchee et al., 1988, Nat. Biotechnol., Vol. 6, 915-922), and recently, a system for producing a stable transformant was improved using half-see explants (Paz et al., 2006, Plant Cell Rep., Vol. 25, 206-213). Moreover, the application of a wound in a target site using a mixed use of a thiol compound, an *Agrobacterium* concentrate and ultrasound degradation resulted in a positive improvement in transformation efficiency (Meurer et al., 1998, Plant Cell Rep., Vol. 18, 180-186; Olhoft et al., 2003, Planta, Vol. 216, 723-735; Kim et al., 2013, Plant Biotechnol Rep., Vol. 7, 425-433; Kim et al., 2016, Plant Biotechnol Rep., Vol. 10, 257-267).

Soybean contains about 20% fat in the total composition, and the fat consists of fatty acids. The fatty acids consist of saturated fatty acids and unsaturated fatty acids. The unsaturated fatty acids consist of oleic acid, linoleic acid and α-linolenic acid. Among these, α-linolenic acid is a vegetable omega-3 fatty acid, which has been known to inhibit cancer cell growth, prevent a cardiovascular disease, inhibit inflammation and blood clotting, and degrade fat. Linoleic acid is an omega-6 fatty acid, and has been known to promote cancer cell growth, drop blood pressure, produce inflammation and thrombi, and accumulate fat, unlike α-linolenic acid.

It has been reported that a low ratio of omega-6/omega-3 in fats has an effect of inhibiting the above-mentioned diseases. In some examples, when the ratio is 4:1, prevention of a cardiovascular disease may be excellent and blood circulation may be improved, when the ratio is 2-3:1, the inflammation of rheumatoid arthritis may be inhibited, and therefore the most ideal ratio is known to be 2-1:1. The soybean oil contains 54% of the omega-6 fatty acid and 8% of the omega-3 fatty acid, and a ratio of the two fatty acids is significantly high at 6-7:1.

In the unsaturated fatty acid metabolism of soybean, it has been known that a FAD2 gene serves to change oleic acid to linoleic acid, and a FAD3 gene serves to change linoleic acid to α-linolenic acid. In the fatty acid metabolism, variations in the contents of oleic acid and linoleic acid by the mutation of the FAD2 gene has been reported. When there is a mutation in the FAD2 gene, the oleic acid content is increased, and the linoleic acid content is decreased, such that the ratio of the linoleic acid to the α-linolenic acid was adjusted, but there is a limitation in finding a satisfactory ratio of 4:1 or less. Therefore, it is necessary to control the contents of oleic acid and linoleic acid.

Specific Unsaturated Fatty Acids

One exemplary embodiment of the present invention may provide a plant body increased in the content of a specific unsaturated fatty acid or a processed product using the same.

Here, the specific unsaturated fatty acid may be a C8 to 24:D1 unsaturated fatty acid.

The specific unsaturated fatty acid may be a C16 to 22:D1 unsaturated fatty acid.

The specific unsaturated fatty acid may be a C18:D1 unsaturated fatty acid.

The specific unsaturated fatty acid may be oleic acid.

Alternatively, the specific unsaturated fatty acid may be an unsaturated fatty acid produced by removing one double bond from a C8 to 24:D2 unsaturated fatty acid, the specific unsaturated fatty acid may be an unsaturated fatty acid produced by removing one double bond from a C16 to 22:D2 unsaturated fatty acid, the specific unsaturated fatty acid may be an unsaturated fatty acid produced by removing one double bond from a C18:D2 unsaturated fatty acid, and the specific unsaturated fatty acid may be an unsaturated fatty acid produced by removing one double bond from linoleic acid.

Another exemplary embodiment of the present invention relates to a plant body decreased in the content of a specific unsaturated fatty acid or a processed product produced using the same.

Here, the specific unsaturated fatty acid may be a C8 to 24:D2 unsaturated fatty acid.

The specific unsaturated fatty acid may be a C16 to 22:D2 unsaturated fatty acid.

The specific unsaturated fatty acid may be a C18:D2 unsaturated fatty acid.

The specific unsaturated fatty acid may be linoleic acid.

Alternatively, the specific unsaturated fatty acid may be an unsaturated fatty acid produced by forming one double bond in a C8 to 24:D1 unsaturated fatty acid, the specific unsaturated fatty acid may be an unsaturated fatty acid produced by forming one double bond in a C16 to 22:D1 unsaturated fatty acid, the specific unsaturated fatty acid may be an unsaturated fatty acid produced by forming one double bond in a C18:D1 unsaturated fatty acid, and the specific unsaturated fatty acid may be an unsaturated fatty acid produced by forming one double bond in oleic acid.

Alternatively, the specific unsaturated fatty acid may be an unsaturated fatty acid produced by removing one double bond from a C8 to 24:D3 unsaturated fatty acid, the specific unsaturated fatty acid may be an unsaturated fatty acid produced by removing one double bond from a C16 to 22:D3 unsaturated fatty acid, the specific unsaturated fatty acid may be an unsaturated fatty acid produced by removing one double bond from a C18:D3 unsaturated fatty acid, and the specific unsaturated fatty acid may be an unsaturated fatty acid produced by removing one double bond from α-linolenic acid.

In one embodiment, the specific unsaturated fatty acid may be a C18:D1 unsaturated fatty acid or a C18:D2 unsaturated fatty acid.

In one embodiment, the specific unsaturated fatty acid may be oleic acid or linoleic acid.

In another exemplary embodiment, the present invention may provide a use of a system for controlling an additional third mechanism in a body, which is involved in various functions of a specific factor whose function is artificially modified (e.g., a gene known as an unsaturated fatty acid biosynthesis-associated factor).

For example, the specific factor whose function is artificially modified may be one or more genes selected from a FAD2 gene, a FAD3 gene, a FAD6 gene, a FAD7 gene and a FAD8 gene.

The third mechanism may be a mechanism in a plant body, other than the biosynthesis of an unsaturated fatty acid, involved in these genes.

Compositions for Controlling Unsaturated Fatty Acid

One exemplary embodiment of the present invention relates to a composition used to control the content of an unsaturated fatty acid of a plant using an artificially manipulated unsaturated fatty acid biosynthesis-associated factor.

The composition may include an artificially manipulated unsaturated fatty acid biosynthesis-associated factor or a manipulation composition that can artificially manipulate an unsaturated fatty acid biosynthesis-associated.

In one exemplary embodiment, the composition may include an artificially manipulated unsaturated fatty acid biosynthesis-associated factor, that is, a gene and/or a protein.

In one exemplary embodiment, the composition may include a manipulation composition that can artificially manipulate an unsaturated fatty acid biosynthesis-associated factor.

The manipulation composition may include a guide nucleic acid-editor protein complex.

The manipulation composition may include a guide nucleic acid and/or editor protein.

The manipulation composition may include a nucleic acid encoding the guide nucleic acid and/or editor protein.

The manipulation composition may include a virus comprising a nucleic acid encoding the guide nucleic acid and/or editor protein.

In another exemplary embodiment, the composition may further include an additional element.

The additional factor may include a suitable carrier for transferring it into a plant body of a subject.

In an exemplary embodiment, the composition may include an expression product of an unsaturated fatty acid biosynthesis-associated factor which is manipulated to an amount sufficient to increase or decrease the content of a specific unsaturated fatty acid.

The "amount sufficient to increase or decrease the content of a specific unsaturated fatty acid" means an effective amount required to increase or decrease the content of a specific unsaturated fatty acid.

In one exemplary embodiment, the present invention may provide compositions for controlling an unsaturated fatty acid as follows:

A composition for controlling the content of a specific unsaturated fatty acid, which includes a guide nucleic acid capable of forming a complementary bond independently with one or more target sequences in the nucleic acid sequence of one or more genes selected from the group consisting of a FAD2 gene, a FAD3 gene, a FAD6 gene, a FAD7 gene and a FAD8 gene, or a nucleic acid sequence encoding the same, and
  an editor protein or a nucleic acid sequence encoding the same;
a composition for controlling the content of a specific unsaturated fatty acid, which includes a guide nucleic acid capable of forming a complementary bond independently with a target sequence of one or more genes selected from the group consisting of a FAD2 gene, a FAD3 gene, a FAD6 gene, a FAD7 gene and a FAD8 gene, or a nucleic acid sequence encoding the same; and
  an editor protein or a nucleic acid sequence encoding the same; and
a composition for controlling the content of a specific unsaturated fatty acid, which includes a complex formed of a guide nucleic acid capable of forming a complementary bond independently with a target sequence of one or more genes selected from the group consisting of a FAD2 gene, a FAD3 gene, a FAD6 gene, a FAD7 gene and a FAD8 gene, or a nucleic acid sequence encoding the same, and an editor protein.

Here, a guide nucleic acid or a nucleic acid sequence encoding the same; and a nucleic acid sequence encoding the editor protein may be present in the form of one or more vectors. They may be present in the form of a homologous or heterologous vector.

Method of Controlling Unsaturated Fatty Acid

In another exemplary embodiment of the present invention, the present invention provides a method of controlling the content of an unsaturated fatty acid, which includes producing the above-described composition and administering an effective amount of the composition to a target plant body.

Gene Manipulation

A method of controlling the content of an unsaturated fatty acid by manipulating the gene of a body may be used. Such a controlling method may consist of introducing the composition for genetic manipulation for manipulating the gene of a plant body into the plant body.

The composition for genetic manipulation may include a guide nucleic acid-editor protein complex.

The composition for genetic manipulation may be injected into a specific plant type.

Here, the specific plant type may be a seed, but the present invention is not limited thereto.

In one aspect, the present invention may provide a method of modifying a target polynucleotide in plant cells.

In one exemplary embodiment, the method includes obtaining cells or a cell population from a plant as a sample, and modifying the cells or cell population. The culturing may be performed at any step outside a plant body. The cell or cells may be re-introduced into a plant.

In addition, in another exemplary embodiment, the present invention may provide a method of artificially manipulating cells, which includes:
  introducing (a) a guide nucleic acid capable of forming a complementary bond with each of target sequences of one or more genes selected from the group consisting of a FAD2 gene, a FAD3 gene, a FAD6 gene, a FAD7 gene and a FAD8 gene, or a nucleic acid sequence encoding the same; and
  (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Staphylococcus aureus*-derived Cas9 protein, a *Neisseria meningitidis*-derived Cas9 protein and a Cpf1 protein, or a nucleic acid sequence encoding the same to plant cells.

The guide nucleic acid and the editor protein may be present in one or more vectors in the form of a nucleic acid sequence, or in a complex of a combination of the guide nucleic acid and the editor protein.

A technique of the above-described "7. Delivery" section may be referenced before the introduction step.

For example, the introduction stage may be achieved by one or more methods selected from a gene gun, electroporation, liposomes, plasmids, viral vectors, nanoparticles, and a protein translocation domain (PTD) fusion protein method.

For example, the viral vector may be one or more selected from the group consisting of a mosaic virus, a retrovirus, a lentivirus, an adenovirus, adeno-associated virus (AAV), vaccinia virus, a poxvirus and a herpes simplex virus.

For example, a vector may be included in agrobacteria and introduced.

When an unsaturated fatty acid biosynthesis-associated factor is artificially manipulated using the methods and compositions according to some exemplary embodiments of the present invention, it is possible to control the type and/or content of an unsaturated fatty acid, for example, an increase or decrease of a specific unsaturated fatty acid, and/or a change in the content of a specific unsaturated fatty acid, and therefore, a plant in which an unsaturated fatty acid advantageous for human health is increased or a harmful unsaturated fatty acid is decreased, and/or a processed product (food, etc.) thereof may be obtained.

Additional Uses

In any exemplary embodiment, the present invention may provide a kit for preparing a composition for controlling the content of an unsaturated fatty acid, which includes the composition.

The kit may be prepared by a conventional preparation method known in the art.

The kit may further include a detectable label. The term "detectable label" refers to an atom or molecule for specifically detecting a molecule containing a label among the same type of molecules without a label. The detectable label may be attached to an antibody specifically binding to a protein or a fragment thereof, an interaction protein, a ligand, nanoparticles, or an aptamer. The detectable label may include a radionuclide, a fluorophore, and an enzyme.

In any exemplary embodiment, the present invention may provide a method of screening a material capable of controlling an expression level of one or more genes selected from a FAD2 gene, a FAD3 gene, a FAD6 gene, a FAD7 gene and a FAD8 gene, which are artificially manipulated.

In any exemplary embodiment, the present invention may provide a method of providing information on the sequence at an artificially manipulated target position to a subject by analyzing the sequence of one or more genes selected from the group consisting of a FAD2 gene, a FAD3 gene, a FAD6 gene, a FAD7 gene and a FAD8 gene.

In addition, the present invention provides a method of constructing a library using the provided information.

Here, a known database may be used.

In specific exemplary embodiments, the present invention may provide a plant or cells that can be used for research using the method of the present invention.

A plant or cells that include a chromosome editing in one or more nucleic acid sequences associated with the biosynthesis of an unsaturated fatty acid may be produced using the method of the present invention. The nucleic acid sequence may be a sequence that can encode a protein sequence associated with the biosynthesis of an unsaturated fatty acid, or a reference sequence associated with the biosynthesis of an unsaturated fatty acid.

In one exemplary embodiment, the effect of mutation and the mechanism of the biosynthesis of an unsaturated fatty acid may be studied in a plant or cells using measurement conventionally used in a study related to the biosynthesis of an unsaturated fatty acid using the plant or cells manufactured by the method of the present invention. Alternatively, the effect of an active compound in the biosynthesis of an unsaturated fatty acid may be studied using the plant or cells.

In another exemplary embodiment, the effect of an available gene manipulation strategy may be evaluated using the plant or cells manufactured by the method of the present invention. In other words, by modifying a chromosomal sequence encoding a protein related to the biosynthesis of an unsaturated fatty acid, the biosynthesis of the corresponding unsaturated fatty acid may be promoted or inhibited. Particularly, this method includes forming a modified protein by editing a chromosomal sequence encoding a protein related to the biosynthesis of an unsaturated fatty acid, resulting in modification of the plant or cells. Therefore, in some exemplary embodiments, an effect of the genetically modified plant may be evaluated by comparing a mechanism of the biosynthesis of an unsaturated fatty acid with that of a wild-type.

The genetically modified plant may be used to produce a plant body which is increased or decrease in specific unsaturated fatty acids by an artificially manipulated unsaturated fatty acid biosynthesis-associated factor and a system for controlling an unsaturated fatty acid, which is artificially modified in function by the same. Through the control of various mechanisms involved in a variety of unsaturated fatty acid biosynthesis-associated factors, a system for controlling an unsaturated fatty acid may be improved.

EXAMPLES

Hereinafter, the present invention will be described in further detail with reference to examples.

These examples are merely provided to describe the present invention in further detail, and it might be obvious to those of ordinary skill in the art that the scope of the present invention is not limited to the following examples.

Experimental Methods 1. gRNA Design

A CRISPR/Cas9 target site of a FAD2 gene of soybean was selected using CRISPR RGEN tools (Institute for Basic Science, Korea). The target site of each gene may be different according to the type of a CRISPR enzyme, and a target sequence of the gene for SpCas9 was summarized in Table 1 described above.

2. Construction of Vector for Soybean Transformation

In a soybean transformation test, a pPZP vector including gRNA of FAD2-7 or FAD2-30 for targeting a FAD2 gene was used, and the vector also includes Cas9. An *Agrobacterium tumefaciens* strain, EHA105, was transformed with the constructed pPZP-FAD2-7 and pPZP-FAD2-30 vectors (FIG. 1).

3. Soybean Transformants and Production of $T_1$ Seeds

1) Sterilization and Soaking of Seeds

Seeds were sterilized with hydrochloric acid gas generated by mixing chlorine bleach (100 mL of 12% sodium hypochlorite) with strong hydrochloric acid (12N HCl, 5 mL) for 20 hours, suspension-cultured in 1% sodium hypochlorite for 10 minutes for secondary sterilization, and washed with sterile water three times at an interval of 10 minutes. Each of the sterile seeds was put into a 50 mL conical tube, and then sterile water was poured into the conical tube to perform soaking at room temperature for 20 hours.

2) Preparation of Inoculum (*Agrobacterium tumefaciens*)

In a soybean transformation test, the pPZP-FAD2-7 and pPZP-FAD2-30 vectors constructed in the *Agrobacterium tumefaciens* strain EHA105 were used, and include PPTR. A bacterial strain containing the vector was streaked on a solid YEP medium [75 mg/L of spectinomycin, 25 mg/L of rifampicin, 10 g/L of peptone, 5 g/L of NaCl, 5 g/L of an yeast extract, 1.5% (w/v) agar (pH 7.0)] and cultured at 28° C., thereby obtaining a single colony. The colony was suspended in 10 mL of a liquid YEP medium containing the same antibiotic included in the solid YEP medium, and stirred at 220 rpm at 28° C. until OD650 reached 0.6 to 0.8. 10 mL of a 30% glycerol stock was added to and mixed with the fully-grown bacterial cells, 1 mL of the cell suspension was dispensed to each 1.5 mL tube, rapidly cooled with liquid nitrogen, and stored at −70° C. One day before inoculation, 1 mL of the *Agrobacterium tumefaciens* stock that had been stored at −70° C. was added to 200 mL of a liquid YEP medium containing an antibiotic, and shake-cultured in an incubator at 250 rpm at 25° C. until OD650 reached 0.6 to 0.8. On the day of inoculation, 200 mL of a liquid YEP medium was divided into 50 mL, and centrifuged at 20° C. and 3,270 g for 10 minutes. 15 mL of a liquid co-cultivation medium (CCM; 0.32 g/L of B5 salt, 1.67 mg/L of BA, 20 mM MES, 0.25 mg/L of GA3, 0.2 mM acetosyringone, 3.3 mM L-Cysteine, 1.0 mM sodium thiosulfate, 1.0 mM DTT, 3% sucrose, pH 5.4) was added to the *Agrobacterium tumefaciens* pellet in each tube.

3) Inoculation and Cocultivation

After the soaked seed was vertically cut to the hypocotyl by a scalpel inserted between the both cotyledons, a seed coat was removed. The embryonic axis was cut at about 1 cm beneath the cytoledon, and one side to which the embryonic axis was attached was wounded 7 to 8 times with a scalpel (#11 blade). Here, the scalpel was coated with a 15 mL concentrate, and a wound was made in a target site. About 50 explants were put into 15 mL co-culture/*Agrobacterium tumefaciens* and sonicated for 20 seconds, followed by inoculation for 30 minutes. After each explant was taken out of the tube and put on a filter paper to remove moisture, a sheet of filter paper was put on solid CCM (the same as liquid CCM, agar (0.7%)), and then 10 explants were put thereon (to place the adaxial side down). The plate was sealed with a micropore tape, and co-cultured photoperiodically for 18 hours at 25° C. for 5 days.

4) Washing and Shoot Induction

Five days after the co-culture, the explants were briefly washed with a liquid ½ shoot induction medium (SIM) for 10 minutes for sterilization. The explants were placed on a filter paper to remove moisture, and then six explants per plate were embedded in plates containing selectable antibiotic-free SI-① (shoot induction medium; 3.2 g/L of B5 salt, 1.67 mg/L of BA, 3 mM MES, 0.8% agar, 3% sucrose, 250 mg/L of cefotaxime, 50 mg/L of vancomycin, 100 mg/L of ticarcillin, pH 5.6), and a regeneration part of the explant was positioned with side up at an angle of about 30°. Each plate was sealed with a micropore tape and cultured photoperiodically at 25° C. for 18 hours.

After two weeks, shooting explants were embedded in 10 mg/L of selectable antibiotic PPT-containing SI-② (the same as SI-①, 10 mg/L of DL-phosphinothricin was added, pH 5.6), and the other part excluding a shoot was removed and embedded so that the adaxial part faced downward.

5) Shoot Elongation

After two weeks, a browning shoot/shoot pad was excised with a scalpel (#15 blade) and embedded in a 5 mg/L selectable antibiotic PPT-containing shoot elongation medium (SEM; 4.4 g/L of MS salt, 3 mM MES, 0.5 mg/L GA3, 50 mg/L asparagine, 100 mg/L pyroglutamic acid, 0.1 mg/L IAA, 1 mg/L zeatin, 3% sucrose, 0.6% agar, 250 mg/L cefotaxime, 50 mg/L vancomycin, 100 mg/L ticarcillin, 5 mg/L DL-phosphinothricin, pH 5.6). Every two weeks, the shoot/shoot pad was transferred to fresh SEM, and the browning part of the shoot was removed by using the upper side of a scalpel (#15 blade), and the shoot pad was shaved off gradually so that the medium was well absorbed. When the shoot was grown up to the lid of the petri dish, two petri dishes (100 mm×40 mm) were stacked so that the shoot was grown to about 8 cm. Each plate was sealed with a micropore tape, and incubated photoperiodically at 25° C. for 18 hours.

6) Rooting, Acclimatization and PPT Leaf Painting

When the shoot elongated through selection on SEM was 4 cm or more, the shoot was excised with a scalpel (#11 blade) and transferred to a rooting medium (RM; 4.4 g/L of MS salt, 3 mM MES, 3% sucrose, 0.8% agar, 50 mg/L cefotaxime, 50 mg/L vancomycin, 50 mg/L ticarcillin, 25 mg/L asparagine, 25 mg/L pyroglutamic acid, pH 5.6). Here, the lower part of the elongated shoot separated by cutting was dipped in 1 mg/mL IBA for three minutes, and then put into a test tube containing RM.

When the root was sufficiently grown, the medium was washed off from the root with tertiary distilled water. The grown root was transplanted into a small pot (6 cm×6 cm×5.6 cm) containing a mixture of bed soil (Bio Plug No. 2, Heungnong seeding) and vermiculite (2:1) and placed in a Magenda box. About 10 days later, a leaf surface was painted with 100 mg/L DL-phosphinothricin.

7) Production of $T_1$ Seeds

When the plant body was sufficiently grown, the plant body was transplanted into a larger pot, and covered with a transparent plastic lid having about 10 pores. After 10 days, the plant body was treated with Basta® (BAYER, 53 mg/L). As a result, non-transformants (*Glycine max* L. Kwangan, NT) sensitively reacted and thus failed, but transformants did not show any change and exhibited resistance. Nine soybean transformants (eight pPZP-FAD2-7 and one pPZP-FAD2-30) exhibiting resistance were transferred to a green house, thereby obtaining $T_1$ seeds.

8) Removal of $T_1$ Transformant-Introduced Gene and Production of $T_2$ Seeds

To confirm that a transgenic $T_1$ plant body-induced gene was removed, $T_1$ seeds were sowed and the plant body was grown 15 cm or more over a small port and had 9 or more leaves, followed by performing leaf painting with phosphinothricin. The selected transgenic plant body was transferred to a larger pot (20 cm (diameter)×25 cm (height)) and grown in a greenhouse to obtain a $T_1$ sample and obtain T2 seeds.

4. Gene Transfer Analysis 1 g of leaves of transient transformants were quantified and frozen with liquid nitrogen, and the frozen leaves were well grinded in a mortar, followed by extracting genomic DNA using a CTAB method. To determine whether a gene was introduced, PCR was performed using sequences of gRNA FAD2-7 and FAD2-30, selectable gene Bar and a Cas9 gene. To confirm the introduction of FAD2-7 and FAD2-30 genes, the following primers were used.

For the FAD2-7 gene, promoter AtU6p forward primer (5'-GAATGATTAGGCATCGAACC-3'(SEQ ID NO: 31) and FAD2-7 reverse primer (5'-AAACTCCT-CAAGGGTTCCAAACAC-3'(SEQ ID NO: 31)) were used. For the FAD2-30 gene, promoter AtU6p forward primer (5'-GAATGATTAGGCATCGAACC-3'(SEQ ID NO: 31)) and FAD2-7 reverse primer (5'-AAACTCCT-CAAGGGTTCCAAACACC-3'(SEQ ID NO: 33)) were used. To confirm the introduction of the Bar gene, Bar forward primer (5'-TCCGTACCGAGCCGCAGGAA-3' (SEQ ID NO: 34)) and Bar reverse primer (5'-CCGGCAGGCTGAAGTCCAGC-3'(SEQ ID NO: 35)) were used.

In addition, to confirm the introduction of Cas9, PCR was performed using three primer sets as follows: a set of Cas9-① forward primer (5'-ATGGACAAGAAGTACAG-CATCGGC-3'(SEQ ID NO: 36)) and Cas9-① reverse primer (5'-AACTTGTAGAACTCCTCCTGGCTG-3'(SEQ ID NO: 37)); a set of Cas9-② forward primer (5'-TTCAG-GAAGTCCAGGATGGTCTTG-3'(SEQ ID NO: 38)) and Cas9-② reverse primer (5'-AGAACTG-GAAGTCCTTGCGGAAGT-3'(SEQ ID NO: 39)); and a set of Cas9-③ forward primer (5'-CT-GAGCGAGCTGGACAAGGCCGG-3'(SEQ ID NO: 40))

and Cas9-③ reverse primer (5'-TTAGGCGTAGTCGGGCACGTCGTA-3'(SEQ ID NO: 41)) were used.

5. Gene Removal Analysis 1 g of leaves of a transgenic $T_1$ plant body were quantified and frozen with liquid nitrogen, and the frozen leaves were well grinded in a mortar. 0.5 g of the grinded leaves were put into a 2 mL tube, 1 mL of a solution prepared by mixing cetyltrimethylammonium (cTAB) buffer and β-mercaptoethanol (2-ME) in a ratio of 20:1 was added and treated in a 65° C. heat-block for 1 hour, and then 10 μL of RNase (1.5 mg/150 μL $H_2O$) was added to allow incubation at 37° C. for 1 hour. After one hour, chloroform:isoamyl alcohol (24:1) were mixed in the same volume and well mixed to prepare a reagent, and then centrifuged at 4° C. and 12,000 rpm for 10 minutes. A supernatant was transferred to a new tube, and treated with a chloroform:isoamylalchol (24:1) reagent once again. After a supernatant was put into the same volume of isopropanol and mixed by being inverted 3 to 4 times, placed in a −20° C. refrigerator for 1 hour, and centrifuged at 4° C. and 12,000 rpm for 10 minutes. After a supernatant was discarded, 1 mL of 70% ethanol was added thereto, and the resulting solution was centrifuged again for 2 minutes, thereby obtaining a pellet. After a supernatant was discarded, the pellet was dried at room temperature for 20 minutes and then suspended in 30 μL of distilled water to extract genomic DNA. The extracted genomic DNA was diluted 20-fold, and used as a template.

The base sequences of the introduced gene and the selectable antibiotic gene BAR were subjected to 35 cycles of PCR consisting of pre-denaturation at 95° C. for 10 minutes, denaturation at 95° C. for 30 seconds, annealing at 55 to 65° C. for 30 seconds and extension at 72° C. for 30 seconds to 1.5 minutes, and additionally subjected to extension at 72° C. for 10 minutes, and the result was determined using a PCR kit (Prime Taq Premix, GENETBIO, Korea).

6. Analysis of Oleic Acid Content

For fatty acid analysis, three soybean seeds obtained from each transformant was individually analyzed. Each seed was put into a paper bag, crushed using a hammer, and fatty acid was extracted using 5 mL of an extraction solvent (chloroform:hexane:methanol, 8:5:2) at room temperature for 12 hours. 150 μL of the extracted fatty acid was transferred to a vial, 75 μL of a methylation reagent (0.25M methanolic sodium methoxide:petroleum ether:ethyl ether, 1:5:2) was added, and then hexane was added to reach 1 mL. 1 μL of a sample was injected and analyzed using a gas chromatography apparatus (GC, Aglient Technologies, USA), and analysis conditions are shown in Table 2 below. A fatty acid ratio was calculated with an area of each fatty acid with respect to the total area of the fatty acids.

TABLE 2

Table 2. GC conditions for analyzing fatty acid in soybean

| Item | Condition |
| --- | --- |
| Instrument | Agilent 7890A |
| Column | 0.25 μm i.d. × 30 m DB-FFAP capillary column |
| Detector | Flame ionization detector |
| Oven temperature | 230° C. |
| Injection temperature | 210° C. |
| Detector temperature | 250° C. |
| Carrier gas | $N_2$ (1.5 mL/min) |
| Injection volume | 1 μL |

7. Analysis of FAD2 Gene Sequence

PCR-amplification was performed for a target region to have a size of 200 to 300 bp using Hipi Plus DNA polymerase (Elpisbio). The PCR product obtained by the above-described method was subjected to sequencing using a MiSeq system (Illumina), and then analyzed using a Cas analyzer, CRISPR RGEN tool (www.rgenome.net)).

Example 1. Transformant Vector and Production of Transformant

Figure 2A:
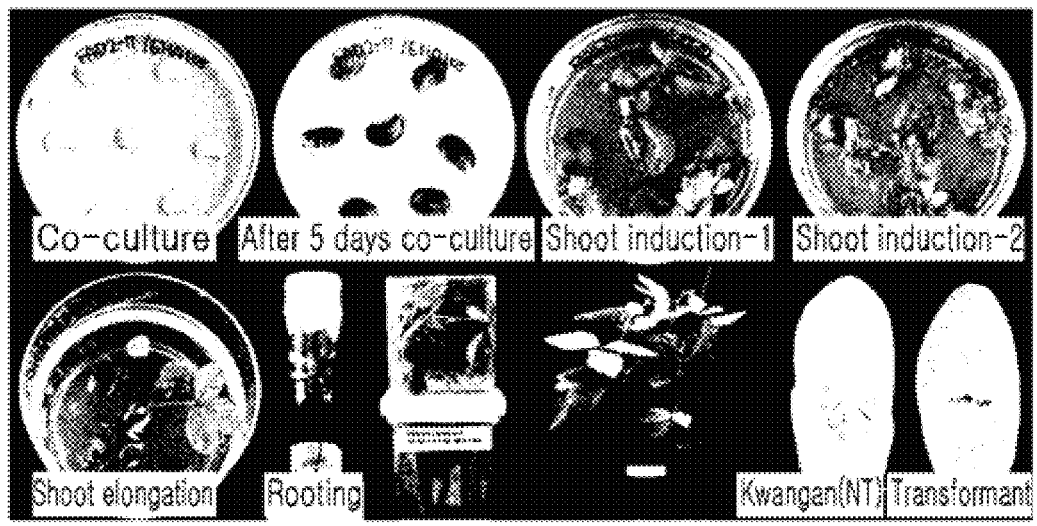
FIGS. 2A and 2B illustrates the growth processes of soybean transgenic plant bodies prepared by the knockout of a FAD2 gene using pPZP-FAD2-7(a) and pPZP-FAD2-30 (b).
Figure 2B:
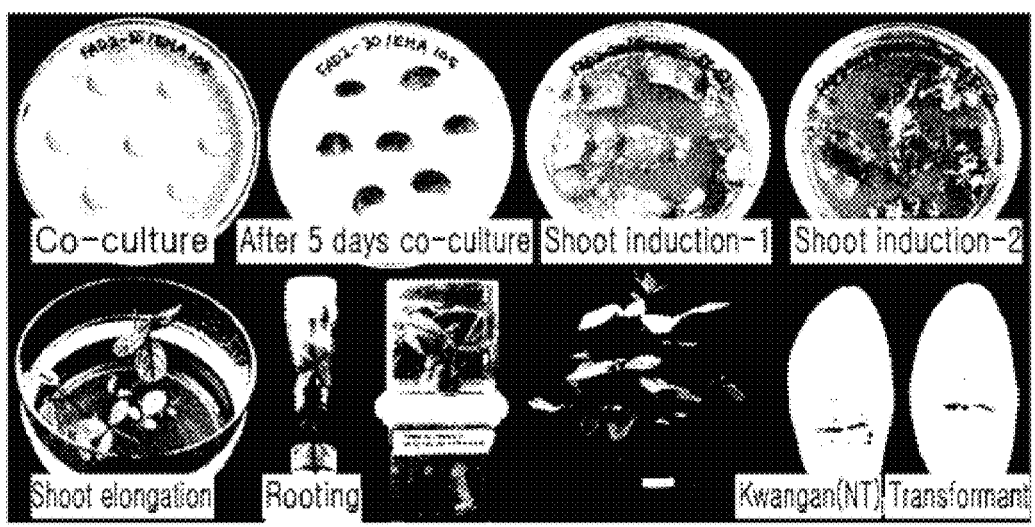
Figure 3:
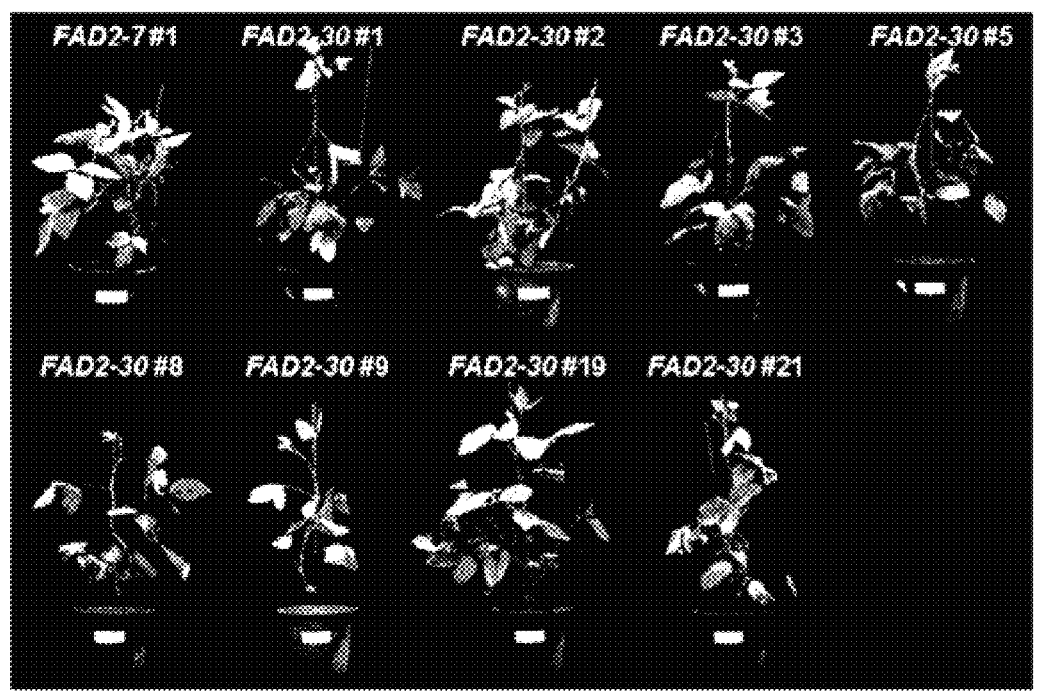
FIG. 3 shows T0 transformants of pPZP-FAD2-7 and pPZP-FAD2-30.
Figure 10:
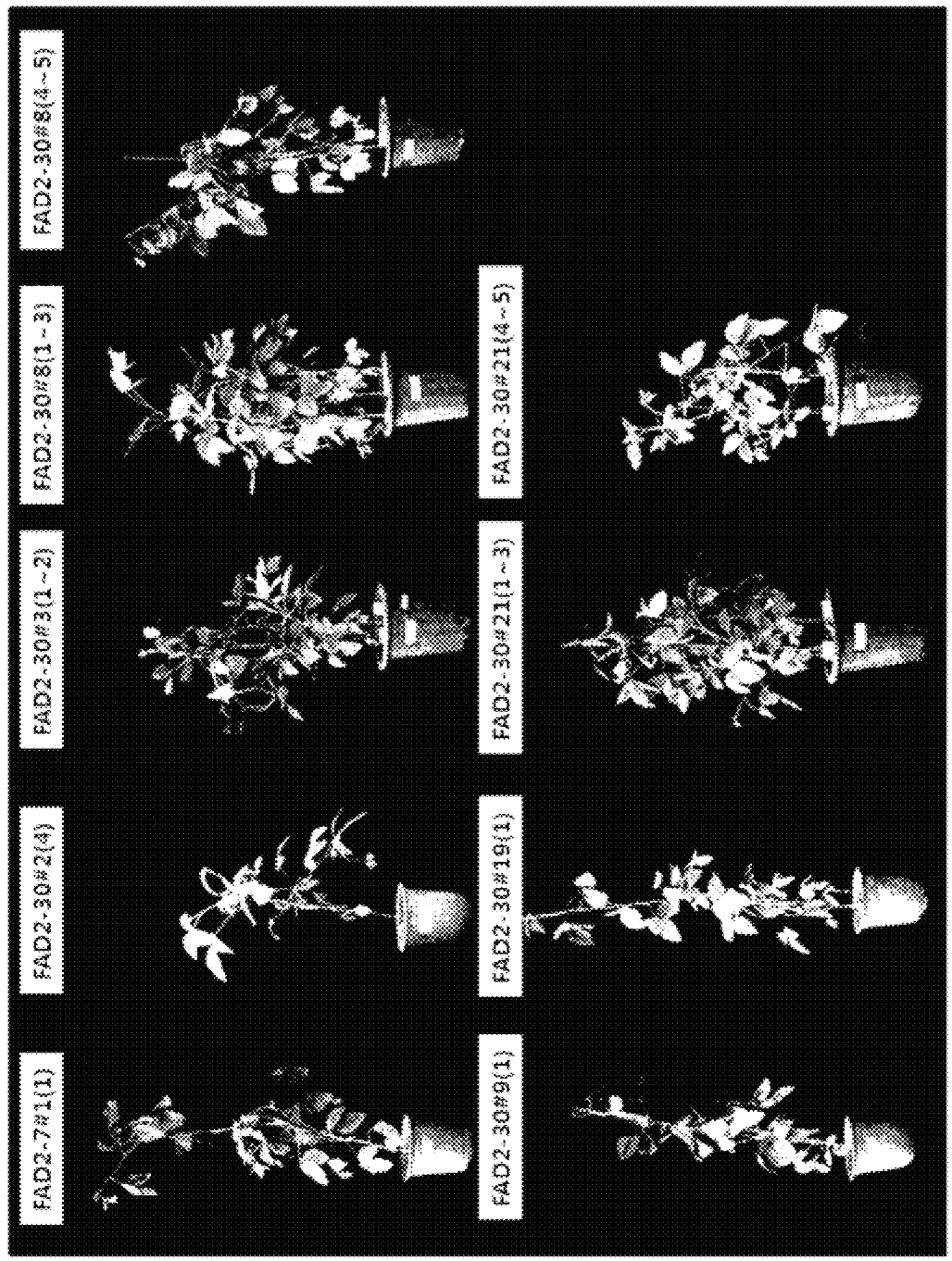
FIG. 10 shows $T_1$ transformants of pPZP-FAD2-7 and pPZP-FAD2-30.

To knock out the FAD2 gene, as shown in Table 1, guide RNA targeting the FAD2 gene was designed, and cloned with a Cas9 protein in a pPZP vector, thereby constructing a vector for soybean transformation (FIG. 1). As shown in FIG. 2, through the regeneration process of a plant, a total of 9 transformants (T0) (eight pPZP-FAD2-7 8 and one pPZP-FAD2-30) were produced (FIG. 3). $T_1$ seeds were collected from the transformants T0, thereby producing transformants $T_1$ (FIG. 10).

Example 2. PCR Analysis for Determining Gene Transfer into Transformant

Figure 4:
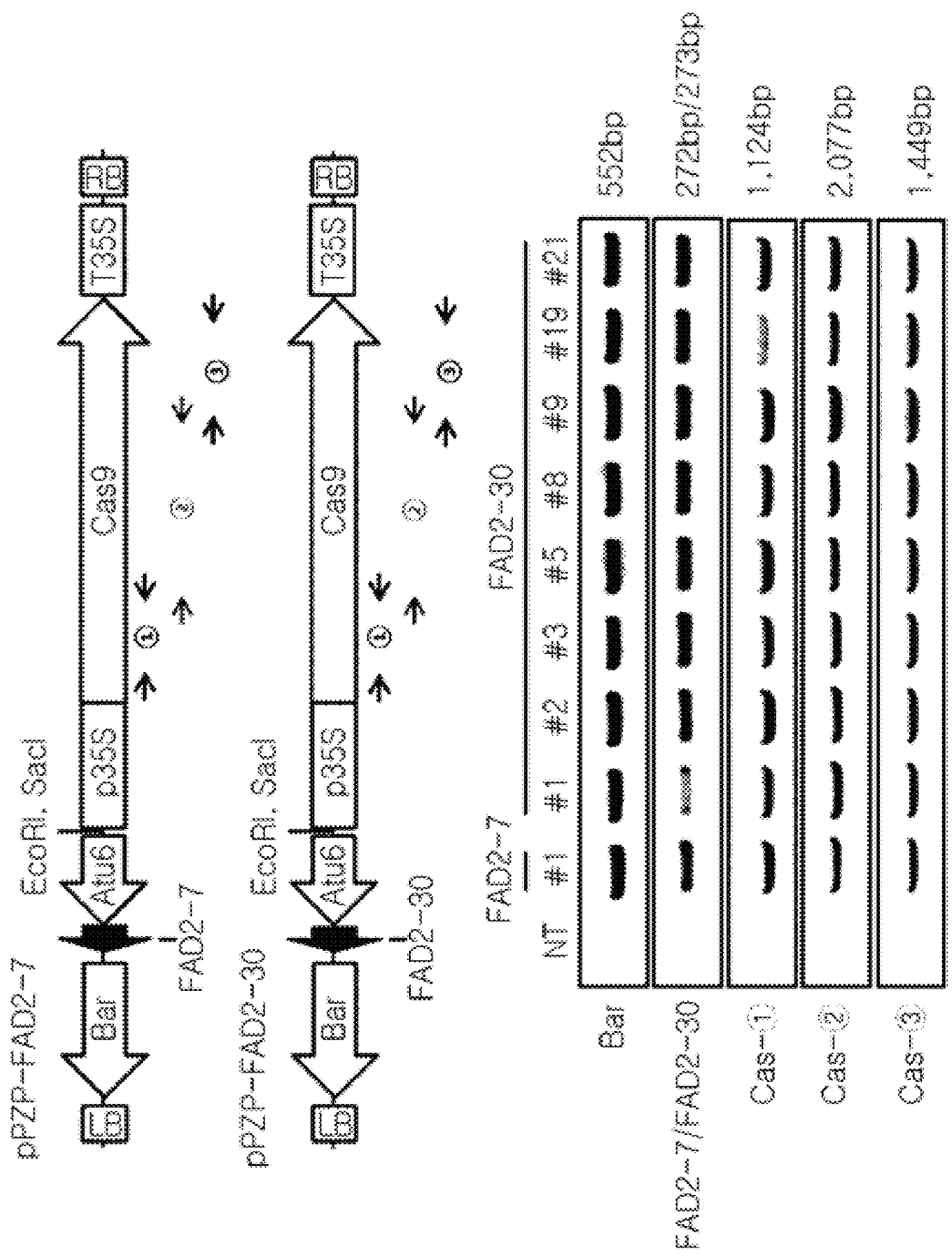
FIG. 4 shows the PCR results for confirming insert genes of the T0 transformants of pPZP-FAD2-7 and pPZP-FAD2-30. Here, NT is *Glycine max* L. Kwangan (wild type), and #1, #2, #3, #5, #8, #9, #19 and #21 are T0 transformants.

DNA was isolated from the FAD2-7 and FAD2-30 T0 transformants and subjected to PCR according to the above-described method, confirming all of the introduction of introduced guide RNA, FAD2-7 and FAD2-30, and selectable gene Bar and Cas9 (FIG. 4).

Example 3. Analysis of Oleic Acid Content in Transgenic Soybean

The contents of oleic acid were analyzed from the FAD2-7 and FAD2-30 $T_1$ seeds according to the above-described method. The contents of oleic acid in the FAD2-7 and FAD2-30 $T_1$ seeds were significantly higher than those of wild-type seeds such as Glycine max L. Pungsan, Glycine max L. Kwangan and Glycine max L. Hosim (FIG. 5).

Example 4. Analysis of FAD2 Gene Sequence in Transgenic Soybean

Indel frequencies (FIG. 6) and sequences (FIG. 7) were analyzed to confirm whether a mutation was induced in FAD2 genes of the FAD2-7 and FAD2-30 $T_1$ seeds according to the above described method. It was confirmed that a mutation was induced in the FAD2-7 $T_1$ seed.

In addition, $T_1$ transformants were analyzed through deep sequencing to confirm whether mutation was induced in a FAD2 gene. As a result, it was confirmed that a mutation was induced into a target site of a FAD2 gene in chromosome #10 (chr10) and chromosome #20 (chr20) of other $T_1$ transformants except FAD2-7 #1-1 and FAD2-30 #2-4, #9-1 and #3-1 (FIGS. 8 and 9).

Example 5. Analysis of Removal of Introduced Gene of Transgenic Soybean

Figure 11:
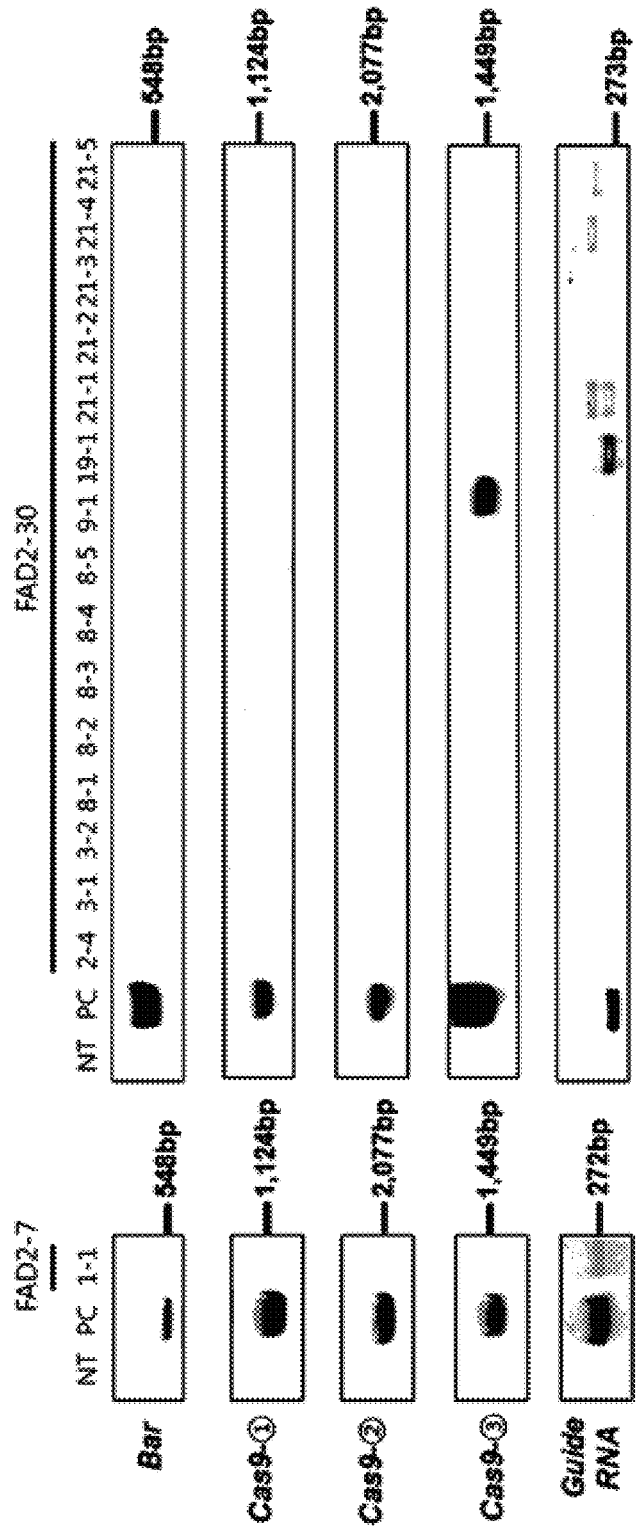
FIG. 11 shows the analysis results of the removal of a gene from $T_1$ transformants of pPZP-FAD2-7 and pPZP-FAD2-30 using PCR.

To confirm gene removal from selected $T_1$ transformants, PCR was performed for a selectable gene BAR and an introduced gene of an introduced vector. As a result, it was confirmed that, from one FAD2-7 $T_1$ transformant, both of the introduced gene and the BAR gene were removed, and among fifteen FAD2-30 $T_1$ transformants, individuals (9-1, 19-1, 21-1, 21-5) from which genes were not partially removed were confirmed (FIG. 11).

INDUSTRIAL APPLICABILITY

A processed product may be manufactured using plant body increased in the content of a specific unsaturated fatty acid which is good for human health or decreased in the content of a specific unsaturated fatty acid which is harmful for human health by using an artificially manipulated unsaturated fatty acid biosynthesis-associated factor and a system for controlling an unsaturated fatty acid, which is artificially modified thereby, and thus can be used for food.

This application contains references to amino acid sequences and/or nucleic acid sequences which have been submitted concurrently herewith as the sequence listing text file entitled "000003usdva_SequenceListing.TXT", file size 20 KiloBytes (KB), created on Mar. 28, 2022. The aforementioned sequence listing is hereby incorporated by reference in its entirety pursuant to 37 C.F.R. § 1.52(e)(5).

What is claimed is:

1. A method for producing an engineered soybean plant including a modified FAD2 gene in a genome, comprising:
    preparing a soybean seed,
    introducing a composition to the soybean seed to induce an indel modification in the genome of the soybean seed,
    wherein the composition comprises:
        a guide RNA capable of only targeting a FAD2 gene, or a nucleic acid sequence encoding the guide RNA; and
        an editor protein, or a nucleic acid sequence encoding the editor protein,
            wherein the guide RNA is an RNA sequence that targets a target sequence consisting of the sequence SEQ ID NO: 30,
            wherein the editor protein is a *Streptococcus pyogenes* derived Cas9 protein;
    obtaining an engineered soybean seed having the indel modification, wherein the indel modification is introduced into the sequence SEQ ID NO: 30 in the FAD2 gene sequence in the genome, and
    regenerating the engineered soybean seed to obtain the engineered soybean plant having the indel modification in the FAD2 gene sequence in the genome,
    wherein a soybean seed produced by the engineered soybean plant has a content of C18:D1 unsaturated fatty acid comprising about 70% to about 83% of the total fatty acids of the soybean seed.

2. The method of claim 1, wherein the indel modification is a deletion.

3. The method of claim 1, wherein the introducing the composition to the soybean seed is performed by an *Agrobacterium* vector comprising the composition, and
    wherein the composition comprises the nucleic acid sequence encoding the guide RNA and the nucleic acid sequence encoding the editor protein.

4. The method of claim 3, wherein the *Agrobacterium* is *Agrobacterium tumefaciens*.

5. A composition for use in the method of claim 1, comprising:
    a guide RNA capable of only targeting a FAD2 gene sequence, or a nucleic acid sequence encoding the guide RNA; and
    an editor protein, or a nucleic acid sequence encoding the editor protein,
        wherein the guide RNA is an RNA sequence that targets a target sequence consisting of the sequence SEQ ID NO: 30 in the FAD2 gene sequence,
        wherein the editor protein is a *Streptococcus pyogenes*-derived Cas9 protein, and
        wherein the composition induces an indel modification in the genome of a soybean seed.

6. The composition of claim 5, wherein the composition is capable of being transferred to the soybean seed via an *Agrobacterium* vector system, and
    wherein the composition comprises the nucleic acid sequence encoding the guide RNA and the nucleic acid sequence encoding the editor protein.

7. The composition of claim 6, wherein the *Agrobacterium* is *Agrobacterium tumefaciens*.

* * * * *

SEQUENCE LISTING

```
<160> NUMBER OF SEQ ID NOS: 120

<210> SEQ ID NO 1
<211> LENGTH: 23
<212> TYPE: DNA
<213> ORGANISM: Glycine max

<400> SEQUENCE: 1
atagattggc catgcaatga ggg                                           23

<210> SEQ ID NO 2
<211> LENGTH: 23
<212> TYPE: DNA
<213> ORGANISM: Glycine max

<400> SEQUENCE: 2
aatagattgg ccatgcaatg agg                                           23

<210> SEQ ID NO 3
<211> LENGTH: 23
<212> TYPE: DNA
<213> ORGANISM: Glycine max

<400> SEQUENCE: 3
ccttggagaa cccaatagat tgg                                           23

<210> SEQ ID NO 4
<211> LENGTH: 23
<212> TYPE: DNA
<213> ORGANISM: Glycine max

<400> SEQUENCE: 4
tgggtgattg ctcacgagtg tgg                                           23

<210> SEQ ID NO 5
<211> LENGTH: 23
<212> TYPE: DNA
<213> ORGANISM: Glycine max

<400> SEQUENCE: 5
ttttagtccc ttatttctca tgg                                           23

<210> SEQ ID NO 6
<211> LENGTH: 23
<212> TYPE: DNA
<213> ORGANISM: Glycine max

<400> SEQUENCE: 6
aaacacttca tcacggtcaa ggg                                           23

<210> SEQ ID NO 7
<211> LENGTH: 23
<212> TYPE: DNA
```

<213> ORGANISM: Glycine max

<400> SEQUENCE: 7
gtgtttggaa cccttgagag agg                                              23

<210> SEQ ID NO 8
<211> LENGTH: 23
<212> TYPE: DNA
<213> ORGANISM: Glycine max

<400> SEQUENCE: 8
gtgaatggtg gctttgtgtt tgg                                              23

<210> SEQ ID NO 9
<211> LENGTH: 23
<212> TYPE: DNA
<213> ORGANISM: Glycine max

<400> SEQUENCE: 9
acaaagccac cattcactgt tgg                                              23

<210> SEQ ID NO 10
<211> LENGTH: 23
<212> TYPE: DNA
<213> ORGANISM: Glycine max

<400> SEQUENCE: 10
agttggccaa cagtgaatgg tgg                                              23

<210> SEQ ID NO 11
<211> LENGTH: 23
<212> TYPE: DNA
<213> ORGANISM: Glycine max

<400> SEQUENCE: 11
ttgagttggc caacagtgaa tgg                                              23

<210> SEQ ID NO 12
<211> LENGTH: 23
<212> TYPE: DNA
<213> ORGANISM: Glycine max

<400> SEQUENCE: 12
tgaaaggtca taaacaacat agg                                              23

<210> SEQ ID NO 13
<211> LENGTH: 23
<212> TYPE: DNA
<213> ORGANISM: Glycine max

<400> SEQUENCE: 13
caaacacttc atcacggtca agg                                              23

<210> SEQ ID NO 14
<211> LENGTH: 23
<212> TYPE: DNA
<213> ORGANISM: Glycine max

<400> SEQUENCE: 14
aaccaaaatc caaagttgca tgg                                              23

<210> SEQ ID NO 15
<211> LENGTH: 23

```
<212> TYPE: DNA
<213> ORGANISM: Glycine max

<400> SEQUENCE: 15
tgggagcata agggtggtag tgg                                              23

<210> SEQ ID NO 16
<211> LENGTH: 23
<212> TYPE: DNA
<213> ORGANISM: Glycine max

<400> SEQUENCE: 16
aatatatggg agcataaggg tgg                                              23

<210> SEQ ID NO 17
<211> LENGTH: 23
<212> TYPE: DNA
<213> ORGANISM: Glycine max

<400> SEQUENCE: 17
gtttggctgc tatgtgttta tgg                                              23

<210> SEQ ID NO 18
<211> LENGTH: 23
<212> TYPE: DNA
<213> ORGANISM: Glycine max

<400> SEQUENCE: 18
tttggctgct atgtgtttat ggg                                              23

<210> SEQ ID NO 19
<211> LENGTH: 23
<212> TYPE: DNA
<213> ORGANISM: Glycine max

<400> SEQUENCE: 19
ttggctgcta tgtgtttatg ggg                                              23

<210> SEQ ID NO 20
<211> LENGTH: 23
<212> TYPE: DNA
<213> ORGANISM: Glycine max

<400> SEQUENCE: 20
gcaactatgg acagagatta tgg                                              23

<210> SEQ ID NO 21
<211> LENGTH: 23
<212> TYPE: DNA
<213> ORGANISM: Glycine max

<400> SEQUENCE: 21
caccatttta caaggcactg tgg                                              23

<210> SEQ ID NO 22
<211> LENGTH: 23
<212> TYPE: DNA
<213> ORGANISM: Glycine max

<400> SEQUENCE: 22
cttcatctgg ctccacatag agg                                              23

<210> SEQ ID NO 23
```

```
<211> LENGTH: 23
<212> TYPE: DNA
<213> ORGANISM: Glycine max

<400> SEQUENCE: 23
ctctatgtgg agccagatga agg                                              23

<210> SEQ ID NO 24
<211> LENGTH: 23
<212> TYPE: DNA
<213> ORGANISM: Glycine max

<400> SEQUENCE: 24
ttctcggatg ttccttcatc tgg                                              23

<210> SEQ ID NO 25
<211> LENGTH: 23
<212> TYPE: DNA
<213> ORGANISM: Glycine max

<400> SEQUENCE: 25
agatgaagga acatccgaga agg                                              23

<210> SEQ ID NO 26
<211> LENGTH: 23
<212> TYPE: DNA
<213> ORGANISM: Glycine max

<400> SEQUENCE: 26
gatgaaggaa catccgagaa ggg                                              23

<210> SEQ ID NO 27
<211> LENGTH: 23
<212> TYPE: DNA
<213> ORGANISM: Glycine max

<400> SEQUENCE: 27
catccgagaa gggcgtgtat tgg                                              23

<210> SEQ ID NO 28
<211> LENGTH: 23
<212> TYPE: DNA
<213> ORGANISM: Glycine max

<400> SEQUENCE: 28
gtaccaatac acgcccttct cgg                                              23

<210> SEQ ID NO 29
<211> LENGTH: 23
<212> TYPE: DNA
<213> ORGANISM: Glycine max

<400> SEQUENCE: 29
agaagggcgt gtattggtac agg                                              23

<210> SEQ ID NO 30
<211> LENGTH: 23
<212> TYPE: DNA
<213> ORGANISM: Glycine max

<400> SEQUENCE: 30
ttgggacaaa cacttcatca cgg                                              23
```

```
<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gaatgattag gcatcgaacc                                              20

<210> SEQ ID NO 32
<211> LENGTH: 24
<212> TYPE: DNA
<213> ORGANISM: Artificial Sequence
<220> FEATURE:
<223> OTHER INFORMATION: primer

<400> SEQUENCE: 32
aaactcctca agggttccaa acac                                         24

<210> SEQ ID NO 33
<211> LENGTH: 25
<212> TYPE: DNA
<213> ORGANISM: Artificial Sequence
<220> FEATURE:
<223> OTHER INFORMATION: primer

<400> SEQUENCE: 33
aaactcctca agggttccaa acacc                                        25

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tccgtaccga gccgcaggaa                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
ccggcaggct gaagtccagc                                              20

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
atggacaaga agtacagcat cggc                                         24

<210> SEQ ID NO 37
<211> LENGTH: 24
<212> TYPE: DNA
<213> ORGANISM: Artificial Sequence
<220> FEATURE:
<223> OTHER INFORMATION: primer
```

```
<400> SEQUENCE: 37
aacttgtaga actcctcctg gctg                                          24

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
ttcaggaagt ccaggatggt cttg                                          24

<210> SEQ ID NO 39
<211> LENGTH: 24
<212> TYPE: DNA
<213> ORGANISM: Artificial Sequence
<220> FEATURE:
<223> OTHER INFORMATION: primer

<400> SEQUENCE: 39
agaactggaa gtccttgcgg aagt                                          24

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
ctgagcgagc tggacaaggc cgg                                           23

<210> SEQ ID NO 41
<211> LENGTH: 24
<212> TYPE: DNA
<213> ORGANISM: Artificial Sequence
<220> FEATURE:
<223> OTHER INFORMATION: primer

<400> SEQUENCE: 41
ttaggcgtag tcgggcacgt cgta                                          24

<210> SEQ ID NO 42
<211> LENGTH: 12
<212> TYPE: RNA
<213> ORGANISM: Streptococcus pyogenes

<400> SEQUENCE: 42
guuuuagagc ua                                                       12

<210> SEQ ID NO 43
<211> LENGTH: 25
<212> TYPE: RNA
<213> ORGANISM: Campylobacter jejuni

<400> SEQUENCE: 43
guuuuagucc cuuuuuaaau uucuu                                         25

<210> SEQ ID NO 44
<211> LENGTH: 14
<212> TYPE: RNA
<213> ORGANISM: Streptococcus pyogenes

<400> SEQUENCE: 44
```

-continued

```
uagcaaguua aaau                                            14

<210> SEQ ID NO 45
<211> LENGTH: 25
<212> TYPE: RNA
<213> ORGANISM: Campylobacter jejuni

<400> SEQUENCE: 45
aagaaauuua aaagggacu aaaau                                 25

<210> SEQ ID NO 46
<211> LENGTH: 11
<212> TYPE: RNA
<213> ORGANISM: Unknown
<220> FEATURE:
<223> OTHER INFORMATION: Parcubacteria bacterium

<400> SEQUENCE: 46
aaauuucuac u                                               11

<210> SEQ ID NO 47
<211> LENGTH: 12
<212> TYPE: RNA
<213> ORGANISM: Streptococcus pyogenes

<400> SEQUENCE: 47
aaggcuaguc cg                                              12

<210> SEQ ID NO 48
<211> LENGTH: 11
<212> TYPE: RNA
<213> ORGANISM: Campylobacter jejuni

<400> SEQUENCE: 48
aaagaguuug c                                               11

<210> SEQ ID NO 49
<211> LENGTH: 34
<212> TYPE: RNA
<213> ORGANISM: Streptococcus pyogenes

<400> SEQUENCE: 49
uuaucaacuu gaaaaagugg caccgagucg gugc                      34

<210> SEQ ID NO 50
<211> LENGTH: 38
<212> TYPE: RNA
<213> ORGANISM: Campylobacter jejuni

<400> SEQUENCE: 50
gggacucugc gggguuacaa uccccuaaaa ccgcuuuu                  38

<210> SEQ ID NO 51
<211> LENGTH: 22
<212> TYPE: RNA
<213> ORGANISM: Streptococcus thermophilus

<400> SEQUENCE: 51
guuuuagagc uguguuguuu cg                                   22

<210> SEQ ID NO 52
<211> LENGTH: 24
<212> TYPE: RNA
```

<213> ORGANISM: Streptococcus thermophilus

<400> SEQUENCE: 52
cgaaacaaca cagcgaguua aaau                                          24

<210> SEQ ID NO 53
<211> LENGTH: 13
<212> TYPE: RNA
<213> ORGANISM: Streptococcus thermophilus

<400> SEQUENCE: 53
aaggcuuagu ccg                                                      13

<210> SEQ ID NO 54
<211> LENGTH: 38
<212> TYPE: RNA
<213> ORGANISM: Streptococcus thermophilus

<400> SEQUENCE: 54
uacucaacuu gaaaaggugg caccgauucg guguuuuu                           38

<210> SEQ ID NO 55
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 55

Pro Lys Lys Lys Arg Lys Val
1               5

<210> SEQ ID NO 56
<211> LENGTH: 16
<212> TYPE: PRT
<213> ORGANISM: Artificial Sequence
<220> FEATURE:
<223> OTHER INFORMATION: nuclear localization sequence

<400> SEQUENCE: 56

Lys Arg Pro Ala Ala Thr Lys Lys Ala Gly Gln Ala Lys Lys Lys Lys
1               5                   10                  15

<210> SEQ ID NO 57
<211> LENGTH: 9
<212> TYPE: PRT
<213> ORGANISM: Artificial Sequence
<220> FEATURE:
<223> OTHER INFORMATION: nuclear localization sequence

<400> SEQUENCE: 57

Pro Ala Ala Lys Arg Val Lys Leu Asp
1               5

<210> SEQ ID NO 58
<211> LENGTH: 11
<212> TYPE: PRT
<213> ORGANISM: Artificial Sequence
<220> FEATURE:
<223> OTHER INFORMATION: nuclear localization sequence

<400> SEQUENCE: 58

Arg Gln Arg Arg Asn Glu Leu Lys Arg Ser Pro
1               5                   10

-continued

```
<210> SEQ ID NO 59
<211> LENGTH: 38
<212> TYPE: PRT
<213> ORGANISM: Artificial Sequence
<220> FEATURE:
<223> OTHER INFORMATION: nuclear localization sequence

<400> SEQUENCE: 59

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 60
<211> LENGTH: 42
<212> TYPE: PRT
<213> ORGANISM: Artificial Sequence
<220> FEATURE:
<223> OTHER INFORMATION: nuclear localization sequence

<400> SEQUENCE: 60

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 61
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 61

Val Ser Arg Lys Arg Pro Arg Pro
1               5

<210> SEQ ID NO 62
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 62

Pro Pro Lys Lys Ala Arg Glu Asp
1               5

<210> SEQ ID NO 63
<211> LENGTH: 8
<212> TYPE: PRT
<213> ORGANISM: Artificial Sequence
<220> FEATURE:
<223> OTHER INFORMATION: nuclear localization sequence

<400> SEQUENCE: 63

Pro Gln Pro Lys Lys Lys Pro Leu
1               5

<210> SEQ ID NO 64
<211> LENGTH: 12
```

```
<212> TYPE: PRT
<213> ORGANISM: Artificial Sequence
<220> FEATURE:
<223> OTHER INFORMATION: nuclear localization sequence

<400> SEQUENCE: 64

Ser Ala Leu Ile Lys Lys Lys Lys Met Ala Pro
1               5                   10

<210> SEQ ID NO 65
<211> LENGTH: 5
<212> TYPE: PRT
<213> ORGANISM: Artificial Sequence
<220> FEATURE:
<223> OTHER INFORMATION: nuclear localization sequence

<400> SEQUENCE: 65

Asp Arg Leu Arg Arg
1               5

<210> SEQ ID NO 66
<211> LENGTH: 7
<212> TYPE: PRT
<213> ORGANISM: Artificial Sequence
<220> FEATURE:
<223> OTHER INFORMATION: nuclear localization sequence

<400> SEQUENCE: 66

Pro Lys Gln Lys Lys Arg Lys
1               5

<210> SEQ ID NO 67
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 67

Arg Lys Leu Lys Lys Lys Ile Lys Lys Leu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: nuclear localization sequence

<400> SEQUENCE: 68

Arg Glu Lys Lys Lys Phe Leu Lys Arg Arg
1               5                   10

<210> SEQ ID NO 69
<211> LENGTH: 20
<212> TYPE: PRT
<213> ORGANISM: Artificial Sequence
<220> FEATURE:
<223> OTHER INFORMATION: nuclear localization sequence

<400> SEQUENCE: 69

Lys Arg Lys Gly Asp Glu Val Asp Gly Val Asp Glu Val Ala Lys Lys
1               5                   10                  15

Lys Ser Lys Lys
            20
```

```
<210> SEQ ID NO 70
<211> LENGTH: 17
<212> TYPE: PRT
<213> ORGANISM: Artificial Sequence
<220> FEATURE:
<223> OTHER INFORMATION: nuclear localization sequence

<400> SEQUENCE: 70

Arg Lys Cys Leu Gln Ala Gly Met Asn Leu Glu Ala Arg Lys Thr Lys
1               5                   10                  15

Lys

<210> SEQ ID NO 71
<211> LENGTH: 46
<212> TYPE: DNA
<213> ORGANISM: Glycine max

<400> SEQUENCE: 71
aagggaagaa gcctctctca agggttccaa acacaaagcc accatt              46

<210> SEQ ID NO 72
<211> LENGTH: 50
<212> TYPE: DNA
<213> ORGANISM: Glycine max

<400> SEQUENCE: 72
cagcagaaga agcctctctc aagggttcca aacacaaagc caccattcac          50

<210> SEQ ID NO 73
<211> LENGTH: 72
<212> TYPE: DNA
<213> ORGANISM: Glycine max

<400> SEQUENCE: 73
aaagtggaag ttcaagggaa gaagcctctc tcaagggttc aaacacaaa gccaccattc  60 actgttggcc aa                                                    72

<210> SEQ ID NO 74
<211> LENGTH: 57
<212> TYPE: DNA
<213> ORGANISM: Glycine max

<400> SEQUENCE: 74
cagaagaagc ctctctcaag ggttccaaac acaaagccac cattcactgt tggccaa   57

<210> SEQ ID NO 75
<211> LENGTH: 43
<212> TYPE: DNA
<213> ORGANISM: Glycine max

<400> SEQUENCE: 75
aagggaagaa gcctctctgg gttccaaaca caaagccacc att                 43

<210> SEQ ID NO 76
<211> LENGTH: 37
<212> TYPE: DNA
<213> ORGANISM: Glycine max

<400> SEQUENCE: 76
aagggaagaa gcctcttcca aacacaaagc caccatt                        37

<210> SEQ ID NO 77
<211> LENGTH: 34
```

<212> TYPE: DNA
<213> ORGANISM: Glycine max

<400> SEQUENCE: 77
aagggaagaa gcctctctac acaaagccac catt                                    34

<210> SEQ ID NO 78
<211> LENGTH: 42
<212> TYPE: DNA
<213> ORGANISM: Glycine max

<400> SEQUENCE: 78
aagggaagaa gcctctctgg ttccaaacac aaagccacca tt                           42

<210> SEQ ID NO 79
<211> LENGTH: 27
<212> TYPE: DNA
<213> ORGANISM: Glycine max

<400> SEQUENCE: 79
aagggttcca aacacaaagc caccatt                                            27

<210> SEQ ID NO 80
<211> LENGTH: 37
<212> TYPE: DNA
<213> ORGANISM: Glycine max

<400> SEQUENCE: 80
aagggaagaa gcctctctca aacacaaagc caccatt                                 37

<210> SEQ ID NO 81
<211> LENGTH: 40
<212> TYPE: DNA
<213> ORGANISM: Glycine max

<400> SEQUENCE: 81
aagggaagaa gcctctggtt ccaaacacaa agccaccatt                              40

<210> SEQ ID NO 82
<211> LENGTH: 44
<212> TYPE: DNA
<213> ORGANISM: Glycine max

<400> SEQUENCE: 82
aagggaagaa gcctctctag ggttccaaac acaaagccac catt                         44

<210> SEQ ID NO 83
<211> LENGTH: 47
<212> TYPE: DNA
<213> ORGANISM: Glycine max

<400> SEQUENCE: 83
aagggaagaa gcctctcttc aagggttcca aacacaaagc caccatt                      47

<210> SEQ ID NO 84
<211> LENGTH: 46
<212> TYPE: DNA
<213> ORGANISM: Glycine max

<400> SEQUENCE: 84
cagcagaaga agcctctctg gttccaaaca caaagccacc attcac                       46

<210> SEQ ID NO 85

```
<211> LENGTH: 46
<212> TYPE: DNA
<213> ORGANISM: Glycine max

<400> SEQUENCE: 85
cagcagaaga agcctctcgg gttccaaaca caaagccacc attcac         46

<210> SEQ ID NO 86
<211> LENGTH: 43
<212> TYPE: DNA
<213> ORGANISM: Glycine max

<400> SEQUENCE: 86
cagcagaaga agcctctctt ccaaacacaa agccaccatt cac             43

<210> SEQ ID NO 87
<211> LENGTH: 46
<212> TYPE: DNA
<213> ORGANISM: Glycine max

<400> SEQUENCE: 87
cagcagaaga agcctctagg gttccaaaca caaagccacc attcac         46

<210> SEQ ID NO 88
<211> LENGTH: 50
<212> TYPE: DNA
<213> ORGANISM: Glycine max

<400> SEQUENCE: 88
cagcagaaga agcctctctt tttcaagggt tccaaacaca aagccaccat    50

<210> SEQ ID NO 89
<211> LENGTH: 28
<212> TYPE: DNA
<213> ORGANISM: Glycine max

<400> SEQUENCE: 89
cagcagaaaa cacaaagcca ccattcac                              28

<210> SEQ ID NO 90
<211> LENGTH: 43
<212> TYPE: DNA
<213> ORGANISM: Glycine max

<400> SEQUENCE: 90
gggaggtgga ggccgtgtgg ccaaacacaa agccaccatt cac             43

<210> SEQ ID NO 91
<211> LENGTH: 39
<212> TYPE: DNA
<213> ORGANISM: Glycine max

<400> SEQUENCE: 91
cagcagaaga agcctctcta acacaaagcc accattcac                  39

<210> SEQ ID NO 92
<211> LENGTH: 49
<212> TYPE: DNA
<213> ORGANISM: Glycine max

<400> SEQUENCE: 92
cagcagaaga agcctcttca agggttccaa acacaaagcc accattcac      49
```

```
<210> SEQ ID NO 93
<211> LENGTH: 64
<212> TYPE: DNA
<213> ORGANISM: Glycine max

<400> SEQUENCE: 93
aaagtggaag ttcaagggaa gaagcctctc tccaaacaca agccaccat tcactgttgg    60 ccaa                                                                64

<210> SEQ ID NO 94
<211> LENGTH: 67
<212> TYPE: DNA
<213> ORGANISM: Glycine max

<400> SEQUENCE: 94
aaagtggaag ttcaagggaa gaagcctctc tgttccaaac acaaagccac cattcactgt    60
tggccaa                                                              67

<210> SEQ ID NO 95
<211> LENGTH: 66
<212> TYPE: DNA
<213> ORGANISM: Glycine max

<400> SEQUENCE: 95
aaagtggaag ttcaagggaa gaagcctctc tttccaaaca caaagccacc attcactgtt    60
ggccaa                                                               66

<210> SEQ ID NO 96
<211> LENGTH: 70
<212> TYPE: DNA
<213> ORGANISM: Glycine max

<400> SEQUENCE: 96
aaagtggaag ttcaagggaa gaagcctctc tagggttcca acacaaagc caccattcac    60 tgttggccaa                                                           70

<210> SEQ ID NO 97
<211> LENGTH: 65
<212> TYPE: DNA
<213> ORGANISM: Glycine max

<400> SEQUENCE: 97
aaagtggaag ttcaagggaa gaagcctctc ttccaaacac aaagccacca ttcactgttg    60
gccaa                                                                65

<210> SEQ ID NO 98
<211> LENGTH: 70
<212> TYPE: DNA
<213> ORGANISM: Glycine max

<400> SEQUENCE: 98
aaagtggaag ttcaagggaa gaagcctctc aagggttcca acacaaagc caccattcac    60 tgttggccaa                                                           70

<210> SEQ ID NO 99
<211> LENGTH: 65
<212> TYPE: DNA
<213> ORGANISM: Glycine max

<400> SEQUENCE: 99
```

```
aaagtggaag ttcaagggaa gaagcctctc ttccaaacac aaagccacca ttcactgttg    60
gccaa                                                                65

<210> SEQ ID NO 100
<211> LENGTH: 67
<212> TYPE: DNA
<213> ORGANISM: Glycine max

<400> SEQUENCE: 100
aaagtggaag ttcaagggaa gaagcctctc tgttccaaac acaaagccac cattcactgt    60
tggccaa                                                              67

<210> SEQ ID NO 101
<211> LENGTH: 65
<212> TYPE: DNA
<213> ORGANISM: Glycine max

<400> SEQUENCE: 101
aaagtggaag ttcaagggaa gaagcctctc ttccaaacac aaagccacca ttcactgttg    60
gccaa                                                                65

<210> SEQ ID NO 102
<211> LENGTH: 64
<212> TYPE: DNA
<213> ORGANISM: Glycine max

<400> SEQUENCE: 102
aaagtggaag ttcaagggaa gaagcctctc tccaaacaca agccaccat tcactgttgg    60 ccaa                                                                 64

<210> SEQ ID NO 103
<211> LENGTH: 65
<212> TYPE: DNA
<213> ORGANISM: Glycine max

<400> SEQUENCE: 103
aaagtggaag ttcaagggaa gaagcctctc ttccaaacac aaagccacca ttcactgttg    60
gccaa                                                                65

<210> SEQ ID NO 104
<211> LENGTH: 65
<212> TYPE: DNA
<213> ORGANISM: Glycine max

<400> SEQUENCE: 104
aaagtggaag ttcaagggaa gaagcctctc ttccaaacac aaagccacca ttcactgttg    60
gccaa                                                                65

<210> SEQ ID NO 105
<211> LENGTH: 70
<212> TYPE: DNA
<213> ORGANISM: Glycine max

<400> SEQUENCE: 105
aaagtggaag ttcaagggaa gaagcctctc aagggttcca acacaaagc caccattcac    60 tgttggccaa                                                           70

<210> SEQ ID NO 106
<211> LENGTH: 70
```

```
<212> TYPE: DNA
<213> ORGANISM: Glycine max

<400> SEQUENCE: 106
aaagtggaag ttcaagggaa gaagcctctc tagggttcca acacaaagc caccattcac    60 tgttggccaa                                                          70

<210> SEQ ID NO 107
<211> LENGTH: 70
<212> TYPE: DNA
<213> ORGANISM: Glycine max

<400> SEQUENCE: 107
aaagtggaag ttcaagggaa gaagcctctc tagggttcca acacaaagc caccattcac    60 tgttggccaa                                                          70

<210> SEQ ID NO 108
<211> LENGTH: 53
<212> TYPE: DNA
<213> ORGANISM: Glycine max

<400> SEQUENCE: 108
cagaagaagc ctctcgggtt ccaaacacaa agccaccatt cactgttggc caa          53

<210> SEQ ID NO 109
<211> LENGTH: 53
<212> TYPE: DNA
<213> ORGANISM: Glycine max

<400> SEQUENCE: 109
cagaagaagc ctctctggtt ccaaacacaa agccaccatt cactgttggc caa          53

<210> SEQ ID NO 110
<211> LENGTH: 49
<212> TYPE: DNA
<213> ORGANISM: Glycine max

<400> SEQUENCE: 110
cagaagaagc ctctctccaa acacaaagcc accattcact gttggccaa               49

<210> SEQ ID NO 111
<211> LENGTH: 55
<212> TYPE: DNA
<213> ORGANISM: Glycine max

<400> SEQUENCE: 111
cagaagaagc ctctctaggg ttccaaacac aaagccacca ttcactgttg gccaa        55

<210> SEQ ID NO 112
<211> LENGTH: 55
<212> TYPE: DNA
<213> ORGANISM: Glycine max

<400> SEQUENCE: 112
cagaagaagc ctctctaggg ttccaaacac aaagccacca ttcactgttg gccaa        55

<210> SEQ ID NO 113
<211> LENGTH: 55
<212> TYPE: DNA
<213> ORGANISM: Glycine max

<400> SEQUENCE: 113
```

```
cagaagaagc ctctctaggg ttccaaacac aaagccacca ttcactgttg gccaa          55

<210> SEQ ID NO 114
<211> LENGTH: 58
<212> TYPE: DNA
<213> ORGANISM: Glycine max

<400> SEQUENCE: 114
cagaagaagc ctctcttcaa gggttccaaa cacaaagcca ccattcactg ttggccaa      58

<210> SEQ ID NO 115
<211> LENGTH: 54
<212> TYPE: DNA
<213> ORGANISM: Glycine max

<400> SEQUENCE: 115
cagaagaagc ctctctgggt tccaaacaca agccaccat tcactgttgg ccaa           54

<210> SEQ ID NO 116
<211> LENGTH: 50
<212> TYPE: DNA
<213> ORGANISM: Glycine max

<400> SEQUENCE: 116
cagaagaagc ctctcttcca aacacaaagc caccattcac tgttggccaa               50

<210> SEQ ID NO 117
<211> LENGTH: 55
<212> TYPE: DNA
<213> ORGANISM: Glycine max

<400> SEQUENCE: 117
cagaagaagc ctctctaggg ttccaaacac aaagccacca ttcactgttg gccaa         55

<210> SEQ ID NO 118
<211> LENGTH: 46
<212> TYPE: DNA
<213> ORGANISM: Glycine max

<400> SEQUENCE: 118
cagaagaagc ctctctaaca caaagccacc attcactgtt ggccaa                   46

<210> SEQ ID NO 119
<211> LENGTH: 47
<212> TYPE: DNA
<213> ORGANISM: Glycine max

<400> SEQUENCE: 119
cagaagaagc ctctccaaac acaaagccac cattcactgt tggccaa                  47

<210> SEQ ID NO 120
<211> LENGTH: 46
<212> TYPE: DNA
<213> ORGANISM: Glycine max

<400> SEQUENCE: 120
cagaagaagc ctctctaaca caaagccacc attcactgtt ggccaa                   46
```